US009765363B1

(12) United States Patent
Renninger

(10) Patent No.: US 9,765,363 B1
(45) Date of Patent: Sep. 19, 2017

(54) APPARATUS FOR MAKING BIO-ORGANIC COMPOUNDS

(75) Inventor: Neil Stephen Renninger, Oakland, CA (US)

(73) Assignee: Amyris, Inc., Emeryville, CA (US)

( * ) Notice: Subject to any disclaimer, the term of this patent is extended or adjusted under 35 U.S.C. 154(b) by 570 days.

(21) Appl. No.: 11/807,048

(22) Filed: May 25, 2007

Related U.S. Application Data

(60) Provisional application No. 60/808,989, filed on May 26, 2006, provisional application No. 60/808,666, filed on May 26, 2006, provisional application No. 60/870,592, filed on Dec. 12, 2006, provisional application No. 60/922,782, filed on Apr. 10, 2007.

(51) Int. Cl.

| | |
|---|---|
| C12P 7/04 | (2006.01) |
| C12P 7/02 | (2006.01) |
| C12P 5/00 | (2006.01) |
| C12P 15/00 | (2006.01) |
| C12P 23/00 | (2006.01) |
| C12N 1/20 | (2006.01) |
| C12N 1/00 | (2006.01) |
| C12P 7/00 | (2006.01) |
| C12P 5/02 | (2006.01) |
| C12N 15/52 | (2006.01) |

(52) U.S. Cl.
CPC .............. *C12P 7/00* (2013.01); *C12N 15/52* (2013.01); *C12P 5/007* (2013.01); *C12P 5/026* (2013.01); *C12P 7/02* (2013.01); *C12P 7/04* (2013.01)

(58) Field of Classification Search
CPC .... C12P 7/00; C12P 7/02; C12P 5/007; C12P 5/026; C12N 15/52
USPC .............. 435/157, 155, 166, 127, 67, 252.3, 435/254.11
See application file for complete search history.

(56) References Cited

U.S. PATENT DOCUMENTS

| | | | |
|---|---|---|---|
| 2,945,059 A | | 7/1960 | Shunk et al. |
| 4,865,973 A | | 9/1989 | Kollerup et al. |
| 5,510,247 A | * | 4/1996 | Komives et al. ............... 435/41 |
| 5,763,237 A | | 6/1998 | Savithiry et al. |
| 6,407,306 B1 | | 6/2002 | Peter et al. |
| 2002/0168733 A1 | | 11/2002 | Clark et al. |
| 2004/0229326 A1 | | 11/2004 | Ben-Bassat et al. |
| 2005/0266518 A1 | * | 12/2005 | Berry et al. ..................... 435/67 |
| 2006/0079476 A1 | * | 4/2006 | Keasling et al. ............... 514/44 |

FOREIGN PATENT DOCUMENTS

| | | |
|---|---|---|
| CH | 677791 A5 | 6/1991 |
| DE | 31 38493 | 4/1983 |
| DE | 102005018256 | 8/2006 |
| EP | 0 216 221 | 4/1987 |
| JP | 08-29108 | 3/1996 |
| JP | 2002535970 A | 10/2002 |
| JP | 2006-109784 | 4/2006 |
| WO | WO-00/44912 A1 | 10/2000 |
| WO | WO-2005/033287 A2 | 4/2005 |
| WO | 2005/078110 A | 8/2005 |
| WO | WO 2005/078110 | 8/2005 |
| WO | WO 2006/014837 A1 | 2/2006 |
| WO | WO 2006/025735 A2 | 3/2006 |
| WO | 2007/093962 A2 | 8/2007 |

OTHER PUBLICATIONS

Sajc et al., Bioreactors for plant engineering: an outlook for further research. Biochem. Eng. J., 2000, vol. 4: 89-99.*
Diamond et al., Aqueous Two-Phase Systems for biomolecule separation. Adv. Biochem. Eng. Biotechnol., 1992, vol. 47: 89-135.*
Mancuso et al., C15, C20, and C25 isoprenoid homologues in glycerol diether phospholipids of methanogenic archaebacteria. J. Lipid Res., 1986, vol. 26: 1120-1125.*
Mathys et al., Alkanol removal from the aploar phase of a Two-liquid phase biconversion system. Part 2: effect of fermentation medium on batch distillation. J. Chem. Technol. Biotechnol., 1998, vol. 71: 326-334.*
Newman et al., High-level production of Amorpha-4,11-diene in a two-phase partioning bioreactor of metabolically engineered *Escherichia coli*. Biotechnol. Bioeng., 2006, vol. 95 (4): 684-691, published online Jul. 28, 2006.*
Schmid et al., Developments toward large-scale bioprocesses in the presence of bulk amounts of organic solvents. Extremophiles, 1998, vol. 2: 249-256.*
Material Safety Data Sheet for Dodecane; 6 pages, downloaded from internet on Oct. 28, 2014.*
Rojas et al., "Biotransformation in Double-Phase systems: Physiological Responses of Pseudomonas Putida Dot-T1E to a Double Phase Made of Aliphatic alcohols and Biosynthesis of substituted catechols", *Applied and Environmental Microbiology*, vol. 70, No. 6, Jun. 2004, pp. 3637-3543, XP002456441, p. 3637-3638.
International Search Report for PCT/US2007/012467 dated Oct. 25, 2007.
Craft et al., 1992, "Relative solubility, stability, and absorptivity of lutein and β-carotene in organic solvents," J. Agric. Food Chem., vol. 40:431-434.
IARC Working group on the evaluation of cancer-preventative agents, 1998, "vol. 2: Carotenoids".
Da Rocha, "Model-based strategies for computer-aided operation of a recombinant *E. coli* fermentation," Ph.D. Thesis, Universidade do Minho, Braga, Portugal (2003) 285 pages.
European Search Report for appl. No. EP 07 777278.8, dated Jan. 24, 2013, 9 pgs.
Byun et al., "Two-Phase Airlift Fermentor Operation with Elicitation for the Enhanced Production of Benzophenanthridine Alkaloids in Cell Suspensions of *Escherichia* californica", Biotechnology and Bioengineering vol. 44, pp. 14-20 (1994).

(Continued)

*Primary Examiner* — Ganapathirama Raghu
(74) *Attorney, Agent, or Firm* — Squire Patton Boggs (US) LLP

(57) ABSTRACT

A system and method for producing bio-organic compounds may include a vessel, a first phase comprising an aqueous medium including host cells capable of producing a bio-organic compound, where the bio-organic compound comprises a second phase in contact with the aqueous medium.

13 Claims, 10 Drawing Sheets

(56) References Cited

OTHER PUBLICATIONS

Schügerl "Integrated processing of biotechnology products", Biotechnology Advances 18, pp. 581-599 (2000).

Stark et al., "Extractive Bioconversion of 2-Phenylethanol from L-Phenylalanine by *Saccharomyces cerevisiae*", Biotechnol. Prog. 18, pp. 514-523 (2002).

Stark et al., "In Situ Product Removal (ISPR) in Whole Cell Biotechnology During the Last Twenty Years", Biotechnology, vol. 80, pp. 149-175 (2003).

Rohas et al., "Biotransformation in Double-Phase Systems: Physiological Responses of Pseudomonas Putida DOt-T1E to a Double Phase Made of Aliphatic Alcohols and Biosynthesis of Substituted Catechols", applied and Environcmental Microbiology, vol. 70, No. 6, pp. 3637-3643 (2004).

Mattiasson et al., "Extractive Bioconversions with Emphasis on Solvent Production", Biotechnology and Genetic Engineering Reviews vol. 3, pp. 137-174 (1985).

Martin et al., "Engineering a mevalonate pathway in *Escherichia coli* for production of terpenoids", Nature Biotechnology vol. 21, No. 7, pp. 796-802 (2003).

English translation of KIPO's Notice of Preliminary Rejection dated Jan. 16, 2004, in Korean Patent Application No. 10-2008-7031413, 6 pages.

Datasheet "High Purity of d-Linonene" Florida Chemical Company, 2006, 4 pp.

Leon, Rosa et al. "Microalgae mediated photoproduction of β-carotene in aqueous—organic two phase systems," Biomolecular Engineering, 2003, vol. 20, pp. 177-182.

Massaldi, Hugo A. et al. "Simple Technique to Determine Solubilities of Sparingly Soluble Organics: Solubility and Activity Coefficients of d-Limonene, n-Butylbenzene, and n-Hexyl Acetate in Water and Sucrose Solutions," Journal of Chemical and Engineering Data, 1973, vol. 18, No. 4, pp. 393-397.

Standbury, Peter et al. "Chapter 7: Design of a Fermenter," Principles of Fermentation Technology, $2^{nd}$ Edn., 1995, pp. 167-170 and 269-271.

Telcelao, et al. "Development of reaction system for the selective conversion of (−)—trans-carveol to (−)—carvone with whole cells of Rhodococcus erythropolis DCL14," Journal of Molecular Catalysis B Enzymatic, 2001, vol. 11, pp. 719-724.

\* cited by examiner

Mevalonate pathway

DXP pathway

SEQUENCE LISTING

```
<160> NUMBER OF SEQ ID NOS: 54

<210> SEQ ID NO 1
<211> LENGTH: 4247
<212> TYPE: DNA
<213> ORGANISM: Artificial Sequence
<220> FEATURE:
<223> OTHER INFORMATION: MevT66 operon

<400> SEQUENCE: 1
```

```
gaattcaaag gaggaaaata aaatgaagaa ctgtgtgatt gtttctgcgg tccgcacggc        60
gatcggcagc tttaacggct cttttagcga g caccctctgca atcgatctgg gtgcgacggt      120
cattaaggcc gccattgaac gcgccaaaat cgacagccag cacgttgatg aggtgatcat       180
gggcaatgtg ttacaagccg gcctgggtca aaacccagcg cgtcaagcac tgttaaaatc       240
tggtctggcc gagaccgtgt gtggcttcac cgtcaataag gtttgcggct ctggcctgaa       300
gagcgtggcc ctggcagcac aagcgattca agccggtcag gcacaaagca tcgttgcggg       360
tggcatggag aacatgtctc tggcgccgta cttattagat gccaaagccc gcagcggtta       420
tcgcctgggc gatggtcagg tgtacgacgt catcttacgc gatggcttaa tgtgcgcgac       480
ccacggttac cacatgggta ttacggccga aaacgtggcg aaagaatacg gcattacgcg       540
cgagatgcag gatgaattag cactgcactc tcagcgcaaa gcagcagccg cgatcgagtc       600
tggtgcgttt acggcggaaa tcgtgccagt taacgtggtc acgcgcaaga agacgttcgt       660
tttcagccag gacgagttcc cgaaggcaaa cagcaccgcg gaggccttag gtgccttacg       720
cccagccttt gacaaagcgg gcacggtcac cgccggtaat gcgagcggca tcaatgatgg       780
tgcagcggca ctggtcatca tggaagagag cgccgcatta gcagcgggtc tgaccccatt       840
agcgcgcatt aaatcttatg ccagcggcgg cgtcccacca gccctgatgg gcatgggtcc       900
ggtcccagcc acgcaaaaag ccctgcaatt agcgggcctg caactggccg acattgatct       960
gatcgaggcg aacgaggcgt tgcagcgca gttcctggcg gtgggtaaga atctgggctt      1020
cgacagcgag aaagtcaatg tgaacggtgg cgcgattgcg ttaggccatc cgattggtgc      1080
aagcggcgca cgcatcttag tgacgttact gcacgccatg caggcacgcg acaagacctt      1140
aggcctggcg accttatgta ttggtggcgg tcaaggtatc gccatggtga tcgaacgcct      1200
gaactgaaga tctaggagga aagcaaaatg aaactgagca ccaagctgtg ctggtgtggc      1260
atcaagggtc gcctgcgccc acaaaagcag caacagctgc acaacacgaa cctgcaaatg      1320
accgagctga aaaagcagaa gacggccgag caaaagaccc gccgcagaa cgttggcatc      1380
aagggcatcc agatttatat cccgacgcag tgtgtcaacc aatctgagct ggagaaattc      1440
gatggcgtca gccagggtaa gtacaccatc ggcctgggcc agaccaacat gagcttcgtg      1500
aacgaccgtg aggacatcta ttctatgagc ctgacggtgc tgtctaagct gatcaagagc      1560
tacaacatcg acacgaataa gatcggtcgt ctggaggtgg gtacgagac gctgattgac      1620
aagagcaaaa gcgtgaagtc tgtcttaatg cagctgttcg gcgagaacac ggatgtcgag      1680
ggtatcgaca ccctgaacgc gtgttacggc ggcaccaacg cactgttcaa tagcctgaac      1740
tggattgaga gcaacgcctg ggatggccgc gatgcgatcg tcgtgtgcgg cgatatcgcc      1800
atctatgaca agggtgcggc acgtccgacc ggcggtgcag gcaccgttgc gatgtggatt      1860
ggcccggacg caccaattgt cttcgattct gtccgcgcgt cttacatgga gcacgcctac      1920
gacttttaca gccggacttc acgagcgaaa tacccgtacg tggacggcca cttctctctg      1980
acctgctatg tgaaggcgct ggaccaggtt tataagtctt atagcaaaaa ggcgatttct      2040
aagggcctgg tcagcgaccc ggcaggcagc gacgccctga acgtgctgaa gtatttcgac      2100
tacaacgtgt tccatgtccc gacctgcaaa ttagtgacca atctttatgg ccgcctgtta      2160
tataatgatt tccgtgccaa cccgcagctg ttcccggagg ttgacgccga gctggcgacg      2220
cgtgattacg acgagagcct gaccgacaag aacatcgaga agaccttcgt caacgtcgcg      2280
aagccgttcc acaaagagcg tgtggcccaa agcctgatcg tcccgaccaa cacgggcaac      2340
atgtataccg cgtctgtcta cgcggcattc gcgagcctgc tgaattacgt cggttctgac      2400
```

```
gacctgcagg gcaagcgcgt tggcctgttc agctacggta gcggcttagc ggccagcctg   2460
tatagctgca aaattgtcgg cgacgtccag cacatcatca aggagctgga catcaccaac   2520
aagctggcga agcgcatcac cgagacgccg aaagattacg aggcagcgat cgagttacgc   2580
gagaatgcgc atctgaagaa gaacttcaag ccgcaaggta gcatcgagca cctgcagagc   2640
ggcgtctact acctgacgaa cattgacgac aagttccgcc gttcttatga cgtcaaaaag   2700
taactagtag gaggaaaaca tcatggtgct gacgaacaaa accgtcatta gcggcagcaa   2760
ggtgaagtct ctgagcagcg cccaaagctc tagcagcggc ccgtctagca gcagcgagga   2820
ggacgacagc cgtgacattg agtctctgga caagaagatc cgcccgctgg aggagttaga   2880
ggccctgctg agcagcggca acaccaagca gctgaagaac aaggaagttg cagcgctggt   2940
gatccacggt aagctgccac tgtatgcgct ggaaaagaaa ctgggcgata cgacgcgtgc   3000
ggtcgcggtg cgtcgcaaag ccttaagcat cttagcggag gccccggtgt tagccagcga   3060
ccgcctgccg tacaagaact acgactacga ccgcgtgttt ggcgcgtgct gcgagaatgt   3120
cattggctac atgccgttac cggttggtgt gatcggcccg ctggtcattg atggcacgag   3180
ctatcacatt ccaatggcga ccacggaagg ttgcttagtc gccagcgcca tgcgtggctg   3240
taaggcgatt aacgccggcg gtggcgcgac gaccgtgtta accaaggatg gtatgacgcg   3300
cggtccggtc gtccgcttcc caacgctgaa gcgcagcggc gcgtgtaaga tttggctgga   3360
ttctgaggag ggccaaaacg cgatcaagaa agccttcaac tctacgagcc gtttcgcgcg   3420
tttacagcat atccagacct gcctggccgg cgacctgctg ttcatgcgct ccgcaccac    3480 cacgggcgat gcgatgggca tgaacatgat cagcaagggc gtcgaatata gcctgaaaca   3540
aatggtggaa gaatatggct gggaggacat ggaggttgtc tctgtgagcg gcaactattg   3600
caccgacaag aagccggcag ccattaactg gattgagggt cgcggcaaaa gcgtcgtggc   3660
agaagcgacc atcccaggcg acgtggtccg taaggttctg aagagcgacg tcagcgccct   3720
ggttgagtta aatatcgcga aaaacctggt cggcagcgcg atggcgggca gcgtgggtgg   3780
ctttaacgca catgcagcga atctggttac ggcggttttc ttagccttag gtcaggaccc   3840
agcccaaaat gtcgagagca gcaactgcat taccttaatg aaagaggttg acggtgacct   3900
gcgcatcagc gtttctatgc cgtctatcga ggtcggcacg atcggcggcg gcaccgtttt   3960
agaaccgcaa ggtgcgatgc tggatctgct gggcgtgcgc ggcccacatg caacggcccc   4020
aggcaccaat gcccgccaac tggcccgtat cgtggcctgc gcggttctgg cgggtgagct   4080
gagcctgtgc gccgcattag ccgcgggcca tttagttcaa tctcacatga cccacaaccg   4140
caagccggca gaaccaacca agccaaataa cctggacgca accgacatta accgtctgaa   4200
ggatggcagc gtcacgtgca ttaaaagctg agcatgctac taagctt              4247
```

<210> SEQ ID NO 2
<211> LENGTH: 49
<212> TYPE: DNA
<213> ORGANISM: Artificial Sequence
<220> FEATURE:
<223> OTHER INFORMATION: Primer 4-49 mvaA SpeI

<400> SEQUENCE: 2
gctactagta ggaggaaaac atcatgcaaa gtttagataa gaatttccg                49

<210> SEQ ID NO 3
<211> LENGTH: 39
<212> TYPE: DNA

<213> ORGANISM: Artificial Sequence
<220> FEATURE:
<223> OTHER INFORMATION: Primer 4-49 mvaAR XbaI

<400> SEQUENCE: 3
gcttctagac tattgttgtc taatttcttg taaaatgcg                              39

<210> SEQ ID NO 4
<211> LENGTH: 55
<212> TYPE: DNA
<213> ORGANISM: Artificial Sequence
<220> FEATURE:
<223> OTHER INFORMATION: Primer HMGS 5' Sa mvaS-S

<400> SEQUENCE: 4
gaactgaaga tctaggagga aagcaaaatg acaataggta tcgacaaaat aaact           55

<210> SEQ ID NO 5
<211> LENGTH: 52
<212> TYPE: DNA
<213> ORGANISM: Artificial Sequence
<220> FEATURE:
<223> OTHER INFORMATION: Primer HMGS 3' Sa mvaS-AS

<400> SEQUENCE: 5
ttgcatgatg ttttcctcct actagttact ctggtctgtg atattcgcga ac              52

<210> SEQ ID NO 6
<211> LENGTH: 42
<212> TYPE: DNA
<213> ORGANISM: Artificial Sequence
<220> FEATURE:
<223> OTHER INFORMATION: Primer 19-25 atoB SfiI-S

<400> SEQUENCE: 6
gctaggccat cctggccatg aagaactgtg tgattgtttc tg                         42

<210> SEQ ID NO 7
<211> LENGTH: 33
<212> TYPE: DNA
<213> ORGANISM: Artificial Sequence
<220> FEATURE:
<223> OTHER INFORMATION: Primer 19-25 mvaA-AsiSI-AS

<400> SEQUENCE: 7
gcttgcgatc gccggcggat ttgtcctact cag                                   33

<210> SEQ ID NO 8
<211> LENGTH: 35
<212> TYPE: DNA
<213> ORGANISM: Artificial Sequence
<220> FEATURE:
<223> OTHER INFORMATION: Primer 9-70C

<400> SEQUENCE: 8
ccacctcgag atgtcattac cgttcttaac ttctg                                 35

<210> SEQ ID NO 9
<211> LENGTH: 41
<212> TYPE: DNA
<213> ORGANISM: Artificial Sequence
<220> FEATURE:
<223> OTHER INFORMATION: Primer 26-39B

<400> SEQUENCE: 9
tggtggagct cttatttaag ctgggtaaat gcagataatc g                          41

<210> SEQ ID NO 10
<211> LENGTH: 39
<212> TYPE: DNA
<213> ORGANISM: Artificial Sequence
<220> FEATURE:
<223> OTHER INFORMATION: Primer 26-39A

<400> SEQUENCE: 10
ttcttgagct cttattcctt tggtagacca gtctttgcg                    39

<210> SEQ ID NO 11
<211> LENGTH: 51
<212> TYPE: DNA
<213> ORGANISM: Artificial Sequence
<220> FEATURE:
<223> OTHER INFORMATION: Primers 4-40 mvaEF BamHI

<400> SEQUENCE: 11
tatggatcct aaggaggata tttagatgaa aacagtagtt attattgatg c       51

<210> SEQ ID NO 12
<211> LENGTH: 40
<212> TYPE: DNA
<213> ORGANISM: Artificial Sequence
<220> FEATURE:
<223> OTHER INFORMATION: Primer 4-40 mvaER HindIII

<400> SEQUENCE: 12
agctaagctt ttattgtttt cttaaatcat ttaaaatagc                   40

<210> SEQ ID NO 13
<211> LENGTH: 51
<212> TYPE: DNA
<213> ORGANISM: Artificial Sequence
<220> FEATURE:
<223> OTHER INFORMATION: Primer 4-40 mvaSF BglII

<400> SEQUENCE: 13
tatagatctt aaggaggata tttagatgac aattgggatt gataaaatta g       51

<210> SEQ ID NO 14
<211> LENGTH: 32
<212> TYPE: DNA
<213> ORGANISM: Artificial Sequence
<220> FEATURE:
<223> OTHER INFORMATION: Primer 4-39 mvaSR BamHI

<400> SEQUENCE: 14
tttggatcct tagtttcgat aagagcgaac gg                           32

<210> SEQ ID NO 15
<211> LENGTH: 45
<212> TYPE: DNA
<213> ORGANISM: Artificial Sequence
<220> FEATURE:
<223> OTHER INFORMATION: Primer 67-1A-C for PCR amplification of the
      coding sequence of the dxs gene

<400> SEQUENCE: 15
acactcgagg aggaataaat gagttttgat attgccaaat acccg              45

<210> SEQ ID NO 16
<211> LENGTH: 37
<212> TYPE: DNA
<213> ORGANISM: Artificial Sequence

```
<220> FEATURE:
<223> OTHER INFORMATION: Primer 67-1B-C for PCR amplification of the
      coding sequence of the dxs gene

<400> SEQUENCE: 16
tgatggtacc ttatgccagc caggccttga ttttggc                              37

<210> SEQ ID NO 17
<211> LENGTH: 45
<212> TYPE: DNA
<213> ORGANISM: Artificial Sequence
<220> FEATURE:
<223> OTHER INFORMATION: Primer 67-1C-C for PCR amplification of the
      coding sequence of the dxr gene

<400> SEQUENCE: 17
actaggtacc aggaggaata atgaagcaa ctcaccattc tgggc                      45

<210> SEQ ID NO 18
<211> LENGTH: 37
<212> TYPE: DNA
<213> ORGANISM: Artificial Sequence
<220> FEATURE:
<223> OTHER INFORMATION: Primer 67-1D-C for PCR amplification of the
      coding sequence of the dxr gene

<400> SEQUENCE: 18
aattgatggg ccctcagctt gcgagacgca tcacctc                              37

<210> SEQ ID NO 19
<211> LENGTH: 45
<212> TYPE: DNA
<213> ORGANISM: Artificial Sequence
<220> FEATURE:
<223> OTHER INFORMATION: Primer 67-1E-C for PCR amplification of the
      coding sequence of the ispD gene

<400> SEQUENCE: 19
cataaagggc ccaggaggaa taaatggcaa ccactcattt ggatg                     45

<210> SEQ ID NO 20
<211> LENGTH: 40
<212> TYPE: DNA
<213> ORGANISM: Artificial Sequence
<220> FEATURE:
<223> OTHER INFORMATION: Primer 67-1F-C for PCR amplification of the
      coding sequence of the ispD gene

<400> SEQUENCE: 20
tattgttcat atgttatgta ttctcctgat ggatggttcg                           40

<210> SEQ ID NO 21
<211> LENGTH: 45
<212> TYPE: DNA
<213> ORGANISM: Artificial Sequence
<220> FEATURE:
<223> OTHER INFORMATION: Primer 67-1G-C for PCR amplification of the
      coding sequence of the ispE gene

<400> SEQUENCE: 21
aactaacaca tatgaggagg aataaatgcg gacacagtgg ccctc                     45

<210> SEQ ID NO 22
<211> LENGTH: 38
<212> TYPE: DNA
<213> ORGANISM: Artificial Sequence
<220> FEATURE:
```

<223> OTHER INFORMATION: Primer 67-1H-C for PCR amplification of the
      coding sequence of the ispE gene

<400> SEQUENCE: 22
tgttagttac gcgtttaaag catggctctg tgcaatgg                            38

<210> SEQ ID NO 23
<211> LENGTH: 45
<212> TYPE: DNA
<213> ORGANISM: Artificial Sequence
<220> FEATURE:
<223> OTHER INFORMATION: Primer 67-2A-C for PCR amplification of the
      coding sequence of the ispF gene

<400> SEQUENCE: 23
acgggatcca ggaggaataa atgcgaattg gacacggttt tgacg                    45

<210> SEQ ID NO 24
<211> LENGTH: 41
<212> TYPE: DNA
<213> ORGANISM: Artificial Sequence
<220> FEATURE:
<223> OTHER INFORMATION: Primer 67-2B-C for PCR amplification of the
      coding sequence of the ispF gene

<400> SEQUENCE: 24
tttagttggg ccctcatttt gttgccttaa tgagtagcgc c                        41

<210> SEQ ID NO 25
<211> LENGTH: 49
<212> TYPE: DNA
<213> ORGANISM: Artificial Sequence
<220> FEATURE:
<223> OTHER INFORMATION: Primer 67-2C-C for PCR amplification of the
      coding sequence of the ispG gene

<400> SEQUENCE: 25
tactaagggc ccaggaggaa ataatgcata accaggctcc aattcaacg                49

<210> SEQ ID NO 26
<211> LENGTH: 40
<212> TYPE: DNA
<213> ORGANISM: Artificial Sequence
<220> FEATURE:
<223> OTHER INFORMATION: Primer 67-2D-C for PCR amplification of the
      coding sequence of the ispG gene

<400> SEQUENCE: 26
tccgggtacc ttattttca acctgctgaa cgtcaattcg                           40

<210> SEQ ID NO 27
<211> LENGTH: 43
<212> TYPE: DNA
<213> ORGANISM: Artificial Sequence
<220> FEATURE:
<223> OTHER INFORMATION: Primer 67-2E-C for PCR amplification of the
      coding sequence of the ispH gene

<400> SEQUENCE: 27
aacaggtacc aggaggaaat aatgcagatc ctgttggcca acc                      43

<210> SEQ ID NO 28
<211> LENGTH: 45
<212> TYPE: DNA
<213> ORGANISM: Artificial Sequence
<220> FEATURE:
<223> OTHER INFORMATION: Primer 67-2F-C for PCR amplification of the coding sequence of the ispH gene

<400> SEQUENCE: 28
tggatgaagt cgacttaatc gacttcacga atatcgacac gcagc                    45

<210> SEQ ID NO 29
<211> LENGTH: 50
<212> TYPE: DNA
<213> ORGANISM: Artificial Sequence
<220> FEATURE:
<223> OTHER INFORMATION: Primer 67-2G-C for PCR amplification of the
      coding sequence of the idi gen

<400> SEQUENCE: 29
catcaagtcg acaggaggaa ataatgcaaa cggaacacgt cattttattg               50

<210> SEQ ID NO 30
<211> LENGTH: 40
<212> TYPE: DNA
<213> ORGANISM: Artificial Sequence
<220> FEATURE:
<223> OTHER INFORMATION: Primer 67-2H-C for PCR amplification of the
      coding sequence of the idi gene

<400> SEQUENCE: 30
taatgcaagc ttatttaagc tgggtaaatg cagataatcg                          40

<210> SEQ ID NO 31
<211> LENGTH: 44
<212> TYPE: DNA
<213> ORGANISM: Artificial Sequence
<220> FEATURE:
<223> OTHER INFORMATION: Primer 67-2I-C for PCR amplification of the
      coding sequence of the ispA gene

<400> SEQUENCE: 31
cagtaaagct taggaggaaa taatggactt tccgcagcaa ctcg                     44

<210> SEQ ID NO 32
<211> LENGTH: 41
<212> TYPE: DNA
<213> ORGANISM: Artificial Sequence
<220> FEATURE:
<223> OTHER INFORMATION: Primer 67-2J-C for PCR amplification of the
      coding sequence of the ispA gene

<400> SEQUENCE: 32
tagttccatg gttatttatt acgctggatg atgtagtccg c                        41

<210> SEQ ID NO 33
<211> LENGTH: 35
<212> TYPE: DNA
<213> ORGANISM: Artificial Sequence
<220> FEATURE:
<223> OTHER INFORMATION: Primer 9-156A for PCR amplification of the RK2
      par locus

<400> SEQUENCE: 33
acatagacgt cgggaaagcg aggatctagg taggg                               35

<210> SEQ ID NO 34
<211> LENGTH: 37
<212> TYPE: DNA
<213> ORGANISM: Artificial Sequence
<220> FEATURE:
<223> OTHER INFORMATION: Primer 9-156B for PCR amplification of the RK2
      par locus

<400> SEQUENCE: 34
ttcccgctcg aggtggcgga ccatataggc agatcag      37

<210> SEQ ID NO 35
<211> LENGTH: 23
<212> TYPE: DNA
<213> ORGANISM: Artificial Sequence
<220> FEATURE:
<223> OTHER INFORMATION: Primer 19-137 cml-pAM37-AS

<400> SEQUENCE: 35
gacgtcgata tctggcgaaa atg      23

<210> SEQ ID NO 36
<211> LENGTH: 22
<212> TYPE: DNA
<213> ORGANISM: Artificial Sequence
<220> FEATURE:
<223> OTHER INFORMATION: Primer 19-137 cml-pAM37-S

<400> SEQUENCE: 36
tactagtgct tggattctca cc      22

<210> SEQ ID NO 37
<211> LENGTH: 32
<212> TYPE: DNA
<213> ORGANISM: Artificial Sequence
<220> FEATURE:
<223> OTHER INFORMATION: Primer for PCR amplification of a nucleotide
      sequence encoding a beta-farnesene synthase

<400> SEQUENCE: 37
ccatggacac tctgccgatc tcttccgtaa gc      32

<210> SEQ ID NO 38
<211> LENGTH: 28
<212> TYPE: DNA
<213> ORGANISM: Artificial Sequence
<220> FEATURE:
<223> OTHER INFORMATION: Primer for PCR amplification of a nucleotide
      sequence encoding a beta-farnesene synthase

<400> SEQUENCE: 38
gagctctcat acgaccatag ggtgtacg      28

<210> SEQ ID NO 39
<211> LENGTH: 25
<212> TYPE: DNA
<213> ORGANISM: Artificial Sequence
<220> FEATURE:
<223> OTHER INFORMATION: Primer for PCR amplification of a nucleotide
      sequence encoding an alpha-farnesene synthase

<400> SEQUENCE: 39
ccatggacct ggcagtagaa attgc      25

<210> SEQ ID NO 40
<211> LENGTH: 27
<212> TYPE: DNA
<213> ORGANISM: Artificial Sequence
<220> FEATURE:
<223> OTHER INFORMATION: Primer for PCR amplification of a nucleotide
      sequence encoding an alpha-farnesene synthase

<400> SEQUENCE: 40

```
gagctcttac atcggtaccg gctccag                                           27
```

<210> SEQ ID NO 41
<211> LENGTH: 3978
<212> TYPE: DNA
<213> ORGANISM: Artificial Sequence
<220> FEATURE:
<223> OTHER INFORMATION: atoB(opt):HMGS(opt):mvaA operon

<400> SEQUENCE: 41

```
atgaagaact gtgtgattgt ttctgcggtc cgcacggcga tcggcagctt taacggctct     60
ttagcgagca cctctgcaat cgatctgggt gcgacggtca ttaaggccgc cattgaacgc    120
gccaaaatcg acagccagca cgttgatgag gtgatcatgg caatgtgtt acaagccggc     180
ctgggtcaaa acccagcgcg tcaagcactg ttaaaatctg gtctggccga gaccgtgtgt    240
ggcttcaccg tcaataaggt ttgcggctct ggcctgaaga gcgtggccct ggcagcacaa    300
gcgattcaag ccggtcaggc acaaagcatc gttgcgggtg catggagaa catgtctctg    360
gcgccgtact tattagatgc caaagcccgc agcggttatc gcctgggcga tggtcaggtg    420
tacgacgtca tcttacgcga tggcttaatg tgcgcgaccc acggttacca catgggtatt    480
acggccgaaa acgtggcgaa agaatacggc attacgcgcg agatgcagga tgaattagca    540
ctgcactctc agcgcaaagc agcagccgcg atcgagtctg gtgcgtttac ggcggaaatc    600
gtgccagtta acgtggtcac gcgcaagaag acgttcgttt tcagccagga cgagttcccg    660
aaggcaaaca gcaccgcgga ggccttaggt gccttacgcc cagcctttga caaagcgggc    720
acggtcaccg ccggtaatgc gagcggcatc aatgatggtg cagcggcact ggtcatcatg    780
gaagagagcg ccgcattagc agcgggtctg accccattag cgcgcattaa atcttatgcc    840
agcggcggc tcccaccagc cctgatgggc atgggtccgg tcccagccac gcaaaaagcc    900
ctgcaattag cgggcctgca actggccgac attgatctga tcgaggcgaa cgaggcgttt    960
gcagcgcagt tcctggcggt gggtaagaat ctgggcttcg acagcgagaa agtcaatgtg   1020
aacggtggcg cgattgcgtt aggccatccg attggtgcaa gcggcgcacg catcttagtg   1080
acgttactgc acgccatgca ggcacgcgac aagaccttag gcctggcgac cttatgtatt   1140
ggtggcggtc aaggtatcgc catggtgatc gaacgcctga ctgaagatc taggaggaaa   1200
gcaaaatgaa actgagcacc aagctgtgct ggtgtggcat caagggtcgc ctgcgcccac   1260
aaaagcagca acagctgcac aacacgaacc tgcaaatgac cgagctgaaa aagcagaaga   1320
cggccgagca aaagacccgc ccgcagaacg ttggcatcaa gggcatccag atttatatcc   1380
cgacgcagtg tgtcaaccaa tctgagctgg agaaattcga tggcgtcagc cagggtaagt   1440
acaccatcgg cctgggccag accaacatga gcttcgtgaa cgaccgtgag gacatctatt   1500
ctatgagcct gacggtgctg tctaagctga tcaagagcta acatcgac acgaataaga   1560
tcggtcgtct ggaggtgggt acggagacgc tgattgacaa gagcaaaagc gtgaagtctg   1620
tcttaatgca gctgttcggc gagaacacgg atgtcgaggg tatcgacacc ctgaacgcgt   1680
gttacggcgg caccaacgca ctgttcaata gcctgaactg gattgagagc aacgcctggg   1740
atggccgcga tgcgatcgtc gtgtgcgcg atatcgccat ctatgacaag ggtgcggcac   1800
gtccgaccgg cggtgcaggc accgttgcga tgtggattgg cccggacgca ccaattgtct   1860
tcgattctgt ccgcgcgtct acatggagc acgcctacga cttttacaag ccggacttca   1920
cgagcgaata cccgtacgtg gacggccact tctctctgac ctgctatgtg aaggcgctgg   1980
accaggttta taagtcttat agcaaaaagg cgatttctaa gggcctggtc agcgaccccg   2040
```

```
caggcagcga cgccctgaac gtgctgaagt atttcgacta caacgtgttc catgtcccga    2100
cctgcaaatt agtgaccaaa tcttatggcc gcctgttata taatgatttc cgtgccaacc    2160
cgcagctgtt cccggaggtt gacgccgagc tggcgacgcg tgattacgac gagagcctga    2220
ccgacaagaa catcgagaag accttcgtca acgtcgcgaa gccgttccac aaagagcgtg    2280
tggcccaaag cctgatcgtc ccgaccaaca cgggcaacat gtataccgcg tctgtctacg    2340
cggcattcgc gagcctgctg aattacgtcg gttctgacga cctgcagggc aagcgcgttg    2400
gcctgttcag ctacggtagc ggcttagcgg ccagcctgta tagctgcaaa attgtcggcg    2460
acgtccagca tcatcaag gagctggaca tcaccaacaa gctggcgaag cgcatcaccg    2520
agacgccgaa agattacgag gcagcgatcg agttacgcga gaatgcgcat ctgaagaaga    2580
acttcaagcc gcaaggtagc atcgagcacc tgcagagcgg cgtctactac ctgacgaaca    2640
ttgacgacaa gttccgccgt tcttatgacg tcaaaaagta actagtagga ggaaaacatc    2700
atgcaaagtt tagataagaa tttccgacat ttatctcgtc aacaaaagtt acaacaattg    2760
gtagataagc aatggttatc agaagatcaa ttcgacattt tattgaatca tccattaatt    2820
gatgaggaag tagcaaatag tttaattgaa aatgtcatcg cgcaaggtgc attacccgtt    2880
ggattattac cgaatatcat tgtggacgat aaggcatatg ttgtacctat gatggtggaa    2940
gagccttcag ttgtcgctgc agctagttat ggtgcaaagc tagtgaatca gactggcgga    3000
tttaaaacgg tatcttctga acgtattatg ataggtcaaa tcgtctttga tggcgttgac    3060
gatactgaaa aattatcagc agacattaaa gctttagaaa agcaaattca taaaattgcg    3120
gatgaggcat atccttctat taaagcgcgt ggtggtggtt accaacgtat agctattgat    3180
acatttcctg agcaacagtt actatcttta aaagtatttg ttgatacgaa agatgctatg    3240
ggcgctaata tgcttaatac gatttagag gccataactg catttttaaa aaatgaatct    3300
ccacaaagcg acatttaat gagtatttta tccaatcatg caacagcgtc cgttgttaaa    3360
gttcaaggcg aaattgacgt taaagattta gcaaggggcg agagaactgg agaagaggtt    3420
gccaaacgaa tggaacgtgc ttctgtattg gcacaagttg atattcatcg tgctgcaaca    3480
cataataaag gtgttatgaa tggcatacat gccgttgttt tagcaacagg aaatgatacg    3540
cgtggtgcag aagcaagtgc gcatgcatac gcgagtcgtg acggacagta tcgtggtatt    3600
gcaacatgga gatacgatca aaaacgtcaa cgtttaattg gtacaataga agtgcctatg    3660
acattggcaa tcgttggcgg tggtacaaaa gtattaccaa ttgctaaagc ttctttagaa    3720
ttgctaaatg tagattcagc acaagaatta ggtcatgtag ttgctgccgt tggtttagca    3780
cagaactttg cagcatgtcg cgcgctcgtt tccgaaggta tccagcaagg ccatatgagc    3840
ttgcaatata aatctttagc tattgttgta ggtgcaaaag gtgatgaaat tgcgcaagta    3900
gctgaagcat tgaagcaaga accccgtgcg aatacacaag tagctgaacg catttacaa    3960 gaaattagac aacaatag                                                  3978
```

<210> SEQ ID NO 42  
<211> LENGTH: 3669  
<212> TYPE: DNA  
<213> ORGANISM: Artificial Sequence  
<220> FEATURE:  
<223> OTHER INFORMATION: atoB(opt):mvaS(opt):mvaA operon

<400> SEQUENCE: 42

```
atgaagaact gtgtgattgt ttctgcggtc cgcacggcga tcggcagctt taacggctct    60
```

```
ttagcgagca cctctgcaat cgatctgggt gcgacggtca ttaaggccgc cattgaacgc    120
gccaaaatcg acagccagca cgttgatgag gtgatcatgg gcaatgtgtt acaagccggc    180
ctgggtcaaa acccagcgcg tcaagcactg ttaaaatctg gtctggccga gaccgtgtgt    240
ggcttcaccg tcaataaggt ttgcggctct ggcctgaaga gcgtggccct ggcagcacaa    300
gcgattcaag ccggtcaggc acaaagcatc gttgcgggtg gcatggagaa catgtctctg    360
gcgccgtact tattagatgc caaagcccgc agcggttatc gcctgggcga tggtcaggtg    420
tacgacgtca tcttacgcga tggcttaatg tgcgcgaccc acggttacca catgggtatt    480
acggccgaaa acgtggcgaa agaatacggc attacgcgcg agatgcagga tgaattagca    540
ctgcactctc agcgcaaagc agcagccgcg atcgagtctg gtgcgtttac ggcggaaatc    600
gtgccagtta acgtggtcac gcgcaagaag acgttcgttt tcagccagga cgagttcccg    660
aaggcaaaca gcaccgcgga ggccttaggt gccttacgcc cagcctttga caaagcgggc    720
acggtcaccg ccggtaatgc gagcggcatc aatgatggtg cagcggcact ggtcatcatg    780
gaagagagcg ccgcattagc agcgggtctg accccattag cgcgcattaa atcttatgcc    840
agcggcggcg tcccaccagc cctgatgggc atgggtccgg tcccagccac gcaaaaagcc    900
ctgcaattag cgggcctgca actggccgac attgatctga tcgaggcgaa cgaggcgttt    960
gcagcgcagt tcctggcggt gggtaagaat ctgggcttcg acagcgagaa agtcaatgtg    1020
aacggtggcg cgattgcgtt aggccatccg attggtgcaa gcggcgcacg catcttagtg    1080
acgttactgc acgccatgca ggcacgcgac aagaccttag gcctggcgac cttatgtatt    1140
ggtggcggtc aaggtatcgc catggtgatc gaacgcctga actgaagatc taggaggaaa    1200
gcaaaatgac aataggtatc gacaaaataa acttttacgt tccaaagtac tatgtagaca    1260
tggctaaatt agcagaagca cgccaagtag acccaaacaa atttttaatt ggaattggtc    1320
aaactgaaat ggctgttagt cctgtaaacc aagacatcgt ttcaatgggc gctaacgctg    1380
ctaaggacat tataacagac gaagataaaa agaaaattgg tatggtaatt gtggcaactg    1440
aatcagcagt tgatgctgct aaagcagccg ctgttcaaat tcacaactta ttaggtattc    1500
aaccttttgc acgttgcttt gaaatgaaag aagcttgtta tgctgcaaca ccagcaattc    1560
aattagctaa agattattta gcaactagac gaatgaaaaa agtattagtt attgctacag    1620
atacagcacg ttatgattg aattcaggcg gcgagccaac acaaggtgct ggcgcagttg    1680
cgatggttat tgcacataat ccaagcattt tggcattaaa tgaagatgct gttgcttaca    1740
ctgaagacgt ttatgatttc tggcgtccaa ctggacataa atatccatta gttgatggtg    1800
cattatctaa agatgcttat atccgctcat tccaacaaag ctggaatgaa tacgcaaaac    1860
gtcaaggtaa gtcgctagct gacttcgcat ctctatgctt ccatgttcca tttacaaaaa    1920
tgggtaaaaa ggcattagag tcaatcattg ataacgctga tgaaacaact caagagcgtt    1980
tacgttcagg atatgaagat gctgtagatt ataaccgtta tgtcggtaat atttatactg    2040
gatcattata tttaagccta atatcattac ttgaaaatcg tgatttacaa gctggtgaaa    2100
caatcggttt attcagttat ggctcaggtt cagttggtga attttatagt gcgacattag    2160
ttgaaggcta caaagatcat ttagatcaag ctgcacataa agcattatta ataaccgta    2220 ctgaagtatc tgttgatgca tatgaaacat tcttcaaacg ttttgatgac gttgaatttg    2280
acgaagaaca agatgctgtt catgaagatc gtcatatttt ctacttatca aatattgaaa    2340
ataacgttcg cgaatatcac agaccagagt aactagtagg aggaaaacat catgcaaagt    2400
ttagataaga atttccgaca tttatctcgt caacaaaagt tacaacaatt ggtagataag    2460
```

-continued

```
caatggttat cagaagatca attcgacatt ttattgaatc atccattaat tgatgaggaa    2520
gtagcaaata gtttaattga aaatgtcatc gcgcaaggtg cattacccgt tggattatta    2580
ccgaatatca ttgtggacga taaggcatat gttgtaccta tgatggtgga agagccttca    2640
gttgtcgctg cagctagtta tggtgcaaag ctagtgaatc agactggcgg atttaaaacg    2700
gtatcttctg aacgtattat gataggtcaa atcgtctttg atggcgttga cgatactgaa    2760
aaattatcag cagacattaa agctttagaa aagcaaattc ataaaattgc ggatgaggca    2820
tatccttcta ttaaagcgcg tggtggtggt taccaacgta tagctattga tacatttcct    2880
gagcaacagt tactatcttt aaaagtattt gttgatacga agatgctat gggcgctaat     2940 atgcttaata cgattttaga ggccataact gcattttaa aaaatgaatc tccacaaagc     3000
gacattttaa tgagtatttt atccaatcat gcaacagcgt ccgttgttaa agttcaaggc    3060
gaaattgacg ttaaagattt agcaaggggc gagagaactg agaagaggt tgccaaacga     3120 atggaacgtg cttctgtatt ggcacaagtt gatattcatc gtgctgcaac acataataaa    3180
ggtgttatga atggcataca tgccgttgtt ttagcaacag gaaatgatac gcgtggtgca    3240
gaagcaagtc gcatgcata cgcgagtcgt gacggacagt atcgtggtat tgcaacatgg     3300
agatacgatc aaaaacgtca acgtttaatt ggtacaatag aagtgcctat gacattggca    3360
atcgttggcg gtggtacaaa agtattacca attgctaaag cttctttaga attgctaaat    3420
gtagattcag cacaagaatt aggtcatgta gttgctgccg ttggtttagc acagaacttt    3480
gcagcatgtc gcgcgctcgt ttccgaaggt atccagcaag gccatatgag cttgcaatat    3540
aaatctttag ctattgttgt aggtgcaaaa ggtgatgaaa ttgcgcaagt agctgaagca    3600
ttgaagcaag aacccgtgc gaatacacaa gtagctgaac gcattttaca agaaattaga    3660
caacaatag                                                           3669
```

<210> SEQ ID NO 43
<211> LENGTH: 2235
<212> TYPE: DNA
<213> ORGANISM: Artificial Sequence
<220> FEATURE:
<223> OTHER INFORMATION: pAM328 - ERG9-KANMX-MET3promoter-ERG9
      (excluding vector backbone)

<400> SEQUENCE: 43

```
caataccgac ttaccatcct atttgctttg cccttttttct tttccactgc atggcggcgt      60
tagtatcgaa tggatggcgg cgttagtatc gaatcgacag cagtatagcg accagcattc     120
acatacgatt gacgcatgat attactttct gcgcacttaa cttcgcatct gggcagatga     180
tgtcgaggcg aaaaaaaata taaatcacgc taacatttga ttaaaataga acaactacaa     240
tataaaaaaa ctatacaaat gacaagttct tgaaaacaag aatctttta ttgtcagtac      300 tgattagaaa aactcatcga gcatcaaatg aaactgcaat ttattcatat caggattatc     360
aataccatat ttttgaaaaa gccgtttctg taatgaagga gaaaactcac cgaggcagtt     420
ccataggatg gcaagatcct ggtatcggtc tgcgattccg actcgtccaa catcaataca    480
acctattaat ttcccctcgt caaaaataag gttatcaagt gagaaatcac catgagtgac    540
gactgaatcc ggtgagaatg gcaaaagctt atgcatttct ttccagactt gttcaacagg    600
ccagccatta cgctcgtcat caaaatcact cgcatcaacc aaaccgttat tcattcgtga    660
ttgcgcctga gcgagacgaa atacgcgatc gctgttaaaa ggacaattac aaacaggaat    720
cgaatgcaac cggcgcagga acactgccag cgcatcaaca atattttcac ctgaatcagg    780
```

```
atattcttct aataccggga atgctgtttt gccggggatc gcagtggtga gtaaccatgc    840
atcatcagga gtacggataa aatgcttgat ggtcggaaga ggcataaatt ccgtcagcca    900
gtttagtctg accatctcat ctgtaacatc attggcaacg ctacctttgc catgtttcag    960
aaacaactct ggcgcatcgg gcttcccata caatcgatag attgtcgcac ctgattgccc   1020
gacattatcg cgagcccatt tatacccata taaatcagca tccatgttgg aatttaatcg   1080
cggcctcgaa acgtgagtct tttccttacc catggttgtt tatgttcgga tgtgatgtga   1140
gaactgtatc ctagcaagat tttaaaagga agtatatgaa agaagaacct cagtggcaaa   1200
tcctaacctt ttatatttct ctacaggggc gcggcgtggg gacaattcaa cgcgtctgtg   1260
aggggagcgt ttccctgctc gcaggtctgc agcgaggagc cgtaattttt gcttcgcgcc   1320
gtgcggccat caaatgtat ggatgcaaat gattatacat ggggatgtat gggctaaatg   1380
tacgggcgac agtcacatca tgcccctgag ctgcgcacgt caagactgtc aaggagggta   1440
ttctgggcct ccatgtcgct ggccgggtga cccggcgggg acgaggcaag ctaaacagat   1500
ctgatcttga aactgagtaa gatgctcaga atacccgtca agataagagt ataatgtaga   1560
gtaatatacc aagtattcag catattctcc tcttcttttg tataaatcac ggaagggatg   1620
atttataaga aaatgaata ctattacact tcatttacca ccctctgatc tagattttcc   1680
aacgatatgt acgtagtggt ataaggtgag ggggtccaca gatataacat cgtttaattt   1740
agtactaaca gagactttg tcacaactac atataagtgt acaaatatag tacagatatg   1800
acacacttgt agcgccaacg cgcatcctac ggattgctga cagaaaaaaa ggtcacgtga   1860
ccagaaaagt cacgtgtaat tttgtaactc accgcattct agcggtccct gtcgtgcaca   1920
ctgcactcaa caccataaac cttagcaacc tccaaaggaa atcaccgtat aacaaagcca   1980
cagttttaca acttagtctc ttatgaagtt acttaccaat gagaaataga ggctctttct   2040
cgagaaatat gaatatggat atatatatat atatatatat atatatatat atatgtaaac   2100
ttggttcttt tttagcttgt gatctctagc ttgggtctct ctctgtcgta acagttgtga   2160
tatcggctgc cttcatctcg accggatgca atgccaattg taatagcttt cccatgttaa   2220
ttatacttta ttctt                                                   2235

<210> SEQ ID NO 44
<211> LENGTH: 66
<212> TYPE: DNA
<213> ORGANISM: Artificial Sequence
<220> FEATURE:
<223> OTHER INFORMATION: primers 50-56-pw100-G

<400> SEQUENCE: 44
gagtgaacct gctgcctggc gtgctctgac tcagtacatt tcatagtgga tggcggcgtt    60
agtatc                                                              66

<210> SEQ ID NO 45
<211> LENGTH: 65
<212> TYPE: DNA
<213> ORGANISM: Artificial Sequence
<220> FEATURE:
<223> OTHER INFORMATION: primers 50-56-pw101-G

<400> SEQUENCE: 45
cgtgtatacg ttttccgctt ctgctcttcg tcttttctct tcttccgata tcacaactgt    60
tacga                                                               65
```

<210> SEQ ID NO 46
<211> LENGTH: 70
<212> TYPE: DNA
<213> ORGANISM: Artificial Sequence
<220> FEATURE:
<223> OTHER INFORMATION: primers 61-67-CPK066-G

<400> SEQUENCE: 46

```
ggtaagacgg ttgggtttta tcttttgcag ttggtactat taagaacaat cacaggaaac   60
agctatgacc                                                          70
```

<210> SEQ ID NO 47
<211> LENGTH: 70
<212> TYPE: DNA
<213> ORGANISM: Artificial Sequence
<220> FEATURE:
<223> OTHER INFORMATION: primers 61-67-CPK067-G

<400> SEQUENCE: 47

```
ttgcgttttg tactttggtt cgctcaattt tgcaggtaga taatcgaaaa gttgtaaaac   60
gacggccagt                                                          70
```

<210> SEQ ID NO 48
<211> LENGTH: 5487
<212> TYPE: DNA
<213> ORGANISM: Artificial Sequence
<220> FEATURE:
<223> OTHER INFORMATION: pAM491 sequence (excluding vector backbone)

<400> SEQUENCE: 48

```
gtttaaactt gctaaattcg agtgaaacac aggaagacca gaaaatcctc atttcatcca   60
tattaacaat aatttcaaat gtttatttgc attatttgaa actagggaag acaagcaacg  120
aaacgttttg aaaattttga gtattttcaa taaatttgta gaggactcag atattgaaaa  180
aaagctacag caattaatac ttgataagaa gagtattgag aagggcaacg gttcatcatc  240
tcatggatct gcacatgaac aaacaccaga gtcaaacgac gttgaaattg aggctactgc  300
gccaattgat gacaatacag acgatgataa caaaccgaag ttatctgatg tagaaaagga  360
ttaaagatgc taagagatag tgatgatatt tcataaataa tgtaattcta tatatgttaa  420 ttacctttt tgcgaggcat atttatggtg aaggataagt tttgaccatc aaagaaggtt  480
aatgtggctg tggtttcagg gtccataccc gggagttatg acaattacaa caacagaatt  540
ctttctatat atgcacgaac ttgtaatatg gaagaaatta tgacgtacaa actataaagt  600
aaatatttta cgtaacacat ggtgctgttg tgcttctttt tcaagagaat accaatgacg  660
tatgactaag tttaggattt aatgcaggtg acggacccat ctttcaaacg atttatatca  720
gtggcgtcca aattgttagg ttttgttggt tcagcaggtt tcctgttgtg ggtcatatga  780
ctttgaacca aatggccggc tgctagggca gcacataagg ataattcacc tgccaagacg  840
gcacaggcaa ctattcttgc taattgacgt gcgttggtac caggagcggt agcatgtggg  900
cctcttacac ctaataagtc caacatggca ccttgtggtt ctagaacagt accaccaccg  960
atggtaccta cttcgatgga tggcatggat acgaaattc tcaaatcacc gtccacttct 1020
ttcatcaatg ttatacagtt ggaactttcg acattttgtg caggatcttg tcctaatgcc 1080
aagaaaacag ctgtcactaa attagctgca tgtgcgttaa atccaccaac agacccagcc 1140
attgcagatc caaccaaatt cttagcaatg ttcaactcaa ccaatgcgga aacatcactt 1200
tttaacactt ttctgacaac atcaccagga atagtagctt ctgcgacgac actcttacca 1260
```

```
cgaccttcga tccagttgat ggcagctggt tttttgtcgg tacagtagtt accagaaacg    1320
gagacaacct ccatatcttc ccagccatac tcttctacca tttgctttaa tgagtattcg    1380
acacccttag aaatcatatt catacccatt gcgtcaccag tagttgttct aaatctcatg    1440
aagagtaaat ctcctgctag acaagtttga atatgttgca gacgtgcaaa tcttgatgta    1500
gagttaaaag cttttttaat tgcgttttgt ccctcttctg agtctaacca tatcttacag    1560
gcaccagatc ttttcaaagt tgggaaacgg actactgggc tcttgtcat accatcctta     1620 gttaaaacag ttgttgcacc accgccagca ttgattgcct tacagccacg catggcagaa    1680
gctaccaaac aaccctctgt agttgccatt ggtatatgat aagatgtacc atcgataacc    1740
aaggggccta taacaccaac gggcaaaggc atgtaaccta aacattttc acaacaagcg     1800 ccaaatacgc ggtcgtagtc ataatttta tatggtaaac gatcagatgc taatacagga     1860
gcttctgcca aaattgaaag agccttccta cgtaccgcaa ccgctctcgt agtatcacct    1920 aatttttct ccaaagcgta caaggtaac ttaccgtgaa taaccaaggc agcgacctct       1980
ttgttcttca attgttttgt atttccacta cttaataatg cttctaattc ttctaaagga    2040
cgtattttct tatccaagct ttcaatatcg cgggaatcat cttcctcact agatgatgaa    2100
ggtcctgatg agctcgattg cgcagatgat aaacttttga ctttcgatcc agaaatgact    2160
gttttattgg ttaaaactgg tgtagaagcc ttttgtacag gagcagtaaa agacttcttg    2220
gtgacttcag tcttcaccaa ttggtctgca gccattatag ttttttctcc ttgacgttaa    2280
agtatagagg tatattaaca attttttgtt gatacttta tgacatttga ataagaagta     2340
atacaaaccg aaaatgttga agtattagt taaagtggtt atgcagcttt tgcatttata     2400
tatctgttaa tagatcaaaa atcatcgctt cgctgattaa ttaccccaga aataaggcta    2460
aaaaactaat cgcattatta tcctatggtt gttaatttga ttcgttgatt tgaaggtttg    2520
tggggccagg ttactgccaa ttttttcctct tcataaccat aaaagctagt attgtagaat   2580
ctttattgtt cggagcagtg cggcgcgagg cacatctgcg tttcaggaac gcgaccggtg    2640
aagaccagga cgcacggagg agagtcttcc gtcggagggc tgtcgcccgc tcggcggctt    2700
ctaatccgta cttcaatata gcaatgagca gttaagcgta ttactgaaag ttccaaagag    2760
aaggtttttt taggctaaga taatggggct ctttacattt ccacaacata taagtaagat    2820
tagatatgga tatgtatatg gtggtattgc catgtaatat gattattaaa cttctttgcg    2880
tccatccaaa aaaaagtaa gaattttga aaattcaata taaatgaaac tctcaactaa      2940
actttgttgg tgtggtatta aaggaagact taggccgcaa aagcaacaac aattacacaa    3000
tacaaacttg caaatgactg aactaaaaaa acaaagacc gctgaacaaa aaccagacc      3060 tcaaaatgtc ggtattaaag gtatccaaat ttacatccca actcaatgtg tcaaccaatc    3120
tgagctagag aaatttgatg gcgtttctca aggtaaatac acaattggtc tgggccaaac    3180
caacatgtct tttgtcaatg acagagaaga tatctactcg atgtccctaa ctgttttgtc    3240
taagttgatc aagagttaca acatcgacac caacaaaatt ggtagattag aagtcggtac    3300
tgaaactctg attgacaagt ccaagtctgt caagtctgtc ttgatgcaat gtttggtga    3360 aaacactgac gtcgaaggta ttgacacgct taatgcctgt tacggtggta ccaacgcgtt    3420
gttcaactct tgaactgga ttgaatctaa cgcatgggat ggtagagacg ccattgtagt     3480
ttgcggtgat attgccatct acgataaggg tgccgcaaga ccaaccggtg gtgccggtac    3540
tgttgctatg tggatcggtc ctgatgctcc aattgtattt gactctgtaa gagcttctta    3600
```

```
catggaacac gcctacgatt tttacaagcc agatttcacc agcgaatatc cttacgtcga   3660
tggtcatttt tcattaactt gttacgtcaa ggctcttgat caagtttaca agagttattc   3720
caagaaggct atttctaaag ggttggttag cgatcccgct ggttcggatg ctttgaacgt   3780
tttgaaatat ttcgactaca acgttttcca tgttccaacc tgtaaattgg tcacaaaatc   3840
atacggtaga ttactatata acgatttcag agccaatcct caattgttcc cagaagttga   3900
cgccgaatta gctactcgcg attatgacga atctttaacc gataagaaca ttgaaaaaac   3960
ttttgttaat gttgctaagc cattccacaa agagagagtt gcccaatctt tgattgttcc   4020
aacaaacaca ggtaacatgt acaccgcatc tgtttatgcc gcctttgcat ctctattaaa   4080
ctatgttgga tctgacgact acaaggcaa gcgtgttggt ttattttctt acggttccgg   4140
tttagctgca tctctatatt cttgcaaaat tgttggtgac gtccaacata ttatcaagga   4200
attagatatt actaacaaat tagccaagag aatcaccgaa actccaaagg attacgaagc   4260
tgccatcgaa ttgagagaaa atgcccattt gaagaagaac ttcaaacctc aaggttccat   4320
tgagcatttg caaagtggtg tttactactt gaccaacatc gatgacaaat ttagaagatc   4380
ttacgatgtt aaaaaataat cttcccccat cgattgcatc ttgctgaacc cccttcataa   4440
atgctttatt tttttggcag cctgcttttt ttagctctca tttaatagag tagttttta   4500 atctatatac taggaaaact ctttatttaa taacaatgat atatatatac ccgggaagct   4560
tttcaattca tcttttttt ttttgttctt ttttttgatt ccggtttctt tgaaattttt   4620
ttgattcggt aatctccgag cagaaggaag aacgaaggaa ggagcacaga cttagattgg   4680
tatatatacg catatgtggt gttgaagaaa catgaaattg cccagtattc ttaacccaac   4740
tgcacagaac aaaaacctgc aggaaacgaa gataaatcat gtcgaaagct acatataagg   4800
aacgtgctgc tactcatcct agtcctgttg ctgccaagct attaatatc atgcacgaaa   4860 agcaaacaaa cttgtgtgct tcattggatg ttcgtaccac caaggaatta ctggagttag   4920
ttgaagcatt aggtcccaaa atttgtttac taaaaacaca tgtggatatc ttgactgatt   4980
tttccatgga gggcacagtt aagccgctaa aggcattatc cgccaagtac aattttttac   5040
tcttcgaaga cagaaaattt gctgacattg gtaatacagt caaattgcag tactctgcgg   5100
gtgtatacag aatagcagaa tgggcagaca ttacgaatgc acacggtgtg gtgggcccag   5160
gtattgttag cggtttgaag caggcggcgg aagaagtaac aaaggaacct agaggccttt   5220
tgatgttagc agaattgtca tgcaagggct ccctagctac tggagaatat actaagggta   5280
ctgttgacat tgcgaagagc gacaaagatt ttgttatcgg ctttattgct caaagagaca   5340
tgggtggaag agatgaaggt tacgattggt tgattatgac acccggtgtg ggtttagatg   5400
acaagggaga cgcattgggt caacagtata gaaccgtgga tgatgtggtc tctacaggat   5460
ctgacattat tattgttggg tttaaac   5487
```

<210> SEQ ID NO 49
<211> LENGTH: 5860
<212> TYPE: DNA
<213> ORGANISM: Artificial Sequence
<220> FEATURE:
<223> OTHER INFORMATION: pAM492 sequence (excluding vector backbone)

<400> SEQUENCE: 49

```
gtttaaactt gctaaattcg agtgaaacac aggaagacca gaaatcctc atttcatcca     60 tattaacaat aatttcaaat gtttatttgc attatttgaa actagggaag acaagcaacg   120
aaacgttttt gaaaattttg agtattttca ataaatttgt agaggactca gatattgaaa   180
```

```
aaaagctaca gcaattaata cttgataaga agagtattga gaagggcaac ggttcatcat      240
ctcatggatc tgcacatgaa caaacaccag agtcaaacga cgttgaaatt gaggctactg      300
cgccaattga tgacaataca gacgatgata acaaaccgaa gttatctgat gtagaaaagg      360
attaaagatg ctaagagata gtgatgatat ttcataaata atgtaattct atatatgtta      420
attacctttt ttgcgaggca tatttatggt gaaggataag ttttgaccat caagaaggt       480 taatgtggct gtggtttcag ggtccatacc cgggtatata tatcattg ttattaaata        540 aagagttttc ctagtatata gattaaaaaa ctactctatt aaatgagagc taaaaaaagc      600
aggctgccaa aaaaataaag catttatgaa gggggttcag caagatgcaa tcgatgggg       660 aagattattt tttaacatcg taagatcttc taaatttgtc atcgatgttg gtcaagtagt      720
aaacaccact ttgcaaatgc tcaatggaac cttgaggttt gaagttcttc ttcaaatggg      780
cattttctct caattcgatg gcagcttcgt aatcctttgg agtttcggtg attctcttgg      840
ctaatttgtt agtaatatct aattccttga taatatgttg gacgtcacca acaattttgc      900
aagaatatag agatgcagct aaaccggaac cgtaagaaaa taaaccaaca cgcttgcctt      960
gtaagtcgtc agatccaaca tagtttaata gagatgcaaa ggcggcataa acagatgcgg     1020
tgtacatgtt acctgtgttt gttggaacaa tcaaagattg ggcaactctc tctttgtgga     1080
atggcttagc aacattaaca aaagtttttt caatgttctt atcggttaaa gattcgtcat     1140
aatcgcgagt agctaattcg gcgtcaactt ctgggaacaa ttgaggattg gctctgaaat     1200
cgttatatag taatctaccg tatgattttg tgaccaattt acaggttgga acatggaaaa     1260
cgttgtagtc gaaatatttc aaaacgttca aagcatccga accagcggga tcgctaacca     1320 acccttttaga aatagccttc ttggaataac tcttgtaaac ttgatcaaga gccttgacgt     1380
aacaagttaa tgaaaaatga ccatcgacgt aaggatattc gctggtgaaa tctggcttgt     1440
aaaaatcgta ggcgtgttcc atgtaagaag ctcttacaga gtcaaataca attggagcat     1500
caggaccgat ccacatagca acagtaccgg caccaccggt tggtcttgcg gcacccttat     1560
cgtagatggc aatatcaccg caaactacaa tggcgtctct accatcccat gcgttagatt     1620
caatccagtt caaagagttg aacaacgcgt tggtaccacc gtaacaggca ttaagcgtgt     1680
caataccttc gacgtcagtg ttttcaccaa acaattgcat caagacagac ttgacagact     1740
tggacttgtc aatcagagtt tcagtaccga cttctaatct accaattttg ttggtgtcga     1800
tgttgtaact cttgatcaac ttagacaaaa cagttaggga catcgagtag atatcttctc     1860
tgtcattgac aaaagacatg ttggtttggc ccagaccaat tgtgtattta ccttgagaaa     1920
cgccatcaaa tttctctagc tcagattggt tgacacattg agttgggatg taaatttgga     1980
tacctttaat accgacattt tgaggtctgg ttttttgttc agcggtcttt tgttttttta     2040
gttcagtcat ttgcaagttt gtattgtgta attgttgttg cttttgcggc taagtcttc      2100 ctttaatacc acaccaacaa agtttagttg agagtttcat tttatgtgat gattgattga     2160
ttgattgtac agtttgtttt tcttaatatc tatttcgatg acttctatat gatattgcac     2220
taacaagaag atattataat gcaattgata caagacaagg agttattgc ttctcttta       2280 tatgattctg acaatccata ttgcgttggt agtctttttt gctggaacgg ttcagcggaa     2340
aagacgcatc gctctttttg cttctagaag aaatgccagc aaaagaatct cttgacagtg     2400
actgacagca aaaatgtctt tttctaacta gtaacaaggc taagatatca gcctgaaata     2460
aagggtggtg aagtaataat taaatcatcc gtataaacct atacacatat atgaggaaaa     2520
```

```
ataatacaaa agtgttttaa atacagatac atacatgaac atatgcacgt atagcgccca    2580
aatgtcggta atgggatcgg cttactaatt ataaaatgca tcatagaaat cgttgaagtt    2640
gacgcagcga ctcgagatcc ataggagcaa ctcatgtctg aacttcaacg atttctatga    2700
tgcattttat aattagtaag ccgatcccat taccgacatt tgggcgctat acgtgcatat    2760
gttcatgtat gtatctgtat ttaaaacact tttgtattat ttttcctcat atatgtgtat    2820
aggtttatac ggatgattta attattactt caccacccct tatttcaggc tgatatctta    2880
gccttgttac tagttagaaa aagacatttt tgctgtcagt cactgtcaag agattctttt    2940
gctggcattt cttctagaag caaaaagagc gatgcgtctt ttccgctgaa ccgttccagc    3000
aaaaaagact accaacgcaa tatggattgt cagaatcata taaaagagaa gcaaataact    3060
ccttgtcttg tatcaattgc attataatat cttcttgtta gtgcaatatc atatagaagt    3120
catcgaaata gatattaaga aaaacaaact gtacaatcaa tcaatcaatc atcacataaa    3180
atggctgcag accaattggt gaagactgaa gtcaccaaga agtcttttac tgctcctgta    3240
caaaaggctt ctacaccagt tttaaccaat aaaacagtca tttctggatc gaaagtcaaa    3300
agtttatcat ctgcgcaatc gagctcatca ggaccttcat catctagtga ggaagatgat    3360
tcccgcgata ttgaaagctt ggataagaaa atacgtcctt tagaagaatt agaagcatta    3420
ttaagtagtg gaaatacaaa acaattgaag aacaaagagg tcgctgcctt ggttattcac    3480
ggtaagttac ctttgtacgc tttggagaaa aaattaggtg atactacgag agcggttgcg    3540
gtacgtagga aggctctttc aattttggca gaagctcctg tattagcatc tgatcgttta    3600
ccatataaaa attatgacta cgaccgcgta tttggcgctt gttgtgaaaa tgttataggt    3660
tacatgcctt tgcccgttgg tgttataggc cccttggtta tcgatggtac atcttatcat    3720
ataccaatgg caactacaga gggttgtttg gtagcttctg ccatgcgtgg ctgtaaggca    3780
atcaatgctg gcggtggtgc aacaactgtt ttaactaagg atggtatgac aagaggccca    3840
gtagtccgtt tcccaacttt gaaaagatct ggtgcctgta agatatggtt agactcagaa    3900
gagggacaaa acgcaattaa aaaagctttt aactctacat caagatttgc acgtctgcaa    3960
catattcaaa cttgtctagc aggagattta ctcttcatga gatttagaac aactactggt    4020
gacgcaatgg gtatgaatat gatttctaag ggtgtcgaat actcattaaa gcaaatggta    4080
gaagagtatg gctgggaaga tatggaggtt gtctccgttt ctggtaacta ctgtaccgac    4140
aaaaaaccag ctgccatcaa ctggatcgaa ggtcgtggta agagtgtcgt cgcagaagct    4200
actattcctg gtgatgttgt cagaaaagtg ttaaaaagtg atgtttccgc attggttgag    4260
ttgaacattg ctaagaattt ggttggatct gcaatggctg gtctgttgg tggatttaac    4320
gcacatgcag ctaatttagt gacagctgtt ttccttggcat taggacaaga tcctgcacaa    4380
aatgtcgaaa gttccaactg tataacattg atgaaagaag tggacggtga tttgagaatt    4440
tccgtatcca tgccatccat cgaagtaggt accatcggtg gtggtactgt tctagaacca    4500
caaggtgcca tgttggactt attaggtgta agaggcccac atgctaccgc tcctggtacc    4560
aacgcacgtc aattagcaag aatagttgcc tgtgccgtct tggcaggtga attatcctta    4620
tgtgctgccc tagcagccgg ccatttggtt caaagtcata tgacccacaa caggaaacct    4680
gctgaaccaa caaaacctaa caatttggac gccactgata taaatcgttt gaaagatggg    4740
tccgtcacct gcattaaatc ctaaacttag tcatacgtca ttggtattct cttgaaaaag    4800
aagcacaaca gcaccatgtg ttacgtaaaa tatttacttt atagtttgta cgtcataatt    4860
tcttccatat tacaagttcg tgcatatata gaaagaattc tgttgttgta attgtcataa    4920
```

```
ctcccgggaa gcttttcaat tcatcttttt ttttttttgtt cttttttttg attccggttt    4980
ctttgaaatt ttttttgattc ggtaatctcc gagcagaagg aagaacgaag gaaggagcac    5040
agacttagat tggtatatat acgcatatgt ggtgttgaag aaacatgaaa ttgcccagta    5100
ttcttaaccc aactgcacag aacaaaaacc tgcaggaaac gaagataaat catgtcgaaa    5160
gctacatata aggaacgtgc tgctactcat cctagtcctg ttgctgccaa gctatttaat    5220
atcatgcacg aaaagcaaac aaacttgtgt gcttcattgg atgttcgtac caccaaggaa    5280
ttactggagt tagttgaagc attaggtccc aaaatttgtt tactaaaaac acatgtggat    5340
atcttgactg atttttccat ggagggcaca gttaagccgc taaaggcatt atccgccaag    5400
tacaattttt tactcttcga agacagaaaa tttgctgaca ttggtaatac agtcaaattg    5460
cagtactctg cgggtgtata cagaatagca gaatgggcag acattacgaa tgcacacggt    5520
gtggtgggcc caggtattgt tagcggtttg aagcaggcgg cggaagaagt aacaaaggaa    5580
cctagaggcc ttttgatgtt agcagaattg tcatgcaagg ctccctagc tactggagaa    5640 tatactaagg gtactgttga cattgcgaag agcgacaaag attttgttat cggctttatt    5700
gctcaaagag acatgggtgg aagagatgaa ggttacgatt ggttgattat gacacccggt    5760
gtgggtttag atgacaaggg agacgcattg ggtcaacagt atagaaccgt ggatgatgtg    5820
gtctctacag gatctgacat tattattgtt gggtttaaac                          5860

<210> SEQ ID NO 50
<211> LENGTH: 5050
<212> TYPE: DNA
<213> ORGANISM: Artificial Sequence
<220> FEATURE:
<223> OTHER INFORMATION: pAM489 sequence (excluding vector backbone)

<400> SEQUENCE: 50
gtttaaacta ctattagctg aattgccact gctatcgttg ttagtggcgt tagtgcttgc      60
attcaaagac atggagggcg ttattacgcc ggagctcctc gacagcagat ctgatgactg     120
gtcaatatat ttttgcattg aggctctgtt tggaattata ttttgagatg acccatctaa     180
tgtactggta tcaccagatt tcatgtcgtt ttttaaagcg gctgcttgag tcttagcaat     240
agcgtcacca tctggtgaat cctttgaagg aaccactgac gaaggtttgg acagtgacga     300
agaggatctt tcctgctttg aattagtcgc gctgggagca gatgacgagt tggtggagct     360
gggggcagga ttgctggccg tcgtgggtcc tgaatgggtc cttggctggt ccatctctat     420
tctgaaaacg gaagaggagt agggaatatt actggctgaa aataagtctt gaatgaacgt     480
atacgcgtat atttctacca atctctcaac actgagtaat ggtagttata agaaagagac     540
cgagttaggc acagttagag gcggtggaga tattccttat ggcatgtctg gcgatgataa     600
aacttttcaa acggcagccc cgatctaaaa gagctgacac ccgggagtta tgacaattac     660
aacaacagaa ttctttctat atatgcacga acttgtaata tggaagaaat tatgacgtac     720
aaactataaa gtaaatattt tacgtaacac atggtgctgt tgtgcttctt tttcaagaga     780
ataccaatga cgtatgacta agtttaggat ttaatgcagg tgacggaccc atctttcaaa     840
cgatttatat cagtggcgtc caaattgtta ggttttgttg gttcagcagg tttcctgttg     900
tgggtcatat gactttgaac caaatggccg gctgctaggg cagcacataa ggataattca     960
cctgccaaga cggcacaggc aactattctt gctaattgac gtgcgttggt accaggagcg    1020
gtagcatgtg ggcctcttac acctaataag tccaacatgg caccttgtgg ttctagaaca    1080
```

```
gtaccaccac cgatggtacc tacttcgatg gatggcatgg atacggaaat tctcaaatca    1140
ccgtccactt ctttcatcaa tgttatacag ttggaacttt cgacattttg tgcaggatct    1200
tgtcctaatg ccaagaaaac agctgtcact aaattagctg catgtgcgtt aaatccacca    1260
acagacccag ccattgcaga tccaaccaaa ttcttagcaa tgttcaactc aaccaatgcg    1320
gaaacatcac ttttttaacac ttttctgaca acatcaccag gaatagtagc ttctgcgacg    1380
acactcttac cacgaccttc gatccagttg atggcagctg ttttttgtc ggtacagtag    1440 ttaccagaaa cggagacaac ctccatatct tcccagccat actcttctac catttgcttt    1500
aatgagtatt cgacacccct agaaatcata ttcataccca ttgcgtcacc agtagttgtt    1560
ctaaatctca tgaagagtaa atctcctgct agacaagttt gaatatgttg cagacgtgca    1620
aatcttgatg tagagttaaa agcttttta attgcgtttt gtccctcttc tgagtctaac    1680
catatcttac aggcaccaga tcttttcaaa gttgggaaac ggactactgg gcctcttgtc    1740
ataccatcct tagttaaaac agttgttgca ccaccgccag cattgattgc cttacagcca    1800
cgcatggcag aagctaccaa acaaccctct gtagttgcca ttggtatatg ataagatgta    1860
ccatcgataa ccaaggggcc tataacacca acgggcaaag gcatgtaacc tataacattt    1920
tcacaacaag cgccaaatac gcggtcgtag tcataatttt tatatggtaa acgatcagat    1980
gctaatacag gagcttctgc caaaattgaa agagccttcc tacgtaccgc aaccgctctc    2040
gtagtatcac ctaattttt ctccaaagcg tacaaaggta acttaccgtg aataaccaag    2100
gcagcgacct ctttgttctt caattgtttt gtatttccac tacttaataa tgcttctaat    2160
tcttctaaag gacgtatttt cttatccaag ctttcaatat cgcgggaatc atcttcctca    2220
ctagatgatg aaggtcctga tgagctcgat tgcgcagatg ataaactttt gactttcgat    2280
ccagaaatga ctgttttatt ggttaaaact ggtgtagaag ccttttgtac aggagcagta    2340
aaagacttct tggtgacttc agtcttcacc aattggtctg cagccattat agttttttct    2400
ccttgacgtt aaagtataga ggtatattaa caatttttg ttgatacttt tatgacattt    2460
gaataagaag taatacaaac cgaaaatgtt gaaagtatta gttaaagtgg ttatgcagct    2520
tttgcattta tatatctgtt aatagatcaa aaatcatcgc ttcgctgatt aattacccca    2580
gaaataaggc taaaaaacta atcgcattat tatcctatgg ttgttaattt gattcgttga    2640
tttgaaggtt tgtggggcca ggttactgcc aattttttcct cttcataacc ataaaagcta    2700
gtattgtaga atctttattg ttcggagcag tgcggcgcga ggcacatctg cgtttcagga    2760
acgcgaccgg tgaagaccag gacgcacgga ggagagtctt ccgtcggagg gctgtcgccc    2820
gctcggcggc ttctaatccg tacttcaata tagcaatgag cagttaagcg tattactgaa    2880
agttccaaag agaaggtttt tttaggctaa gataatgggg ctctttacat ttccacaaca    2940
tataagtaag attagatatg gatatgtata tggtggtatt gccatgtaat atgattatta    3000
aacttctttg cgtccatcca aaaaaaaagt aagaatttttt gaaaattcaa tataaatggc    3060
ttcagaaaaa gaaattagga gagagagatt cttgaacgtt tccctaaat tagtagagga    3120 attgaacgca tcgcttttgg cttacggtat gcctaaggaa gcatgtgact ggtatgccca    3180
ctcattgaac tacaacactc caggcggtaa gctaaataga ggtttgtccg ttgtggacac    3240
gtatgctatt ctctccaaca agaccgttga acaattgggg caagaagaat acgaaaaggt    3300
tgccattcta ggttggtgca ttgagttgtt gcaggcttac ttcttggtcg ccgatgatat    3360
gatggacaag tccattacca gaagaggcca accatgttgg tacaaggttc ctgaagttgg    3420
ggaaattgcc atcaatgacg cattcatgtt agaggctgct atctacaagc ttttgaaatc    3480
```

```
tcacttcaga aacgaaaaat actacataga tatcaccgaa ttgttccatg aggtcacctt    3540
ccaaaccgaa ttgggccaat tgatggactt aatcactgca cctgaagaca aagtcgactc    3600
gagtaagttc tccctaaaga agcactcctt catagttact ttcaagactg cttactattc    3660
tttctacttg cctgtcgcat tggccatgta cgttgccggt atcacggatg aaaaggattt    3720
gaaacaagcc agagatgtct tgattccatt gggtgaatac ttccaaattc aagatgacta    3780
cttagactgc ttcggtaccc cagaacagat cggtaagatc ggtacagata tccaagataa    3840
caaatgttct tgggtaatca acaaggcatt ggaacttgct ccgcagaaac aaagaaagac    3900
tttagacgaa aattacggta agaaggactc agtcgcagaa gccaaatgca aaagatttt     3960 caatgacttg aaaattgaac agctatacca cgaatatgaa gagtctattg ccaaggattt    4020
gaaggccaaa atttctcagg tcgatgagtc tcgtggcttc aaagctgatg tcttaactgc    4080
gttcttgaac aaagtttaca agagaagcaa atagaactaa cgctaatcga taaaacatta    4140
gatttcaaac tagataagga ccatgtataa gaactatata cttccaatat aatatagtat    4200
aagctttaag atagtatctc tcgatctacc gttccacgtg actagtccaa ggatttttt     4260 taacccggga tatatgtgta ctttgcagtt atgacgccag atggcagtag tggaagatat    4320
tctttattga aaaatagctt gtcaccttac gtacaatctt gatccggagc ttttctttt     4380 ttgccgatta agaattcggt cgaaaaaaga aaggagagg gccaagaggg agggcattgg     4440
tgactattga gcacgtgagt atacgtgatt aagcacacaa aggcagcttg gagtatgtct    4500
gttattaatt tcacaggtag ttctggtcca ttggtgaaag tttgcggctt gcagagcaca    4560
gaggccgcag aatgtgctct agattccgat gctgacttgc tgggtattat atgtgtgccc    4620
aatagaaaga gaacaattga cccggttatt gcaggaaaaa tttcaagtct tgtaaaagca    4680
tataaaaata gttcaggcac tccgaaatac ttggttggcg tgtttcgtaa tcaacctaag    4740
gaggatgttt tggctctggt caatgattac ggcattgata tcgtccaact gcatggagat    4800
gagtcgtggc aagaatacca agagttcctc ggtttgccag ttattaaaag actcgtatt     4860 ccaaaagact gcaacatact actcagtgca gcttcacaga aacctcattc gtttattccc    4920
ttgtttgatt cagaagcagg tgggacaggt gaacttttgg attggaactc gatttctgac    4980
tgggttggaa ggcaagagag ccccgaaagc ttacatttta tgttagctgg tggactgacg    5040
ccgtttaaac                                                          5050
```

<210> SEQ ID NO 51
<211> LENGTH: 6081
<212> TYPE: DNA
<213> ORGANISM: Artificial Sequence
<220> FEATURE:
<223> OTHER INFORMATION: pAM497 sequence (excluding vector backbone)

<400> SEQUENCE: 51

```
gtttaaactt ttccaatagg tggttagcaa tcgtcttact ttctaacttt tcttaccttt      60
tacatttcag caatatatat atatatattt caaggatata ccattctaat gtctgcccct     120
aagaagatcg tcgttttgcc aggtgaccac gttggtcaag aaatcacagc cgaagccatt     180
aaggttctta agctatttc tgatgttcgt tccaatgtca agttcgattt cgaaaatcat      240
ttaattggtg gtgctgctat cgatgctaca ggtgttccac ttccagatga ggcgctggaa     300
gcctccaaga aggctgatgc cgttttgtta ggtgctgtgg gtggtcctaa atggggtacc     360
ggtagtgtta gacctgaaca aggtttacta aaaatccgta agaacttca attgtacgcc      420
```

| | |
|---|---|
| aacttaagac catgtaactt tgcatccgac tctcttttag acttatctcc aatcaagcca | 480 |
| caatttgcta aaggtactga cttcgttgtt gtcagagaat tagtgggagg tatttacttt | 540 |
| ggtaagagaa aggaagacgt ttagcttgcc tcgtccccgc cgggtcaccc ggccagcgac | 600 |
| atggaggccc agaataccct ccttgacagt cttgacgtgc gcagctcagg ggcatgatgt | 660 |
| gactgtcgcc cgtacattta gcccatacat ccccatgtat aatcatttgc atccatacat | 720 |
| tttgatggcc gcacggcgcg aagcaaaaat tacggctcct cgctgcagac ctgcgagcag | 780 |
| ggaaacgctc ccctcacaga cgcgttgaat tgtccccacg ccgcgcccct gtagagaaat | 840 |
| ataaaaggtt aggatttgcc actgaggttc ttctttcata tacttccttt taaaatcttg | 900 |
| ctaggataca gttctcacat cacatccgaa cataaacaac catggcagaa ccagcccaaa | 960 |
| aaaagcaaaa acaaactgtt caggagcgca aggcgtttat ctcccgtatc actaatgaaa | 1020 |
| ctaaaattca aatcgctatt tcgctgaatg gtggttatat tcaaataaaa gattcgattc | 1080 |
| ttcctgcaaa gaaggatgac gatgtagctt cccaagctac tcagtcacag gtcatcgata | 1140 |
| ttcacacagg tgttggcttt ttggatcata tgatccatgc gttggcaaaa cactctggtt | 1200 |
| ggtctcttat tgttgaatgt attggtgacc tgcacattga cgatcaccat actaccgaag | 1260 |
| attgcggtat cgcattaggg caagcgttca agaagcaat gggtgctgtc cgtggtgtaa | 1320 |
| aaagattcgg tactgggttc gcaccattgg atgaggcgct atcacgtgcc gtagtcgatt | 1380 |
| tatctagtag accatttgct gtaatcgacc ttggattgaa gagagagatg attggtgatt | 1440 |
| tatccactga aatgattcca cacttttttgg aaagtttcgc ggaggcggcc agaattactt | 1500 |
| tgcatgttga ttgtctgaga ggtttcaacg atcaccacag aagtgagagt gcgttcaagg | 1560 |
| ctttggctgt tgccataaga gaagctattt ctagcaatgg caccaatgac gttccctcaa | 1620 |
| ccaaggtgt tttgatgtga agtactgaca ataaaaagat tcttgttttc aagaacttgt | 1680 |
| catttgtata gttttttttat attgtagttg ttctatttta atcaaatgtt agcgtgattt | 1740 |
| atatttttt tcgcctcgac atcatctgcc cagatgcgaa gttaagtgcg cagaaagtaa | 1800 |
| tatcatgcgt caatcgtatg tgaatgctgg tcgctatact gctgtcgatt cgatactaac | 1860 |
| gccgccatcc acccgggttt ctcattcaag tggtaactgc tgttaaaatt aagatattta | 1920 |
| taaattgaag cttggtcgtt ccgaccaata ccgtagggaa acgtaaatta gctattgtaa | 1980 |
| aaaaaggaaa agaaaagaaa agaaaatgt tacatatcga attgatctta ttcctttggt | 2040 |
| agaccagtct ttgcgtcaat caaagattcg tttgtttctt gtgggcctga accgacttga | 2100 |
| gttaaaatca ctctggcaac atccttttgc aactcaagat ccaattcacg tgcagtaaag | 2160 |
| ttagatgatt caaattgatg gttgaaagcc tcaagctgct cagtagtaaa tttcttgtcc | 2220 |
| catccaggaa cagagccaaa caatttatag ataaatgcaa agagtttcga ctcatttcca | 2280 |
| gctaagtagt acaacacagc atttggacct gcatcaaacg tgtatgcaac gattgtttct | 2340 |
| ccgtaaaact gattaatggt gtggcaccaa ctgatgatac gcttggaagt gtcattcatg | 2400 |
| tagaatattg gagggaaaga gtccaaacat gtggcatgga aagagttgga atccatcatt | 2460 |
| gtttcctttg caaggtggc gaaatctttt tcaacaatgg ctttacgcat gacttcaaat | 2520 |
| ctctttggta cgacatgttc aattctttct ttaaatagtt cggaggttgc cacggtcaat | 2580 |
| tgcataccct gagtggaact cacatccttt ttaatatcgc tgacaactag gacacaagct | 2640 |
| ttcatctgag gccagtcaga gctgtctgcg atttgtactg ccatggaatc atgaccatct | 2700 |
| tcagcttttc ccatttccca ggccacgtat ccgccaaaca acgatctaca agctgaacca | 2760 |
| gacccctttc ttgctattct agatatttct gaagttgact gtggtaattg gtataactta | 2820 |

```
gcaattgcag agaccaatgc agcaaagcca gcagcggagg aagctaaacc agctgctgta    2880
ggaaagttat tttcggagac aatgtggagt ttccattgag ataatgtggg caatgaggcg    2940
tccttcgatt ccatttcctt tcttaattgg cgtaggtcgc gcagacaatt ttgagttctt    3000
tcattgtcga tgctgtgtgg ttctccattt aaccacaaag tgtcgcgttc aaactcaggt    3060
gcagtagccg cagaggtcaa cgttctgagg tcatcttgcg ataaagtcac tgatatggac    3120
gaattggtgg gcagattcaa cttcgtgtcc cttttcccccc aatacttaag ggttgcgatg    3180
ttgacgggtg cggtaacgga tgctgtgtaa acggtcatta tagttttttc tccttgacgt    3240
taaagtatag aggtatatta acaattttt gttgatactt ttatgacatt tgaataagaa    3300
gtaatacaaa ccgaaaatgt tgaaagtatt agttaaagtg gttatgcagc ttttgcattt    3360
atatatctgt taatagatca aaaatcatcg cttcgctgat taattacccc agaaataagg    3420
ctaaaaaact aatcgcatta ttatcctatg gttgttaatt tgattcgttg atttgaaggt    3480
ttgtggggcc aggttactgc caattttcc tcttcataac cataaaagct agtattgtag    3540
aatctttatt gttcggagca gtgcggcgcg aggcacatct gcgtttcagg aacgcgaccg    3600
gtgaagacca ggacgcacgg aggagagtct tccgtcggag ggctgtcgcc cgctcggcgg    3660
cttctaatcc gtacttcaat atagcaatga gcagttaagc gtattactga aagttccaaa    3720
gagaaggttt ttttaggcta agataatggg gctctttaca tttccacaac atataagtaa    3780
gattagatat ggatatgtat atggtggtat tgccatgtaa tatgattatt aaacttcttt    3840
gcgtccatcc aaaaaaaaag taagaatttt tgaaaattca atataaatgt cagagttgag    3900
agccttcagt gccccaggga aagcgttact agctggtgga tatttagttt tagatccgaa    3960
atatgaagca tttgtagtcg gattatcggc aagaatgcat gctgtagccc atccttacgg    4020
ttcattgcaa gagtctgata agtttgaagt gcgtgtgaaa agtaaacaat ttaaagatgg    4080
ggagtggctg taccatataa gtcctaaaac tggcttcatt cctgtttcga taggcggatc    4140
taagaacccct ttcattgaaa aagttatcgc taacgtattt agctacttta agcctaacat    4200
ggacgactac tgcaatagaa acttgttcgt tattgatatt ttctctgatg atgcctacca    4260
ttctcaggag gacagcgtta ccgaacatcg tggcaacaga agattgagtt ttcattcgca    4320
cagaattgaa gaagttccca aaacagggct gggctcctcg gcaggtttag tcacagtttt    4380
aactacagct ttggcctcct tttttgtatc ggacctggaa aataatgtag acaaatatag    4440
agaagttatt cataatttat cacaagttgc tcattgtcaa gctcagggta aaattggaag    4500
cgggtttgat gtagcggcgg cagcatatgg atctatcaga tatagaagat tcccacccgc    4560
attaatctct aatttgccag atattggaag tgctacttac ggcagtaaac tggcgcattt    4620
ggttaatgaa gaagactgga atataacgat taaagtaac catttacctt cgggattaac    4680
tttatggatg ggcgatatta agaatggttc agaaacagta aaactggtcc agaaggtaaa    4740
aaattggtat gattcgcata tgccggaaag cttgaaaata tatacagaac tcgatcatgc    4800
aaattctaga tttatggatg gactatctaa actagatcgc ttacacgaga ctcatgacga    4860
ttacagcgat cagatatttg agtctcttga gaggaatgac tgtacctgtc aaaagtatcc    4920
tgagatcaca gaagttagag atgcagttgc cacaattaga cgttccttta gaaaaataac    4980
taaagaatct ggtgccgata tcgaacctcc cgtacaaact agcttattgg atgattgcca    5040
gaccttaaaa ggagttctta cttgcttaat acctggtgct ggtggttatg acgccattgc    5100
agtgattgct aagcaagatg ttgatcttag ggctcaaacc gctgatgaca aaagatttc    5160
```

| | |
|---|---|
| taaggttcaa tggctggatg taactcaggc tgactggggt gttaggaaag aaaaagatcc | 5220 |
| ggaaacttat cttgataaat aacttaaggt agataatagt ggtccatgtg acatcttat | 5280 |
| aaatgtgaag tttgaagtga ccgcgcttaa catctaacca ttcatcttcc gatagtactt | 5340 |
| gaaattgttc ctttcggcgg catgataaaa ttcttttaat gggtacaagc tacccgggaa | 5400 |
| agattctctt tttttatgat atttgtacat aaactttata aatgaaattc ataatagaaa | 5460 |
| cgacacgaaa ttacaaaatg gaatatgttc atagggtaga cgaaactata tacgcaatct | 5520 |
| acatacattt atcaagaagg agaaaaagga ggatgtaaag gaatacaggt aagcaaattg | 5580 |
| atactaatgg ctcaacgtga taaggaaaaa gaattgcact ttaacattaa tattgacaag | 5640 |
| gaggagggca ccacacaaaa agttaggtgt aacagaaaat catgaaacta tgattcctaa | 5700 |
| tttatatatt ggaggatttt ctctaaaaaa aaaaaaatac aacaaataaa aaacactcaa | 5760 |
| tgacctgacc atttgatgga gtttaagtca ataccttctt gaaccatttc ccataatggt | 5820 |
| gaaagttccc tcaagaattt tactctgtca gaaacggcct taacgacgta gtcgacctcc | 5880 |
| tcttcagtac taaatctacc aataccaaat ctgatggaag aatgggctaa tgcatcatcc | 5940 |
| ttacccagcg catgtaaaac ataagaaggt tctagggaag cagatgtaca ggctgaaccc | 6000 |
| gaggataatg cgatatccct tagtgccatc aataaagatt ctccttccac gtaggcgaaa | 6060 |
| gaaacgttaa cacgtttaaa c | 6081 |

<210> SEQ ID NO 52
<211> LENGTH: 4933
<212> TYPE: DNA
<213> ORGANISM: Artificial Sequence
<220> FEATURE:
<223> OTHER INFORMATION: pAM493 sequence (excluding vector backbone)

<400> SEQUENCE: 52

| | |
|---|---|
| gtttaaacta ctcagtatat taagtttcga attgaagggc gaactcttat tcgaagtcgg | 60 |
| agtcaccaca acacttccgc ccatactctc cgaatcctcg tttcctaaag taagtttact | 120 |
| tccacttgta ggcctattat taatgatatc tgaataatcc tctattaggg ttggatcatt | 180 |
| cagtagcgcg tgcgattgaa aggagtccat gcccgacgtc gacgtgatta gcgaaggcgc | 240 |
| gtaaccattg tcatgtctag cagctataga actaacctcc ttgacaccac ttgcggaagt | 300 |
| ctcatcaaca tgctcttcct tattactcat tctcttacca agcagagaat gttatctaaa | 360 |
| aactacgtgt atttcacctc tttctcgact tgaacacgtc caactcctta agtactacca | 420 |
| cagccaggaa agaatggatc cagttctaca cgatagcaaa gcagaaaaca caaccagcgt | 480 |
| acccctgtag aagcttcttt gtttacagca cttgatccat gtagccatac tcgaaatttc | 540 |
| aactcatctg aaacttttcc tgaaggttga aaaagaatgc cataagggtc acccgaagct | 600 |
| tattcacgcc cgggagttat gacaattaca acaacagaat tctttctata tatgcacgaa | 660 |
| cttgtaatat ggaagaaatt atgacgtaca aactataaag taaatatttt acgtaacaca | 720 |
| tggtgctgtt gtgcttcttt ttcaagagaa taccaatgac gtatgactaa gtttaggatt | 780 |
| taatgcaggt gacggaccca tctttcaaac gatttatatc agtggcgtcc aaattgttag | 840 |
| gttttgttgg ttcagcaggt ttcctgttgt gggtcatatg actttgaacc aaatggccgg | 900 |
| ctgctagggc agcacataag gataattcac ctgccaagac ggcacaggca actattcttg | 960 |
| ctaattgacg tgcgttggta ccaggagcgg tagcatgtgg gcctcttaca cctaataagt | 1020 |
| ccaacatggc accttgtggt tctagaacag taccaccacc gatggtacct acttcgatgg | 1080 |
| atggcatgga tacggaaatt ctcaaatcac cgtccacttc tttcatcaat gttatacagt | 1140 |

```
tggaactttc gacattttgt gcaggatctt gtcctaatgc caagaaaaca gctgtcacta    1200
aattagctgc atgtgcgtta aatccaccaa cagacccagc cattgcagat ccaaccaaat    1260
tcttagcaat gttcaactca accaatgcgg aaacatcact ttttaacact tttctgacaa    1320
catcaccagg aatagtagct tctgcgacga cactcttacc acgaccttcg atccagttga    1380
tggcagctgg tttttgtcg gtacagtagt taccagaaac ggagacaacc tccatatctt    1440
cccagccata ctcttctacc atttgcttta atgagtattc gacacccta gaaatcatat     1500 tcatacccat tgcgtcacca gtagttgttc taaatctcat gaagagtaaa tctcctgcta    1560
gacaagtttg aatatgttgc agacgtgcaa atcttgatgt agagttaaaa gctttttaa     1620 ttgcgttttg tccctcttct gagtctaacc atatcttaca ggcaccagat cttttcaaag    1680
ttgggaaacg gactactggg cctcttgtca taccatcctt agttaaaaca gttgttgcac    1740
caccgccagc attgattgcc ttacagccac gcatggcaga agctaccaaa caaccctctg    1800
tagttgccat tggtatatga taagatgtac catcgataac caaggggcct ataacaccaa    1860
cgggcaaagg catgtaacct ataacatttt cacaacaagc gccaaatacg cggtcgtagt    1920
cataattttt atatggtaaa cgatcagatg ctaatacagg agcttctgcc aaaattgaaa    1980
gagccttcct acgtaccgca accgctctcg tagtatcacc taattttttc tccaaagcgt    2040
acaaaggtaa cttaccgtga ataaccaagg cagcgacctc tttgttcttc aattgttttg    2100
tatttccact acttaataat gcttctaatt cttctaaagg acgtattttc ttatccaagc    2160
tttcaatatc gcgggaatca tcttcctcac tagatgatga aggtcctgat gagctcgatt    2220
gcgcagatga taaactttg actttcgatc cagaaatgac tgttttattg gttaaaactg     2280
gtgtagaagc cttttgtaca ggagcagtaa aagacttctt ggtgacttca gtcttcacca    2340
attggtctgc agccattata gttttttctc cttgacgtta aagtatagag gtatattaac    2400
aattttttgt tgatacttt atgacatttg aataagaagt aatacaaacc gaaaatgttg      2460
aaagtattag ttaaagtggt tatgcagctt ttgcatttat atatctgtta atagatcaaa    2520
aatcatcgct tcgctgatta attccccag aaataaggct aaaaaactaa tcgcattatt      2580
atcctatggt tgttaatttg attcgttgat ttgaaggttt gtggggccag ttactgcca      2640 attttttcctc ttcataacca taaaagctag tattgtagaa tctttattgt tcggagcagt    2700
gcggcgcgag gcacatctgc gttcaggaa cgcgaccggt gaagaccagg acgcacggag      2760
gagagtcttc cgtcggaggg ctgtcgcccg ctcggcggct tctaatccgt acttcaatat    2820
agcaatgagc agttaagcgt attactgaaa gttccaaaga gaaggttttt ttaggctaag    2880
ataatggggc tctttacatt tccacaacat ataagtaaga ttagatatgg atatgtatat    2940
ggtggtattg ccatgtaata tgattattaa acttctttgc gtccatccaa aaaaaaagta    3000 agaattttg aaaattcaat ataaatgact gccgacaaca atagtatgcc ccatggtgca      3060
gtatctagtt acgccaaatt agtgcaaaac caaacacctg aagacatttt ggaagagttt    3120
cctgaaatta ttccattaca acaaagacct aatacccgat ctagtgagac gtcaaatgac    3180
gaaagcggag aaacatgttt ttctggtcat gatgaggagc aaattaagtt aatgaatgaa    3240
aattgtattg ttttggattg ggacgataat gctattggtg ccgtaccaa gaaagtttgt      3300 catttaatgg aaaatattga aaagggttta ctacatcgtg cattctccgt ctttattttc    3360
aatgaacaag gtgaattact tttacaacaa agagccactg aaaaaataac tttccctgat    3420 cttttggacta acacatgctg ctctcatcca ctatgtattg atgacgaatt aggttttgaag   3480
```

```
ggtaagctag acgataagat taagggcgct attactgcgg cggtgagaaa actagatcat    3540
gaattaggta ttccagaaga tgaaactaag acaaggggta agtttcactt tttaaacaga    3600
atccattaca tggcaccaag caatgaacca tggggtgaac atgaaattga ttacatccta    3660
tttttataaga tcaacgctaa agaaaacttg actgtcaacc caaacgtcaa tgaagttaga    3720
gacttcaaat gggtttcacc aaatgatttg aaaactatgt ttgctgaccc aagttacaag    3780
tttacgcctt ggtttaagat tatttgcgag aattacttat tcaactggtg ggagcaatta    3840
gatgaccttt ctgaagtgga aaatgacagg caaattcata gaatgctata acaacgcgtc    3900
aataatatag ctacataaa aatcataata actttgttat catagcaaaa tgtgatataa    3960
aacgtttcat ttcacctgaa aaatagtaaa aataggcgac aaaaatcctt agtaatatgt    4020
aaactttatt ttctttattt acccgggagt cagtctgact cttgcgagag atgaggatgt    4080
aataatacta atctcgaaga tgccatctaa tacatataga catacatata tatatatata    4140
cattctatat attcttaccc agattctttg aggtaagacg gttgggtttt atcttttgca    4200
gttggtacta ttaagaacaa tcgaatcata agcattgctt acaaagaata cacatacgaa    4260
atattaacga taatgtcaat tacgaagact gaactggacg gtatattgcc attggtggcc    4320
agaggtaaag ttagagacat atatgaggta gacgctggta cgttgctgtt tgttgctacg    4380
gatcgtatct ctgcatatga cgttattatg gaaaacagca ttcctgaaaa ggggatccta    4440
ttgaccaaac tgtcagagtt ctggttcaag ttcctgtcca acgatgttcg taatcatttg    4500
gtcgacatcg ccccaggtaa gactattttc gattatctac ctgcaaaatt gagcgaacca    4560
aagtacaaaa cgcaactaga agaccgctct ctattggttc acaaacataa actaattcca    4620
ttggaagtaa ttgtcagagg ctacatcacc ggatctgctt ggaaagagta cgtaaaaaca    4680
ggtactgtgc atggtttgaa acaacctcaa ggacttaaag aatctcaaga gttcccagaa    4740
ccaatcttca ccccatcgac caaggctgaa caaggtgaac atgacgaaaa catctctcct    4800
gcccaggccg ctgagctggt gggtgaagat ttgtcacgta gagtggcaga actggctgta    4860
aaactgtact ccaagtgcaa agattatgct aaggagaagg gcatcatcat cgcagacact    4920
aaattgttta aac                                                       4933
```

<210> SEQ ID NO 53
<211> LENGTH: 8425
<212> TYPE: DNA
<213> ORGANISM: Artificial Sequence
<220> FEATURE:
<223> OTHER INFORMATION: pAM426 sequence

<400> SEQUENCE: 53

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatcga ctacgtcgta aggccgtttc tgacagagta aaattcttga gggaactttc     240
accattatgg gaaatgcttc aagaaggtat tgacttaaac tccatcaaat ggtcaggtca     300
ttgagtgttt tttatttgtt gtattttttt tttttagag aaaatcctcc aatatcaaat      360
taggaatcgt agtttcatga ttttctgtta cacctaactt tttgtgtggt gccctcctcc     420
ttgtcaatat taatgttaaa gtgcaattct ttttccttat cacgttgagc cattagtatc     480
aatttgctta cctgtattcc tttactatcc tccttttttct ccttcttgat aaatgtatgt    540
agattgcgta tatagtttcg tctaccctat gaacatattc catttttgtaa tttcgtgtcg   600
```

-continued

```
tttctattat gaatttcatt tataaagttt atgtacaaat atcataaaaa aagagaatct      660
ttttaagcaa ggattttctt aacttcttcg gcgacagcat caccgacttc ggtggtactg      720
ttggaaccac ctaaatcacc agttctgata cctgcatcca aaacctttt aactgcatct       780
tcaatggcct taccttcttc aggcaagttc aatgacaatt tcaacatcat tgcagcagac      840
aagatagtgg cgatagggtc aaccttattc tttggcaaat ctggagcaga accgtggcat      900
ggttcgtaca aaccaaatgc ggtgttcttg tctggcaaag aggccaagga cgcagatggc      960
aacaaaccca aggaacctgg ataacggag gcttcatcgg agatgatatc accaaacatg      1020
ttgctggtga ttataatacc atttaggtgg gttgggttct taactaggat catggcggca      1080
gaatcaatca attgatgttg aaccttcaat gtagggaatt cgttcttgat ggtttcctcc      1140
acagtttttc tccataatct tgaagaggcc aaaagattag ctttatccaa ggaccaaata      1200
ggcaatggtg gctcatgttg tagggccatg aaagcggcca ttcttgtgat tctttgcact      1260
tctggaacgg tgtattgttc actatcccaa gcgacaccat caccatcgtc ttcctttctc      1320
ttaccaaagt aaatacctcc cactaattct ctgacaacaa cgaagtcagt accttagca      1380
aattgtggct tgattggaga taagtctaaa agagagtcgg atgcaaagtt acatggtctt      1440
aagttggcgt acaattgaag ttctttacgg atttttagta aaccttgttc aggtctaaca      1500
ctaccggtac cccatttagg accagccaca gcacctaaca aaacggcatc aaccttcttg      1560
gaggcttcca gcgcctcatc tggaagtggg acacctgtag catcgatagc agcaccacca      1620
attaaatgat tttcgaaatc gaacttgaca ttggaacgaa catcagaaat agctttaaga      1680
accttaatgg cttcggctgt gatttcttga ccaacgtggt cacctggcaa aacgacgatc      1740
ttcttagggg cagacattac aatggtatat ccttgaaata tataaaaaa aaggcgcctt      1800
agaccgctcg gccaaacaac caattacttg ttgagaaata gagtataatt atcctataaa      1860
tataacgttt ttgaacacac atgaacaagg aagtacagga caattgattt tgaagagaat      1920
gtggattttg atgtaattgt tgggattcca ttttaataa ggcaataata ttaggtatgt      1980
ggatatacta gaagttctcc tcgaccgtcg atatgcggtg tgaaataccg cacagatgcg      2040
taaggagaaa ataccgcatc aggaaattgt aaacgttaat attttgttaa aattcgcgtt      2100
aaattttgt taaatcagct catttttaa ccaataggcc gaaatcggca aaatcccta       2160
taaatcaaaa gaatagaccg agatagggtt gagtgttgtt ccagtttgga acaagagtcc      2220
actattaaag aacgtggact ccaacgtcaa agggcgaaaa accgtctatc agggcgatgg      2280
cccactacgt ggaagatccg aggcctagct ttaacgaacg cagaattttc gagttattaa      2340
acttaaaata cgctgaaccc gaacatagaa atatcgaatg ggaaaaaaaa actgcataaa      2400
ggcattaaaa gaggagcgaa ttttttttta ataaaaatct taataatcat taaaagataa      2460
ataatagtct atatatacgt atataaataa aaatattca aaaatataaa taaactatta      2520
ttttagcgta aaggatgggg aaagagaaaa gaaaaaaatt gatctatcga tttcaattca      2580
attcaatttta tttcttttcg gataagaaag caacacctgg caattcctta ccttccaata      2640
attccaaaga agcaccacca ccagtagaga catgggagac ccgggccatg gttagatga       2700
catagggtaa actagcaatg atttgatcaa atgcttgtat tcatctccca ttctcgtaaa      2760
attgtcttta cctgcatatt ggacctctaa aaattggcaa agatatataa cagccataag      2820
taaaggtctt gggatattct tgttgttaa atactctctg tttatgtctt tccaaacgtc       2880
ctccacttcc ttataaatca gtgtctgagc atattcttcg ttgacattgt attccttcat      2940
```

```
gtaagattct aaagagcttg aactatgttt tctctcctgt tccgctttat gagtcatcag    3000
gtcatttaat ctcctaccca gaataccact gtaacggaat aaaggcggag cagatacagc    3060
ccactcaact gattccttag tgaaaatatc gctcattcct agataacagg tagttgttag    3120
caagtttgca ccaccagtga taataactac gggatcgtgc tcttcagttg tcggtatgtg    3180
tccttcatta gcccatttcg cttctaccat tagattcctt acgaattctt taacgaactc    3240
cttcccacag ttgaataaat cagttctacc ttctttggcc agaaactcct ccatttctgt    3300
gtaggtatcc atgaataatt tgtaaatagg cttcatgtat tccggcaacg tgtctaagca    3360
ggtgatcgac catcttttcca cggcttcagt gaaaatcttt aactcctcgt aagttccata    3420
tgcgtcatac gtgtcatcaa taagtgttat cacagcaact gccttagtga aaaaaactct    3480
agctcttgaa tactggggtt cgtaaccaga acctaaaccc caaaaatagc attcaacgat    3540
acgatctctc agacatgggg cattttttctt aatatcaaat gccttccacc acttgcatac    3600
gtgactcaac tcttccttat gtaggctctg caatagattg aactccagtt tagctaactt    3660
tagcagagtt ttattatggg agtcttgttg ctgatagaag ggtatgtact gggcggcctc    3720
gatccttggc aatctcttcc acaatggttg ctttaaagct ctctggattt cagtgaataa    3780
agcggggttt gtactaaacg cgtcctttgt cataatcgat agccttgatc ttgtgaatcc    3840
cagggcatct tcaagaatta tttcgcccgg aactctcatg gacgtagcct catataattc    3900
caacaatcct tcaacatcat tcgctaacga ttgtttaaaa gcaccattct tgtctttata    3960
gttattaaac acatcacacg tgacatagta tccttgttta cgcatcagcc taaaccataa    4020
gctagacctg tcgccattcc aattatcacc ataggtctcg taaatacatt gcaatgcatg    4080
atcaatttca cgttcaaaat gatacggaat acctaaacgt tgaatctcgt caatcagctt    4140
caacaaattt gcatgtttca taggaatatc caatgcttcc tttaacaact gtcttacttc    4200
cttctttaga tcgttactca tttgctccac accctgttca acttgtttct cataaatcaa    4260
aaattgatcg ccccaaatag aaggtgggaa atttgcaatt ggccttatag gtttctcttc    4320
agtcaaggcc attgttttct gcagatccgg ggttttttct ccttgacgtt aaagtataga    4380
ggtatattaa caatttttgt ttgatacttt tattacattt gaataagaag taatacaaac    4440
cgaaaatgtt gaaagtatta gttaaagtgg ttatgcagtt tttgcattta tatatctgtt    4500
aatagatcaa aaatcatcgc ttcgctgatt aattacccca gaaataaggc taaaaaacta    4560
atcgcattat catcctatgg ttgttaattt gattcgttca tttgaaggtt tgtggggcca    4620
ggttactgcc aattttttcct cttcataacc ataaaagcta gtattgtaga atctttattg    4680
ttcggagcag tgcggcgcga ggcacatctg cgtttcagga acgcgaccgg tgaagacgag    4740
gacgcacgga ggagagtctt ccttcggagg gctgtcaccc gctcggcggc ttctaatccg    4800
tactaagatc tgctttaatt tggccggcga acgtggcgag aaaggaaggg aagaaagcga    4860
aaggagcggg cgctagggcg ctggcaagtg tagcggtcac gctgcgcgta accaccacac    4920
ccgccgcgct taatgcgccg ctacagggcg cgtcgcgcca ttcgccattc aggctgcgca    4980
actgttggga agggcgatcg gtgcgggcct cttcgctatt acgccagctg cattaatgaa    5040
tcggccaacg cgcggggaga ggcggttttgc gtattgggcg ctcttccgct tcctcgctca    5100
ctgactcgct gcgctcggtc gttcggctgc ggcgagcggt atcagctcac tcaaaggcgg    5160
taatacggtt atccacagaa tcaggggata acgcaggaaa gaacatgtga gcaaaaggcc    5220
agcaaaaggc caggaaccgt aaaaaggccg cgttgctggc gttttccat aggctccgcc    5280
cccctgacga gcatcacaaa aatcgacgct caagtcagag gtggcgaaac ccgacaggac    5340
```

```
tataaagata ccaggcgttt cccctggaa gctccctcgt gcgctctcct gttccgaccc      5400
tgccgcttac cggatacctg tccgccttc tcccttcggg aagcgtggcg ctttctcata      5460
gctcacgctg taggtatctc agttcggtgt aggtcgttcg ctccaagctg ggctgtgtgc     5520
acgaaccccc cgttcagccc gaccgctgcg ccttatccgg taactatcgt cttgagtcca     5580
acccggtaag acacgactta tcgccactgg cagcagccac tggtaacagg attagcagag     5640
cgaggtatgt aggcggtgct acagagttct gaagtggtg gcctaactac ggctacacta      5700
gaaggacagt atttggtatc tgcgctctgc tgaagccagt taccttcgga aaaagagttg     5760
gtagctcttg atccggcaaa caaaccaccg ctggtagcgg tggttttttt gtttgcaagc     5820
agcagattac gcgcagaaaa aaaggatctc aagaagatcc tttgatcttt tctacggggt     5880
ctgacgctca gtggaacgaa aactcacgtt aagggatttt ggtcatgaga ttatcaaaaa     5940
ggatcttcac ctagatcctt ttaaattaaa aatgaagttt taaatcaatc taaagtatat     6000
atgagtaaac ttggtctgac agttaccaat gcttaatcag tgaggcacct atctcagcga     6060
tctgtctatt tcgttcatcc atagttgcct gactccccgt cgtgtagata actacgatac     6120
gggagggctt accatctggc cccagtgctg caatgatacc gcgagaccca cgctcaccgg     6180
ctccagattt atcagcaata aaccagccag ccggaagggc cgagcgcaga gtggtcctg     6240
caactttatc cgcctccatc cagtctatta attgttgccg ggaagctaga gtaagtagtt     6300
cgccagttaa tagtttgcgc aacgttgttg ccattgctac aggcatcgtg gtgtcacgct     6360
cgtcgtttgg tatggcttca ttcagctccg gttcccaacg atcaaggcga gttacatgat     6420
cccccatgtt gtgcaaaaaa gcggttagct ccttcggtcc tccgatcgtt gtcagaagta     6480
agttggccgc agtgttatca ctcatggtta tggcagcact gcataattct cttactgtca     6540
tgccatccgt aagatgcttt tctgtgactg gtgagtactc aaccaagtca ttctgagaat     6600
agtgtatgcg gcgaccgagt tgctcttgcc cggcgtcaat acgggataat accgcgccac     6660
atagcagaac tttaaaagtg ctcatcattg gaaaacgttc ttcggggcga aaactctcaa     6720
ggatcttacc gctgttgaga tccagttcga tgtaacccac tcgtgcaccc aactgatctt     6780
cagcatcttt tactttcacc agcgtttctg ggtgagcaaa aacaggaagg caaaatgccg     6840
caaaaaaggg aataagggcg acacggaaat gttgaatact catactcttc cttttttcaat    6900
attattgaag catttatcag ggttattgtc tcatgagcgg atacatattt gaatgtattt     6960
agaaaaataa acaaataggg gttccgcgca catttccccg aaaagtgcca cctgaacgaa     7020
gcatctgtgc ttcattttgt agaacaaaaa tgcaacgcga gagcgctaat ttttcaaaca     7080
aagaatctga gctgcatttt tacagaacag aaatgcaacg cgaaagcgct attttaccaa     7140
cgaagaatct gtgcttcatt tttgtaaaac aaaaatgcaa cgcgagagcg ctaattttt    7200
aaacaaagaa tctgagctgc atttttacag aacagaaatg caacgcgaga gcgctatttt     7260
accaacaaag aatctatact tctttttgt tctacaaaaa tgcatcccga gagcgctatt     7320
tttctaacaa agcatcttag attactttt ttctcctttg tgcgctctat aatgcagtct     7380
cttgataact ttttgcactg taggtccgtt aaggttagaa gaaggctact ttggtgtcta     7440
ttttctcttc cataaaaaaa gcctgactcc acttcccgcg tttactgatt actagcgaag     7500
ctgcgggtgc atttttttcaa gataaaggca tccccgatta tattctatac cgatgtggat     7560
tgcgcatact tgtgaacag aaagtgatag cgttgatgat tcttcattgg tcagaaaatt     7620
atgaacggtt tcttctattt tgtctctata tactacgtat aggaaatgtt tacattttcg     7680
```

```
tattgttttc gattcactct atgaatagtt cttactacaa ttttttttgtc taaagagtaa    7740 tactagagat aaacataaaa aatgtagagg tcgagtttag atgcaagttc aaggagcgaa    7800
aggtggatgg gtaggttata tagggatata gcacagagat atatagcaaa gagatacttt    7860
tgagcaatgt ttgtggaagc ggtattcgca atatttagt agctcgttac agtccggtgc    7920 gttttttggtt ttttgaaagt gcgtcttcag agcgcttttg gtttcaaaa gcgctctgaa    7980 gttcctatac tttctagaga ataggaactt cggaatagga acttcaaagc gtttccgaaa    8040
acgagcgctt ccgaaaatgc aacgcgagct gcgcacatac agctcactgt tcacgtcgca    8100
cctatatctg cgtgttgcct gtatatatat atacatgaga agaacggcat agtgcgtgtt    8160
tatgcttaaa tgcgtactta tatgcgtcta tttatgtagg atgaaaggta gtctagtacc    8220
tcctgtgata ttatcccatt ccatgcgggg tatcgtatgc ttccttcagc actacccttt    8280
agctgttcta tatgctgcca ctcctcaatt ggattagtct catccttcaa tgctatcatt    8340
tcctttgata ttggatcata ctaagaaacc attattatca tgacattaac ctataaaaat    8400
aggcgtatca cgaggccctt tcgtc                                         8425
```

<210> SEQ ID NO 54
<211> LENGTH: 13280
<212> TYPE: DNA
<213> ORGANISM: Artificial Sequence
<220> FEATURE:
<223> OTHER INFORMATION: pAM322 sequence
<400> SEQUENCE: 54

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatcga ctacgtcgta aggccgtttc tgacagagta aaattcttga gggaactttc     240
accattatgg gaaatgcttc aagaaggtat tgacttaaac tccatcaaat ggtcaggtca     300
ttgagtgttt tttatttgtt gtatttttt tttttagag aaaatcctcc aatatcaaat     360
taggaatcgt agtttcatga ttttctgtta cacctaactt tttgtgtggt gccctcctcc     420
ttgtcaatat taatgttaaa gtgcaattct ttttccttat cacgttgagc cattagtatc     480
aatttgctta cctgtattcc tttactatcc tccttttct ccttcttgat aaatgtatgt     540
agattgcgta tatagtttcg tctaccctat gaacatattc cattttgtaa tttcgtgtcg     600
tttctattat gaatttcatt tataaagttt atgtacaaat atcataaaaa aagagaatct     660
ttttaagcaa ggattttctt aacttcttcg gcgacagcat caccgacttc ggtggtactg     720
ttggaaccac ctaaatcacc agttctgata cctgcatcca aaccttttt aactgcatct     780 tcaatggcct taccttcttc aggcaagttc aatgacaatt tcaacatcat gcagcagac     840 aagatagtgg cgatagggtc aaccttattc tttggcaaat ctggagcaga accgtggcat     900
ggttcgtaca aaccaaatgc ggtgttcttg tctggcaaag aggccaagga cgcagatggc     960
aacaaaccca aggaacctgg gataacggag gcttcatcgg agatgatatc accaaacatg    1020
ttgctggtga ttataatacc atttaggtgg gttgggttct taactaggat catgcggca    1080 gaatcaatca attgatgttg aaccttcaat gtagggaatt cgttcttgat ggtttcctcc    1140 acagttttc tccataatct tgaagaggcc aaaagattag ctttatccaa ggaccaaata    1200
ggcaatggtg gctcatgttg tagggccatg aaagcggcca ttcttgtgat tcttgcact    1260 tctggaacgg tgtattgttc actatcccaa gcgacaccat caccatcgtc ttccttctc    1320
```

-continued

```
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttctttacgg attttagta aaccttgttc aggtctaaca    1500
ctaccggtac cccatttagg accagccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa acgacgatc    1740
ttcttagggg cagacattac aatggtatat ccttgaaata tatataaaaa aaggcgcctt   1800
agaccgctcg gccaaacaac caattacttg ttgagaaata gagtataatt atcctataaa   1860
tataacgttt ttgaacacac atgaacaagg aagtacagga caattgattt tgaagagaat   1920
gtggattttg atgtaattgt tgggattcca ttttttaataa ggcaataata ttaggtatgt   1980
ggatatacta gaagttctcc tcgaccgtcg atatgcggtg tgaaataccg cacagatgcg   2040
taaggagaaa ataccgcatc aggaaattgt aaacgttaat attttgttaa aattcgcgtt   2100
aaattttttgt taaatcagct cattttttaa ccaataggcc gaaatcggca aaatccctta   2160
taaatcaaaa gaatagaccg agatagggtt gagtgttgtt ccagtttgga acaagagtcc   2220
actattaaag aacgtggact ccaacgtcaa agggcgaaaa accgtctatc agggcgatgg   2280
cccactacgt ggaagatccg aggcctagct ttaacgaacg cagaattttc gagttattaa   2340
acttaaaata cgctgaaccc gaacatgaaa atatcgaatg ggaaaaaaaa actgcataaa   2400
ggcattaaaa gaggagcgaa ttttttttta ataaaaatct taataatcat taaaagataa   2460
ataatagtct atatatacgt atataaataa aaaatattca aaaaataaaa taaactatta   2520
ttttagcgta aaggatgggg aaagagaaaa gaaaaaaatt gatctatcga tttcaattca   2580
attcaattta tttcttttcg gataagaaag caacacctgg caattcctta ccttccaata   2640
attccaaaga agcaccacca ccagtagaga catgggagac ccgggccatg gttagataga   2700
catagggtaa actagcaatg atttgatcaa atgcttgtat tcatctccca ttctcgtaaa   2760
attgtctttta cctgcatatt ggacctctaa aaattggcaa agatatataa cagccataag   2820
taaaggtctt gggatattct tgttgttaa atactctctg tttatgtctt tccaaacgtc    2880
ctccacttcc ttataaatca gtgtctgagc atattcttcg ttgacattgt attccttcat   2940
gtaagattct aaagagcttg aactatgttt tctctcctgt tccgctttat gagtcatcag   3000
gtcatttaat ctcctaccca gaataccact gtaacgaat aaaggcggag cagatacagc    3060
ccactcaact gattccttag tgaaaatatc gctcattcct agataacagg tagttgttag   3120
caagtttgca ccaccagtga taataactac gggatcgtgc tcttcagttg tcggtatgtg   3180
tccttcatta gcccatttcg cttctaccat tagattcctt acgaattctt taacgaactc   3240
cttcccacag ttgaataaat cagttctacc ttctttggcc agaaactcct ccatttctgt   3300
gtaggtatcc atgaataatt tgtaaatagg cttcatgtat tccggcaacg tgtctaagca   3360
ggtgatcgac catcttttcca cggcttcagt gaaaatcttt aactcctcgt aagttccata   3420
tgcgtcatac gtgtcatcaa taagtgttat cacagcaact gccttagtga aaaaaactct   3480
agctcttgaa tactggggtt cgtaaccaga acctaaaccc caaaaatagc attcaacgat   3540
acgatctctc agacatgggg cattttttctt aatatcaaat gccttccacc acttgcatac   3600
gtgactcaac tcttccttat gtaggctctg caatagattg aactccagtt tagctaactt   3660
```

```
tagcagagtt ttattatggg agtcttgttg ctgatagaag ggtatgtact gggcggcctc    3720
gatccttggc aatctcttcc acaatggttg ctttaaagct ctctggattt cagtgaataa    3780
agcggggttt gtactaaacg cgtcctttgt cataatcgat agccttgatc ttgtgaatcc    3840
cagggcatct tcaagaatta tttcgcccgg aactctcatg gacgtagcct catataattc    3900
caacaatcct tcaacatcat tcgctaacga ttgtttaaaa gcaccattct tgtctttata    3960
gttattaaac acatcacacg tgacatagta tccttgttta cgcatcagcc taaaccataa    4020
gctagacctg tcgccattcc aattatcacc ataggtctcg taaatacatt gcaatgcatg    4080
atcaatttca cgttcaaaat gatacggaat acctaaacgt tgaatctcgt caatcagctt    4140
caacaaattt gcatgtttca taggaatatc caatgcttcc tttaacaact gtcttacttc    4200
cttctttaga tcgtttacta tttgctccac accctgttca acttgtttct cataaatcaa    4260
aaattgatcg ccccaaatag aaggtgggaa atttgcaatt ggcctttatag gtttctcttc   4320 agtcaaggcc attgttttct gcagatccgg ggttttttct ccttgacgtt aaagtataga    4380
ggtatattaa caatttttg ttgatacttt tattacattt gaataagaag taatacaaac     4440
cgaaaatgtt gaaagtatta gttaaagtgg ttatgcagtt tttgcattta tatatctgtt    4500
aatagatcaa aaatcatcgc ttcgctgatt aattacccca gaaataaggc taaaaaacta    4560
atcgcattat catcctatgg ttgttaattt gattcgttca tttgaaggtt tgtgggggcca   4620 ggttactgcc aattttttcct cttcataacc ataaaagcta gtattgtaga atctttattg   4680
ttcggagcag tgcggcgcga ggcacatctg cgtttcagga acgcgaccgg tgaagacgag    4740
gacgcacgga ggagagtctt ccttcggagg gctgtcaccc gctcggcggc ttctaatccg    4800
tactaagatc tgctttaatt tggccggcga acgtggcgag aaaggaaggg aagaaagcga    4860
aaggagcggg cgctagggcg ctggcaagtg tagcggtcac gctgcgcgta accaccacac    4920
ccgccgcgct taatgcgccg ctacagggcg cgtcgcgcca ttcgccattc aggctgcgca    4980
actgttggga agggcgatcg gtgcgggcct cttcgctatt acgccagctg aattggagcg    5040
acctcatgct ataccctgaga aagcaacctg acctacagga aagagttact caagaataag    5100
aattttcgtt ttaaaaccta agagtcactt taaaatttgt atacacttat ttttttttata   5160 acttatttaa taataaaaat cataaatcat aagaaattcg cttatttaga agtgtcaaca    5220
acgtatctac caacgatttg acccttttcc atcttttcgt aaatttctgg caaggtagac    5280
aagccgacaa ccttgattgg agacttgacc aaacctctgg cgaagaattg ttaattaaga    5340
gtcagtcgac ttaaaaacta gggaccaata gcaattctgt tttacgttgc attgttgcac    5400
ctgaactttc cgtcatgtca atttgatcat atgaaactcc attgggcaac ttccagttga    5460
aatgataaag aatgttggct agtggcagtt gaacattggc caaacctaac gcagcgccag    5520
gacacatacg acgtccagcc ccaaatggta aatattcata ttcggcgccc atcactgttg    5580
ccgaagagtt ttcaaatctt tcaggtataa acgcttctgc atccttccag tattcaggat    5640
ctctattgat cgcaaacaca ttaacgatta atttcgtttt gttagggata ttataaccag    5700
ccaagtttac tggctgacga cattctctag gtagcactaa cggcaagggt gggtgtagtc    5760
taagagtctc tttgatgacc atattcaagt aggacaattc ttgtatatct tcttcatgta    5820
ttttttcttt cccattcaag gccttacgta attcagcctg aaccttttcc attgctttcg    5880
gacattttat tagctcgctt atagcccatt ctatggtaga acttgaagtg tcggtccctg    5940
caccgaacat gtccaaaatt attgctttga tattatccga agtcagagga aactcagcag    6000
aatcctttaa tctaagtaat acatctaata gggtttcgtt ggttttggat gacgtattta    6060
```

```
cggtatgttc agctaccaaa ttgtcaatta agttatcaat cttttacgt aggctagtta    6120
atcttgctct cttaccgctc aagtgatgca agaactttt agatgggaaa atatcggcaa    6180
catcgaaacc gcctgtttgt ctcagtattt ctttaacaat ttcagtaagt tccttttgat    6240
ctttaattcc cttaccaaac gcagcacggg atagtatagt ggcaattagt ttaaaaacgt    6300
tttcacttaa atttactggt ctaccactac ctgaagcctt tatttcctgg actaaattcc    6360
aacattcttc ttccctcaac gattgaaatg acttaacctt ttttacagac aacaattcaa    6420
gagtacaaat cttccttaat tgtctccagt attccccata tggagcaagg acaacatcag    6480
tgttatgata taaaactatt tccccagtta aagtttcggg tctattagcg aaagtaatat    6540
cgtaggttgt aagaatttcc ttagcccact taggactcga cacgactatt gtgggtacct    6600
ctcccaattg aaggtgcatt agcgaaccat attttctcgc taaatccctt acaccctgt    6660
gtggtgtggt tccgatcaaa tggtgcatgt gaccaatgat gggtagcctc caaggttccg    6720
gcaaggactt tttagttgac ttacttctag tggcaaattt gtacacgaac aacaaaatag    6780
ttgctaaagc aattgatgta gttaaagata gtgccatagc ctttaaaatt gacttcattg    6840
ttttcctagg cctttagtga gggttgaatt cgaattttca aaaattctta cttttttttt    6900
ggatggacgc aaagaagttt aataatcata ttacatggca ttaccaccat atacatatcc    6960
atatacatat ccatatctaa tcttacttat atgttgtgga aatgtaaaga gccccattat    7020
cttagcctaa aaaaccttc tctttggaac tttcagtaat acgcttaact gctcattgct    7080
atattgaagt acggattaga agccgccgag cgggtgacag ccctccgaag gaagactctc    7140
ctccgtgcgt cctcgtcttc accggtcgcg ttcctgaaac gcagatgtgc ctcgcgccgc    7200
actgctccga caataaaga ttctacaata ctagctttta tggttatgaa gaggaaaaat    7260
tggcagtaac ctggccccac aaaccttcaa atgaacgaat caaattaaca accataggat    7320
gataatgcga ttagtttttt agccttattt ctggggtaat taatcagcga agcgatgatt    7380
tttgatctat taacagatat ataaatgcaa aaactgcata accactttaa ctaatacttt    7440
caacattttc ggtttgtatt acttcttatt caaatgtaat aaaagtatca acaaaaaatt    7500
gttaatatac ctctatactt taacgtcaag gagaaaaaac cccaagcttc ccgggaaaac    7560
aatgcaatcg acaacttccg ttaaactatc acctttcgat cttatgactg ccttgttaaa    7620
tggtaaagtt agtttcgaca cgtccaatac ttccgataca aatataccac tggcggtttt    7680
catggaaaac agggaattgc ttatgatatt aacaaccagt gtggccgttt taattggttg    7740
tgtggttgta ttggtatgga gaagatcatc aagtgccgct aagaaggccg ccgaatcacc    7800
agtcattgtc gtcccaaaga aagtcactga agatgaggtt gatgacggca gaaagaaagt    7860
tactgtattt ttcgggacac aaacgggac tgcggaaggt tttgcgaaag ctctagttga    7920
agaagccaag gcaaggtacg aaaaagcagt attcaaagtt attgatttag atgactacgc    7980
cgcagaagat gatgaatacg aagaaaagct aaagaaagaa tctttggcat tcttcttttt    8040
agctacctat ggtgacggag aaccaacaga taacgccgct agattctata atggtttac    8100
tgaaggagaa gaaaaaggtg agtggttaga taagttacaa tacgctgtct ttggattggg    8160
aaatcgtcaa tatgaacact tcaataagat tgcaaaagtg gtcgatgaaa aattagttga    8220
gcaggggct aaaaggttag tgcctgtcgg tatgggtgat gacgatcaat gtatcgaaga    8280
tgatttact gcttggaagg aattggtttg gccagaatta gatcagctat tgagggacga    8340
agatgacaca agtgtcgcta ctccgtacac cgccgctgtt ggcgaatatc gtgttgtttt    8400
```

```
tcacgataaa cctgaaactt acgatcaaga tcaattgacc aacggacacg cagttcacga    8460
cgcccaacac ccatgcagat cgaacgttgc ggtcaagaaa gaattacaca gtcccttatc    8520
cgataggagt tgtactcatt tagaatttga tatttccaat actggactat cgtatgaaac    8580
tggcgaccat gtcggtgtat atgtggaaaa cctgtctgaa gttgtagatg aagccgaaaa    8640
attgattggg cttcctccac atacatactt ttctgtgcat acagataatg aagatggtac    8700
tccacttggc ggagcctcgt taccacctcc cttttccacca tgtacactta gaaaagctct    8760
tgcatcttat gcagatgtac tttcttcacc aaagaaaagt gcattactag ctctagccgc    8820
ccatgctacc gactctactg aagctgaccg tttgaaattc tttgcttcac ctgctggcaa    8880
agacgagtac gcacagtgga ttgtggcatc tcacagatca ttgctggaag tgatggaagc    8940
cttcccatcg gcaaagccac cattaggcgt gttttcgca tctgttgccc cacgtttaca    9000
gcctagatac tattccatat cttctagccc aaaatttgcc cccaatcgta ttcatgtgac    9060
gtgtgcgctg gtgtatgaac aaactccatc aggaagggta cataaaggtg tctgtagtac    9120
atggatgaaa aacgcggtgc caatgactga atctcaagat tgttcgtggg caccaatta    9180 tgttcgtact tctaatttta gactacctag tgaccctaaa gtaccagtga ttatgatcgg    9240
gcctgggaca ggactagcgc cattcagagg tttcttacaa gaaagattgg cccaaaagga    9300
agcaggtacg gaattaggaa ccgcaattct attctttggt tgtcgtaata gaaaagttga    9360
ctttatatac gaagatgagt taaacaactt cgttgaaact ggagcgttat cagaattagt    9420
gacagcattc tctagggaag gtgcaacaaa agaatcgtc caacataaaa tgacccaaaa    9480
ggccagcgat atatggaatt tgctgtccga gggtgcctat ttgtacgttt gtggtgatgc    9540
aaagggaatg gctaaagatg ttcacaggac attgcataca attgttcagg aacaaggttc    9600
cttggattcc tctaaggcag aactttatgt taaaaacctt cagatggctg gtagatattt    9660
gcgtgatgtt tggtgagcta gctaagatcc gctctaaccg aaaaggaagg agttagacaa    9720
cctgaagtct aggtccctat ttattttttt atagttatgt tagtattaag aacgttattt    9780
atatttcaaa ttttcttt ttctgtac agacgcgtgt acgcatgtaa cattatactg        9840
aaaaccttgc ttgagaaggt tttgggacgc tcgaagatcc agctgcatta atgaatcggc    9900
caacgcgcgg ggagaggcgg tttgcgtatt gggcgctctt ccgcttcctc gctcactgac    9960
tcgctgcgct cggtcgttcg gctgcggcga gcggtatcag ctcactcaaa ggcggtaata   10020
cggttatcca cagaatcagg ggataacgca ggaaagaaca tgtgagcaaa aggccagcaa   10080
aaggccagga accgtaaaaa ggccgcgttg ctggcgtttt tccataggct ccgcccccct   10140
gacgagcatc acaaaaatcg acgctcaagt cagaggtggc gaaacccgac aggactataa   10200
agataccagg cgtttccccc tggaagctcc ctcgtgcgct ctcctgttcc gaccctgccg   10260
cttaccggat acctgtccgc ctttctccct tcgggaagcg tggcgctttc tcatagctca   10320
cgctgtaggt atctcagttc ggtgtaggtc gttcgctcca agctgggctg tgtgcacgaa   10380
ccccccgttc agcccgaccg ctgcgcctta tccggtaact atcgtcttga gtccaacccg   10440
gtaagacacg acttatcgcc actggcagca gccactggta acaggattag cagagcgagg   10500
tatgtaggcg tgctacaga gttcttgaag tggtggccta actacggcta cactagaagg   10560
acagtatttg gtatctgcgc tctgctgaag ccagttacct tcggaaaaag agttggtagc   10620
tcttgatccg gcaaacaaac caccgctggt agcggtggtt ttttgtttg caagcagcag   10680 attacgcgca gaaaaaaagg atctcaagaa gatcctttga tcttttctac ggggtctgac   10740
gctcagtgga acgaaaactc acgttaaggg attttggtca tgagattatc aaaaaggatc   10800
```

```
ttcacctaga tccttttaaa ttaaaaatga agttttaaat caatctaaag tatatatgag   10860
taaacttggt ctgacagtta ccaatgctta atcagtgagg cacctatctc agcgatctgt   10920
ctatttcgtt catccatagt tgcctgactc cccgtcgtgt agataactac gatacgggag   10980
ggcttaccat ctggcccag tgctgcaatg ataccgcgag acccacgctc accggctcca    11040
gatttatcag caataaacca gccagccgga agggccgagc gcagaagtgg tcctgcaact   11100
ttatccgcct ccatccagtc tattaattgt tgccgggaag ctagagtaag tagttcgcca   11160
gttaatagtt tgcgcaacgt tgttgccatt gctacaggca tcgtggtgtc acgctcgtcg   11220
tttggtatgg cttcattcag ctccggttcc caacgatcaa ggcgagttac atgatccccc   11280
atgttgtgca aaaaagcggt tagctccttc ggtcctccga tcgttgtcag aagtaagttg   11340
gccgcagtgt tatcactcat ggttatggca gcactgcata attctcttac tgtcatgcca   11400
tccgtaagat gcttttctgt gactggtgag tactcaacca agtcattctg agaatagtgt   11460
atgcggcgac cgagttgctc ttgcccggcg tcaatacggg ataataccgc gccacatagc   11520
agaactttaa aagtgctcat cattggaaaa cgttcttcgg ggcgaaaact ctcaaggatc   11580
ttaccgctgt tgagatccag ttcgatgtaa cccactcgtg cacccaactg atcttcagca   11640
tcttttactt tcaccagcgt ttctgggtga gcaaaacag gaaggcaaaa tgccgcaaaa    11700
aagggaataa gggcgacacg gaaatgttga atactcatac tcttcctttt tcaatattat   11760
tgaagcattt atcagggtta ttgtctcatg agcggataca tatttgaatg tatttagaaa   11820
aataaacaaa taggggttcc gcgcacattt ccccgaaaag tgccacctga acgaagcatc   11880
tgtgcttcat tttgtagaac aaaaatgcaa cgcgagagcg ctaatttttc aaacaaagaa   11940
tctgagctgc atttttacag aacagaaatg caacgcgaaa gcgctatttt accaacgaag   12000
aatctgtgct tcattttgt aaaacaaaaa tgcaacgcga gagcgctaat ttttcaaaca   12060
aagaatctga gctgcatttt tacagaacag aaatgcaacg cgagagcgct attttaccaa   12120
caaagaatct atacttcttt tttgttctac aaaaatgcat cccgagagcg ctatttttct   12180
aacaaagcat cttagattac tttttttctc ctttgtgcgc tctataatgc agtctcttga   12240
taactttttg cactgtaggt ccgttaaggt tagaagaagg ctactttggt gtctattttc   12300
tcttccataa aaaaagcctg actccacttc ccgcgtttac tgattactag cgaagctgcg   12360
ggtgcatttt tcaagataa aggcatcccc gattatattc tataccgatg tggattgcgc    12420
atactttgtg aacagaaagt gatagcgttg atgattcttc attggtcaga aaattatgaa   12480
cggtttcttc tattttgtct ctatatacta cgtataggaa atgtttacat tttcgtattg   12540
ttttcgattc actctatgaa tagttcttac tacaattttt ttgtctaaag agtaatacta   12600
gagataaaca taaaaaatgt agaggtcgag tttagatgca agttcaagga gcgaaaggtg   12660
gatgggtagg ttatataggg atatagcaca gagatatata gcaaagagat acttttgagc   12720
aatgtttgtg gaagcggtat tcgcaatatt ttagtagctc gttacagtcc ggtgcgtttt   12780
tggttttttg aaagtgcgtc ttcagagcgc ttttggtttt caaaagcgct ctgaagttcc   12840
tatactttct agagaatagg aacttcggaa taggaacttc aaagcgtttc cgaaaacgag   12900
cgcttccgaa aatgcaacgc gagctgcgca catacagctc actgttcacg tcgcacctat   12960
atctgcgtgt tgcctgtata tatatataca tgagaagaac ggcatagtgc gtgtttatgc   13020
ttaaatgcgt acttatatgc gtctatttat gtaggatgaa aggtagtcta gtacctcctg   13080
tgatattatc ccattccatg cggggtatcg tatgcttcct tcagcactac cctttagctg   13140
```

-continued

```
ttctatatgc tgccactcct caattggatt agtctcatcc ttcaatgcta tcatttcctt  13200
tgatattgga tcatactaag aaaccattat tatcatgaca ttaacctata aaaataggcg  13260
tatcacgagg ccctttcgtc                                              13280
```

APPARATUS FOR MAKING BIO-ORGANIC COMPOUNDS

CROSS-REFERENCE TO RELATED APPLICATIONS

This application claims the benefit of U.S. provisional application No. 60/808,989, filed May 26, 2006 entitled MICROOGRANISMS FOR PRODUCTION OF ISO-PRENOIDS; U.S. 60/808,666, filed May 26, 2006 entitled BIOFUELS AND METHODS FOR PRODUCTION; U.S. 60/870,592, filed Dec. 12, 2006 entitled PRODUCTION OF ISOPRENOIDS; and U.S. 60/922,782, filed Apr. 10, 2007 entitled APPARATUS FOR MAKING BIO-ORGANIC COMPOUNDS, the contents of all of which are incorporated herein by reference in their entireties.

BACKGROUND OF THE INVENTION

Traditionally, bio-organic compounds of interest have been manufactured by extraction from natural sources such as plants, microbes, and animals. However, extraction yields are usually very low as most bio-organic compounds accumulate in nature in small amounts. Given that these quantities are far less than is for many commercial applications, there remains a need for systems and procedures that produce bio-organic compounds on an industrial scale.

The present invention addresses this need. Provided are various industrial-scale systems for making bio-organic compounds using host cells. These bio-organic compounds have at least five carbon atoms and can be a carbohydrate such as a mono- or poly-alcohol, ester, ether, aldehyde, ketone, or a hydrocarbon such as an alkane, alkene, or alkyne. The bio-organic compound can be linear or cyclic and can be saturated or unsaturated.

SUMMARY OF THE INVENTION

The present invention provides various bio-organic compound production systems. In one aspect, a bio-organic compound production system is provided which comprises:
 a. at least one vessel having a capacity of at least 100 liters;
 b. an aqueous medium, within the vessel, comprising a first phase;
 c. a plurality of host cells, within the aqueous medium, capable of making, producing or synthesizing at least one bio-organic compound; and,
 d. a liquid organic second phase, comprising the at least one bio-organic compound, in contact with the first phase.

In another aspect, a method of producing at least one bio-organic compound is provided. The method comprises:
 a. culturing in an aqueous medium a plurality of host cells that make, produce or synthesize the at least one bio-organic compound wherein the aqueous medium comprises a first phase;
 b. forming an organic second phase comprising the bio-organic compound in contact with the first phase;
 c. separating at least a portion of the organic second phase from the first phase; and,
 d. isolating the at least one bio-organic compound from the organic second phase.

DETAILED DESCRIPTION OF THE INVENTION

Definitions

Figure 1:
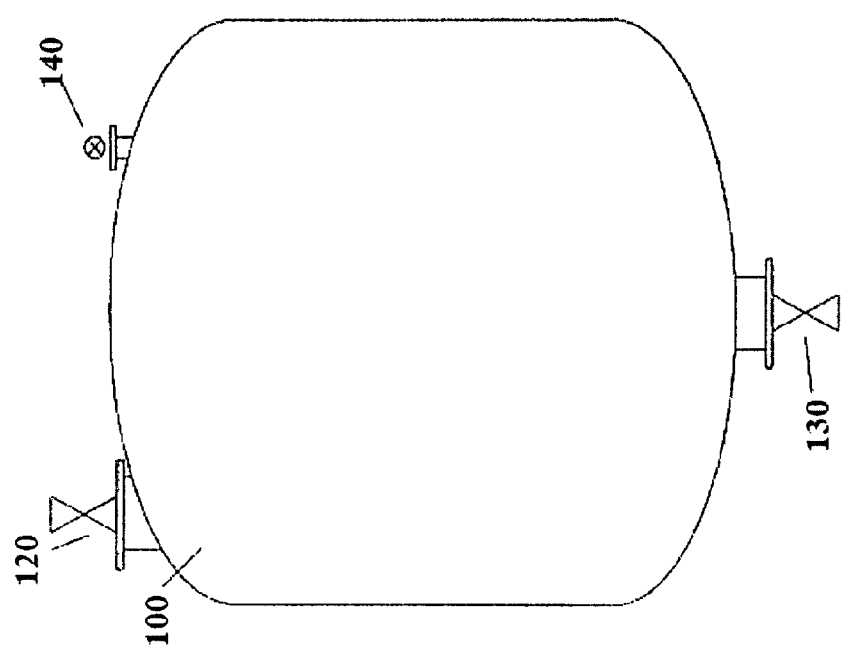
FIG. 1 is a vessel having a capacity of at least 100 liters for use in the present invention.

Unless defined otherwise, all technical and scientific terms used herein have the same meaning as commonly understood by one of ordinary skill in the art to which this invention belongs. Reference is made here to a number of terms that shall be defined to have the following meanings:

"Bio-organic compound" refers to an organic compound having at least five carbon atoms that can be made by a host cell by taking a carbohydrate carbon source and converting the carbohydrate carbon source into the desired product.

"Deoxyxylulose 5-phosphate pathway" or "DXP pathway" is used herein to refer to the pathway that converts glyceraldehyde-3-phosphate and pyruvate to IPP and DMAPP. The DXP pathway is illustrated schematically in FIG. 4.

"Endogenous" refers to a substance or process that can occur naturally, e.g., in a non-recombinant host cell.

"Heterologous nucleic acid" as used herein refers to a nucleic acid wherein at least one of the following is true: (a) the nucleic acid is foreign ("exogenous") to (that is, not naturally found in) a given host cell; (b) the nucleic acid comprises a nucleotide sequence that is naturally found in (that is, is "endogenous to") a given host cell, but the nucleotide sequence is produced in an unnatural (for example, greater than expected or greater than naturally found) amount in the cell; (c) the nucleic acid comprises a nucleotide sequence that differs in sequence from an endogenous nucleotide sequence, but the nucleotide sequence encodes the same protein (having the same or substantially the same amino acid sequence) and is produced in an unnatural (for example, greater than expected or greater than naturally found) amount in the cell; or (d) the nucleic acid comprises two or more nucleotide sequences that are not found in the same relationship to each other in nature (for example, the nucleic acid is recombinant).

"Host cell" and "microorganism" are used interchangeably herein to refer to any archae, bacterial, or eukaryotic living cell into which a heterologous nucleic acid can be or has been inserted. The term also relates to the progeny of the original cell, which may not necessarily be completely identical in morphology or in genomic or total DNA complement to the original parent, due to natural, accidental, or deliberate mutation.

"Isoprenoid" and "isoprenoid compound" are used interchangeably herein and refer to a compound derivable from isopentenyl diphosphate.

"Isolate" and "isolating" when referred to a bio-organic compound is the enrichment of the amount of the bio-organic compound in a composition. Consequently, the amount of the bio-organic compound in a composition after the bio-organic compound has been isolated or subject to an isolating step is greater than the amount present in the composition prior to such step.

"Mevalonate pathway" or "MEV pathway" is used herein to refer to the biosynthetic pathway that converts acetyl-CoA to IPP. The MEV pathway is illustrated schematically in FIG. 3.

"Naturally occurring" as applied to a nucleic acid, an enzyme, a cell, or an organism, refers to a nucleic acid, enzyme, cell, or organism that is found in nature. For example, a polypeptide or polynucleotide sequence that is present in an organism that can be isolated from a source in nature and that has not been intentionally modified by a human in the laboratory is naturally occurring.

"Optional" or "optionally" means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where the event or circumstance does not occur.

"Pyrophosphate" is used interchangeably herein with "diphosphate".

As used herein, a composition that is a "substantially pure" compound is substantially free of one or more other compounds, i.e., the composition contains greater than 80 vol. %, greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, greater than 99.9 vol. % of the compound; or less than 20 vol. %, less than 10 vol. %, less than 5 vol. %, less than 4 vol. %, less than 3 vol. %, less than 2 vol. %, less than 1 vol. %, less than 0.5 vol. %, less than 0.1 vol. %, or less than 0.01 vol. % of the one ore more other compounds, based on the total volume of the composition.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, RL and an upper limit, RU, is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

In addition to the definitions above, certain compounds described herein have one or more double bonds that can exist as either the Z or E isomer. The invention in certain embodiments encompasses these compounds as individual isomers in a substantially pure form as well as mixtures of various isomers, e.g., racemic mixtures of stereoisomer.

Apparatus for Making Bio-Organic Compounds

The present invention provides various production systems for making bio-organic compounds. In some embodiments, the bio-organic compounds may be produced using batch, continuous, fed-batch or semi-continuous fermentation processes.

Batch fermentation may be a closed system where the composition of the media is fixed at the beginning of the fermentation and not subject to artificial alterations during the fermentation. Thus, at the beginning of the fermentation the media is inoculated with the desired organism or organisms and fermentation is permitted to occur adding nothing to the system. In some embodiments, however, "batch" fermentation is batch with respect to the addition of carbon source and attempts are often made at controlling factors such as pH and oxygen concentration. In batch systems the metabolite and biomass compositions of the system may change constantly up to the time the fermentation is stopped. Within batch cultures, cells may moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the fed-batch system. Fed-batch fermentation processes are also suitable in the present invention and comprise a typical batch system with the exception that additional carbon source or substrate is added in increments as the fermentation progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$.

Continuous fermentation is an open system where a defined fermentation media is added continuously to one or more bioreactors which may be in series and an equal amount of conditioned media is removed simultaneously from the system for additional processing. Continuous fermentation generally maintains the cultures at a constant high density where cells are primarily in log phase growth. Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration is kept constant. Continuous systems strive to maintain steady state growth conditions and thus the cell loss due to media being drawn off must be balanced against the cell growth rate in the fermentation.

Accordingly, in some embodiments of the invention, a bio-organic production system is provided which comprises:

a. at least one vessel having a capacity of at least 100 liters;
b. an aqueous medium, within the at least one vessel, comprising a first phase;
c. a plurality of host cells, within the aqueous medium, capable of making, producing or synthesizing at least one bio-organic compound; and,
d. a liquid organic second phase comprising the at least one bio-organic compound in contact with the first phase.

A suitable vessel for use in the present invention can be any vessel for holding the host cells and aqueous medium for fermentation. For example, the vessel can be a tank for a reactor or fermenter or it can be a part of a centrifuge that can separate heavier materials from lighter materials in subsequent processing steps. Alternatively, one or a plurality of vessels may be used in a continuous or semi-continuous process.

A general illustrative example of a suitable vessel 100 is shown in FIG. 1. The vessel 100 includes: an inlet port 120 for the addition of host cells, fermentation media, and other compounds, nutrients or compositions to assist, regulate or improve fermentation of the host cells, production of the bio-organic compound or compounds, and performance of additional production steps into the vessel; an outlet port 130 for removing the materials during or at the end of the fermentation process, and a gas outlet 140 for venting off exhaust gases such as carbon dioxide produced during or after the fermentation process. Vessel 100 may be completely filled with host cells, fermentation media and other materials so that there is no space for gas at the top of the vessel. Alternatively, vessel 100 can be partially filled thus leaving void space occupied by a gas. The amount, pressure and composition of the gas in the void space may be controlled to optimize or maximize growth of the host cells and production of the bio-organic compound or bio-organic compounds. For example, during fermentation of aerobic host cells, the gas typically may comprise air or other oxygen-containing gas at various pressures above, at or below atmospheric pressure, for example for microaerophilic and nanaerobic host cells the oxygen concentration of the gas may be controlled within a range lower than atmospheric concentration while still above zero while during fermentation for anaerobic host cells, the gas typically has little to no oxygen and can completely comprise mostly or completely of nitrogen or other suitable gas.

In a closed system, inlet port 120, outlet port 130 and gas outlet 140 of vessel 100 shown in FIG. 1 may be closed or under positive pressure during the fermentation process. Alternatively, particularly when using aerobic host cells, vessel 100 can be used as an open system whereby one or more of the ports and outlet are opened to the atmosphere providing a system for gas/liquid mass transfer (air or oxygen in and carbon dioxide out). If desired, gas outlet 140 may function both as a gas outlet and as a gas inlet where oxygen or air or other gas may be introduced into the system. In some embodiments, vessel 100 includes separate gas inlets and separate gas outlets. In such open systems, additional hardware may be included on the vessel for preventing contamination or infiltration of other organisms or other materials into the vessel during the fermentation.

Figure 2:
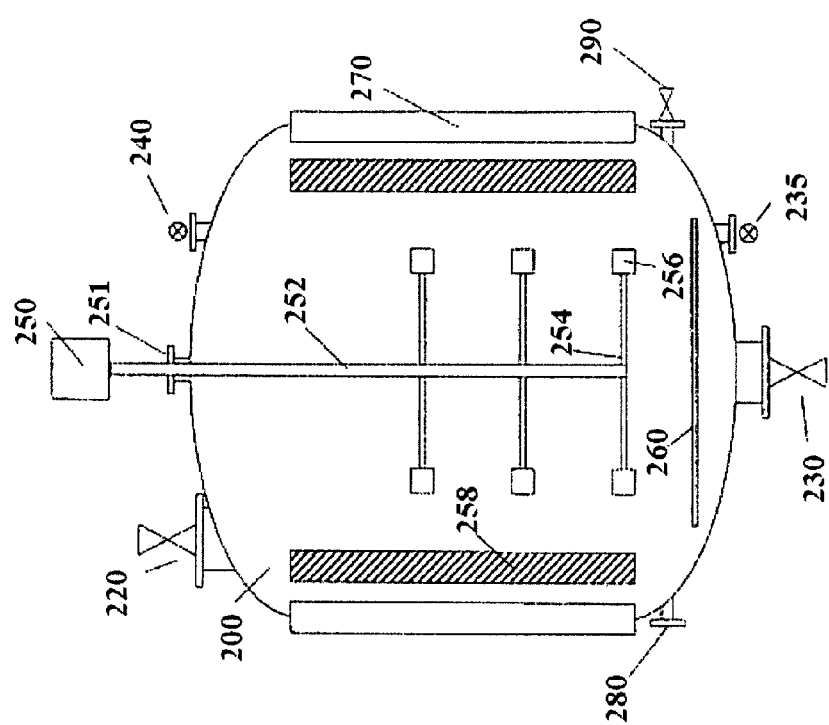
FIG. 2 is another vessel embodiment.

Another vessel embodiment is illustrated in FIG. 2. In addition to inlet port 220, outlet port 230, gas inlet 235, and gas outlet 240 similar to the vessel in FIG. 1, the vessel 200 of FIG. 2 includes an agitator 250 for mixing. In some embodiments, agitator 250 may comprise a motor-driven shaft 252 which may include a shaft seal 251 and is connected to one or more impellers 254. Agitator 250 may be typically attached to the top or bottom of the vessel 200. Optionally, each impeller 254 may be terminated with one or more paddles 256. Impellers 254 may be any suitable shape and may be selected specifically to control amount of mixing, growth rate of the host cells, production rate of the bio-organic compound, shear rate and oxygen or other gas transfer rates. Additionally, one or more baffles 258 can be added to the vessel 200 to further improve mixing. In another embodiment, agitation may be supplied in the form of a recycle line with a pump that draws material from one portion of the vessel such as the bottom and reintroduces the material into the vessel at another portion of the vessel such as the top. Agitation within the vessel of the host cells and the fermentation medium aids in ensuring that the host cells are exposed to adequate nutrients to enable them to grow and produce the bio-organic compounds.

If the fermentation process is an aerobic process, oxygen or air can be bubbled through a sparger 260 for improved gas/liquid mass transfer. The sparger 260 may include one or more gas outlets (not shown) that are submerged within the fermentation media, preferably at or near the bottom of the vessel. In some embodiments, the sparger 260 may be a sparging ring having multiple gas outlets arranged in a generally circular or round configuration. Alternatively, for shear sensitive organisms or to reduce foaming, passive aeration of the vessel may be provided, such as use of various aeration screens, membranes, fibers or other passive aeration devices or by removing a portion of the media from the vessel, oxygenating it and returning it to the vessel.

If temperature control is desired, then a heater or heat exchanger may be used to heat or cool the fermentation reaction. In one embodiment, the temperature may be controlled using a heating/cooling jacket 270 surrounding and/or attached to at least a portion of vessel 200 that may be connected to a heat exchanger (not shown) that circulates temperature controlled heat exchange fluid through jacket 270. Alternatively, a heater, or heat exchanger may be immersed in the fermentation medium. Illustrative examples of this type of heater or heat exchanger include an electric immersion heater, an immersed coiled or linear tube heat exchanger carrying a heat-exchange fluid such as heated water or oil, and one or more spargers that inject a heated stream such as air and/or water into the fermentation medium. Alternatively or additionally, a heater or heat exchanger can be attached to the outside of the vessel. Such heaters and heat exchangers include electrical heat tape on outside sidewalls of the vessel and heated or jacketed recycle lines attached to the vessel.

Vessel 200 can include additional inlet and outlet ports. In some embodiments, the additional inlet and outlet ports may be located on the top, sides or bottom of the vessel 200. In some embodiments, the additional inlet ports include feed lines for the addition of oxygen or other gases, nutrients, foam and pH control agents during the fermentation reaction. Any of the inlet and outlet ports may include sterilization mechanisms for multiple uses including in-process use, and multiple connection or reconnection during the fermentation process.

In addition, one or more probe ports 280 and/or sampling valves 290 can be positioned at various places on vessel 200 to help monitor critical parameters such as concentrations of various products and metabolites, pH, liquid level, pressure, foam, dissolved oxygen concentration, temperature, agitation rate, power, voltage, valve positions and cell density during the fermentation process.

It should be understood that the vessels in FIGS. 1 and 2 are for illustrative purposes and that many different vessel configurations for the fermentation process may be used, for example, according to the type of host cell, the bio-organic compound or compounds produced, the production volume, the type of fermentation process, the type of downstream processing, the separation process and other considerations.

A vessel such as that shown in FIG. 2 is suitable for use in batch fermentation processes. If a continuous or semi-continuous fermentation process is desired (as opposed to a batch fermentation process) where materials are constantly added to or withdrawn from the vessel, the vessel typically includes additional inlet and outlet ports which may be located on the top, bottom or on the sides of the vessel. These additional inlet and outlet ports facilitate the flow of materials in and out of the vessel. In some embodiments, one or more vessels continuously receive host cells, fermentation medium, and optional additives while continuously discharging host cells, byproducts, and/or bio-organic compounds from the vessels. In these embodiments, the discharge from one vessel may be used as the feedstock to another vessel that optionally also receives fresh host cells, fermentation medium, nutrients, and/or other additives. A single vessel or a series of vessels together can be configured to provide the desired average residence time for the host cells. A portion of the discharge from one of the downstream vessels can be returned to one or more upstream vessels to recycle the discharge to an earlier stage of processing, or other materials from processing steps further downstream can be reintroduced into the vessels.

The vessels used in some embodiments of the present invention include additional hardware that may be attached to the vessel to facilitate processing. Such hardware may include additional hardware for facilitating clean-in-place and sterilize-in-place processing. In some embodiments, one, some or each of the ports, outlets, inlets, valves and all of the hardware inside the vessel may be sterilized in place. In some embodiments, the sterilization may occur using steam sterilization. For example, any of the ports, outlets or sampling valves may include or have attached to them additional hardware that provides for steam supply to and condensate return from the port outlet or valve such that it may be steam sterilized prior to use or reuse.

The vessel or vessels may have a capacity of at least 100 liters. In some embodiments, the vessel has a capacity of from 100 to 3,000,000 liters such as at least 1000 liters, at least 5,000 liters, at least 10,000 liters, vessel at least 25,000 liters, at least 50,000 liters, at least 75,000 liters, at least 100,000 liters, at least 250,000 liters, at least 500,000 liters or at least 1,000,000 liters.

The vessel or vessels may include or have attached to them sensors and probes for measuring various parameters such as pressure, pH, dissolved oxygen concentration, temperature, gas flow rates, liquid flow rates, liquid level, valve positions, foaming, agitation, power, voltage and any other parameters useful in controlling or optimizing the growth of the host cells and the production of the bio-organic compound or compounds. The sensors and probes may feed information to one or more automated systems for controlling and recording the various parameters measured and for adjusting any of the various parameters by controlling air flowrates, power, heating or cooling to control vessel temperature, stirring rpms, pumps, sterilization or clean in place of the vessel or any of the inlet, outlet, addition, sampling valves or other ports, outlet flow control or any other relevant mechanism for controlling a parameter or parameters of the fermentation. Such adjustments may occur using any known control mechanism, such as for example, control or actuation of various valves, pumps or motors and may use proportional, proportional-integral or proportional-integral-derivative control systems.

The automated system or systems may additionally be controlled and monitored by a central control system, which may be a local or plant wide control system and may control production of just one bio-organic compound production process or multiple bio-organic compound production processes. The automated system or systems and central control system may comprise any suitable software, firmware and/or hardware, which may be proprietary or off the shelf or a combination thereof and may communicate using any suitable communication system. Non-limiting examples of such communication systems include hardwired systems that may be digital or analog, and may include direct connection or be in the form of a network such as a LAN or a WAN or ethernet. In addition, in some embodiments the communication system may be wireless and may be proprietary, BLUETOOTH, ultra wide band, 802.11a,b,g or n or ZigBee, including TDMA, FDMA, OFDM, and CDMA and may operate in any suitable frequency band such as 2.4 GHz or 5.8 GHz.

Any of the vessels used in the production of the bio-organic compounds may include additional hardware, such as additional agitators, additional inlet ports, outlet ports, sampling ports, additional heating/cooling equipment, such as additional heating coils, additional aeration equipment such as additional spargers, additional sensors and probes, additional cleaning or sterilization equipment to facilitate processing or any other parameter of the fermentation.

In some embodiments of the invention, an isoprenoid production system is provided which comprises:
  a. at least one vessel having a capacity of at least 100 liters;
  b. an aqueous medium, within the at least one vessel, comprising a first phase;
  c. a plurality of host cells, within the aqueous medium, capable of making, producing or synthesizing one or more isoprenoid compounds; and,
  d. a liquid organic second phase comprising the one or more isoprenoid compounds in contact with the first phase.

In some embodiments, the isoprenoid compound or compounds is a $C_5$ isoprenoid. These compounds are derived from one isoprene unit and are also called hemiterpenes. An illustrative example of a hemiterpene is isoprene. In other embodiments, the isoprenoid compound or compounds is a $C_{10}$ isoprenoid. These compounds are derived from two isoprene units and are also called monoterpenes. An illustrative example of a monoterpene is myrcene. In other embodiments, the isoprenoid compound or compounds is a $C_{15}$ isoprenoid. These compounds are derived from three isoprene units and are also called sesquiterpenes. An illustrative example of a sesquiterpene is patchoulol (which is also known as patchouli alcohol). In other embodiments, the isoprenoid compound or compounds is a $C_{20}$ isoprenoid. These compounds are derived from four isoprene units and also called diterpenes. An illustrative example of a diterpene is taxadiene. In yet other examples, the isoprenoid compound or compounds is a $C_{20+}$ isoprenoid. These compounds are derived from more than four isoprene units and include: triterpenes ($C_{30}$ isoprenoid compounds derived from 6 isoprene units) such as squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. In some embodiments, the isoprenoid compound or compounds may be any combination of two or more isoprenoid compounds.

In another aspect of the present invention, a method for producing at least one bio-organic compound is provided which comprises:
a. culturing in an aqueous medium a plurality of host cells that produce, make or synthesize at least one bio-organic compound wherein the aqueous medium comprises a first phase;
b. forming a liquid organic second phase comprising the at least one bio-organic compound in contact with the first phase;
c. separating at least a portion of the second phase from the first phase; and,
d. isolating the at least one bio-organic compound from the second phase.

The isoprenoid production system may include one or more additional processing components including: 1) one or more separation systems for separating the at least one bio-organic compound from the aqueous media and the organic second phase; 2) one or more reactors for biologically or chemically altering the at least one bio-organic compound such as by addition, substitution, hydrogenation, alkylation, hydroxylation, condensation, halogenation or any other suitable reaction; 2) one or more blending vessels or systems for blending the at least one bio-organic compound with one or more additional components; 3) and one or more additional purification or separation systems for further purifying the bio-organic composition or the at least one bio-organic compound.

The second phase may comprise the at least one bio-organic compound. The bio-organic compound can form a portion, most, or substantially all of the second phase. In certain embodiments, the bio-organic compound forms 1% to 99%, such as 5% to 95%, 10% to 90%, 20% to 80%, 25% to 75%, 35% to 65%, or 40% to 50% of the second phase. In certain embodiments, the second phase comprises at least 90% bio-organic compound. In certain embodiments, the second phase consists essentially of the bio-organic compound.

In some embodiments, the plurality of host cells includes more than one type of host cell, such as more than one species or strain of host cells, for example 2-5 species or strains of host cells, for example 2, 3, 4 or 5 species or strains of host cells. In some embodiments the plurality of host cells may produce more than one bio-organic compound, such as 2-5 bio-organic compounds, for example 2, 3, 4, or 5 bio-organic compounds.

The bio-organic compound or compounds may be isolated from the first phase and/or second phase using any suitable separation method. In some embodiments, the bio-organic compound is isolated from the second phase such that it is substantially pure.

In some embodiments, the organic second phase occurs spontaneously as a result of chemical and molecular interactions such as differences in solubility, or hydrophobicity, density, concentration or any other spontaneous phase separation mechanism. In other embodiments, separation of the first and second phases is induced in a separation vessel or vessels or system that may be the same or a different vessel or vessels or processing system as the fermentation vessel or vessels. In some embodiments, phase separation is induced by centrifugation such as continuous or batch centrifugation. In other embodiments, phase separation is induced by the introduction of a deemulsifier or a nucleating agent into the fermentation reaction. A deemulsifier prevents or limits the amount of the bio-organic compound or compounds that emulsify with the aqueous phase. Illustrative examples of deemulsifiers include flocculants and coagulants. A nucleating agent facilitates the aggregation of smaller droplets of the bio-organic compound to coalesce and eventually form a separate phase. If sufficient amounts of a nucleating agent are used, the nucleating agent itself forms an organic second phase into which the bio-organic compound migrates. Illustrative examples of nucleating agents include droplets of the bio-organic compound or compounds itself and organic solvents such as dodecane, isopropyl myristrate, and methyl oleate. Some embodiments may include a combination of one or more of the above phase separation materials and methods.

Once phase separation occurs, the separate phases can be individually drawn from the separation vessel. Any amount of the second phase can be separated from the first phase, e.g. all, a portion, 1% to 100% such as 5% to 95%, 10% to 90%, 20% to 80%, 25% to 75%, 35% to 65%, or 40% to 50% of the second phase may be separated from the first phase. If the organic second phase is less dense than the aqueous first phase, then one or more taps can be provided or placed on the separation vessel near the interface between the two phases (preferably within the organic second phase) to decant the organic second phase before removing the denser aqueous phase. Alternatively, the aqueous first phase can be removed from the separation vessel using an outlet near the bottom of the separation vessel until the organic second phase appears. At which point, the organic second phase can be transferred into a separate location for further processing or storage. Both of the aqueous first and organic second phases can flow out of the separation vessel under the force of gravity, gas pressure or through the use of a pump or pumps or a combination thereof.

If the organic second phase is denser than the aqueous first phase, then one or more taps can be provided or placed on the separation vessel near the interface between the two phases (preferably within the organic second phase) to decant the aqueous first phase before removing the denser organic second phase. Alternatively the organic second phase may be removed from the separation vessel using an outlet near the bottom of the separation vessel.

For a continuous process in which the aqueous first phase is denser than the organic second phase, a separation vessel with one or more taps can contain a specified volume of the fermentation medium and host cells, and the continually-produced organic second phase may be decanted through the taps to storage or further processing. If the organic second phase is denser than the aqueous first phase, the organic second phase can be removed continuously from the bottom of the separation vessel at a rate that prevents complete depletion of the organic second phase from the separation vessel to avoid drawing from the aqueous first phase.

In some embodiments, the bio-organic compound may be isolated from the organic second phase using adsorption, a process in which molecules move from a bulk liquid onto the surface of adsorbents. Illustrative examples of adsorbents include activated carbon; aluminas; aluminosilicates such as zeolites; clays such as fuller's earth; molecular sieves; organic polymers such as polystyrene and resins; and silicas such silica gel. Depending on the adsorbent used, the adsorbent may be used to capture the desired bio-organic product or unwanted byproducts. Isolation by adsorption may be performed using a batch, continuous or semi-continuous process.

In other embodiments, the bio-organic compound may be isolated from the organic second phase using distillation, a method of separating substances based on differences in their volatilities. In batch distillation, an entire batch of liquid is initially charged to a vessel and then heated or reduced in pressure within the vessel. Vapor is thereby continuously generated and may be condensed to form a liquid distillate which is collected. In continuous equilibrium distillation, a continuously flowing liquid feed is heated or reduced in pressure so as to cause partial vaporization of the mixture and separate recovery of liquid and vapor components. The liquid and vapor disengage while flowing through a distillation column, and the products emerge as vapor and liquid streams. When the vapor and liquid approach phase equilibrium, this is called a flashing process. If desired, the vapor product can be condensed to form a liquid distillate.

In other embodiments, the bio-organic compound or compounds are isolated from the organic second phase using gas-liquid extraction. This process is also known as stripping and is the transfer of a component dissolved in a liquid stream into a vapor stream in a more concentrated form. Temperature and pressure can be optimized for the transfer of the desired bio-organic compound. Illustrative examples of vapor streams include air and steam. Typically, the liquid stream flows down a column while the vapor stream is bubbled up (flowing countercurrently to the liquid stream).

In other embodiments, the bio-organic compound is isolated from the organic second phase using liquid-liquid extraction. Also known as solvent extraction, liquid-liquid extraction is the transfer of a substance from one liquid phase into another immiscible liquid phase.

In a batch liquid-liquid extraction system, the feed liquid (the organic second phase) is mixed with a second immiscible liquid phase in a suitable vessel. The mixture is then permitted to settle into layers and separate into extract and raffinate and the lighter layer can be decanted from the vessel. The desired bio-organic compound or compounds can be in the extract or raffinate depending on the product and solvent used.

In a continuous liquid-liquid extraction system, differences in density, vapor pressure at a given temperature, or boiling points are used to separate the desired bio-organic product from the feed liquid (the organic phase). Such systems can use mixer/settler tanks, towers or columns, centrifuges and combinations thereof to effect separation.

In other embodiments, the bio-organic compound is isolated from the organic second and/or the aqueous first phase using ultrafiltration, a pressure-driven membrane process used to separate solution components on the basis of molecular size and shape. Under an applied pressure difference across an ultrafiltration membrane, solvent and small solute species pass through the membrane and are collected as permeate while larger solute species are retained by the membrane and recovered as a concentrated retentate. Ultrafiltration involves solutes whose molecular dimensions are ten or more times larger than those of the solvent and are usually below ½ micron in size. The solutes or the materials to be separated usually have molecular weights greater than 500 amu, such as macromolecules, colloidal dispersions, and emulsions. A non-limiting example of an ultrafiltration system is a tangential flow ultrafiltration system.

In some embodiments, the host cells are capable of producing from about 10 to about 50 grams, more than about 15 grams, more than about 20 grams, more than about 25 grams or more than about 30 grams of bio-organic compound per liter of fermentation medium.

In some embodiments, the host cells are capable of producing from about 50 to about 1500 milligrams, such as more than about 100 milligrams, more than about 150 milligrams, more than about 200 milligrams, more than about 250 milligrams, more than about 500 milligrams, more than about 750 milligrams or more than about 1000 milligrams of bio-organic compound per gram of dry cell weight.

Fuel Composition Production System

In some embodiments, the invention comprises a fuel composition production system comprising:
 a. at least one vessel having a capacity of at least 100 liters;
 b. an aqueous medium, within the vessel, comprising a first phase;
 c. a plurality of host cells, within the aqueous medium, capable of making, producing or synthesizing at least one bio-organic compound; and,
 d. a liquid organic second phase comprising the at least one bio-organic compound in contact with the first phase.

The fuel composition production system may include one or more additional processing components including: 1) one or more separation systems for separating the at least one bio-organic compound from the aqueous media and the organic second phase; 2) one or more reactors for biologically or chemically altering the at least one bio-organic compound such as by addition, substitution, hydrogenation, alkylation, hydroxylation, condensation, halogenation or any other suitable reaction; 2) one or more blending vessels or systems for blending the at least one bio-organic compound with one or more additional fuel components such as a petroleum-based fuel, a fuel additive or a combination thereof; and, 3) one or more additional purification or separation systems for further purifying the fuel composition or the at least one bio-organic compound.

In some embodiments, the fuel additive is selected from the group consisting of oxygenates, antioxidants, environmental protectants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, deemulsifiers, dyes, markers, static dissipaters, biocides and combinations thereof.

In some embodiments, the fuel composition production system comprises:
 a) one or more batch, fed-batch or continuous flow fermentation systems comprising:
  i) at least one vessel having a capacity of at least 100 liters;
  ii) an aqueous medium, within the at least one vessel, comprising a first phase;
  iii) a plurality of host cells, within the aqueous medium, capable of making, producing or synthesizing at least one bio-organic compound; and,
  iv) a liquid organic second phase comprising the at least one bio-organic compound in contact with the first phase;
 b) one or more first phase separation systems whereby the first phase and the second organic phase or one or more components of the second organic phase are separated;
 c) optionally one or more second phase separation systems whereby the at least one bio-organic compound is separated from the second organic phase;
 d) optionally one or more reactors or vessels wherein the at least one bio-organic compound is chemically or biologically modified;

e) optionally one or more purification systems whereby the bio-organic compound or the modified bio-organic compound is purified or further purified;
f) optionally one or more blending vessels or systems for blending the at least one bio-organic compound with one or more additional fuel components; and
g) optionally one or more further purification systems whereby the blend of the at least one bio-organic compound and the one or more additional fuel components is purified or further purified.

In some embodiments, the one or more first phase separation systems comprises one or more systems, vessels or other phase separation components detailed herein configured specifically to separate the first phase from the second organic phase. In some embodiments the one or more second phase separation systems includes one or more systems, vessels or phase separation components detailed herein configured specifically to separate the bio-organic compound or compounds from the second organic phase.

In some embodiments, the one or more reactors wherein the at least one bio-organic compound is chemically or biologically modified comprises the same or different vessel or vessels used for the fermentation or the separation systems. Alternatively, the one or more reactors may comprises one or more different vessels, which may include additional hardware, sensors, ports, probes, and/or control systems suitable for the specific reaction or reactions or other modifications to the bio-organic compound or compounds that are performed therein. The reactors may be batch, fed batch or continuous reactors.

In some embodiments, the bio-organic compounds or modified bio-organic compounds or the fuel compositions may be purified or further purified using one or more purification systems. The purification systems may comprise any suitable purification system including any system that may remove unwanted compounds from the bio-organic compound or compounds or that may separate the unwanted compounds from the bio-organic compounds. In some embodiments, the purification system may comprise one or more systems, vessels or phase separation components detailed herein that may be specifically configured to achieve the desired purity of the bio-organic compound or compounds. In some embodiments, the purification may be accomplished using one or more separation systems in series to achieve the desired purity. In some embodiments, the separation systems may be configured differently from each other in order to achieve the purity in stepwise fashion.

In some embodiments, the purification will be performed to achieve specifications or requirements of federal, state or local laws, rules or regulations for the bio-organic compounds or for fuel compositions. In some embodiments, the purification can improve the functionality of the bio-organic compounds or fuel compositions beyond the requirements of federal or state laws, rules or regulations. In some embodiments, the federal state or local laws, rules or regulations may pertain to environmental emissions, fuel performance, tax incentives, and other economic incentives. In some embodiments, the purification may reduce the environmental impact of, carbon footprint of, fuel efficiency obtained from, reliability obtained from, energy available from, or long term economic cost of the bio-organic compounds or fuel compositions.

In some embodiments the fuel composition system includes one or more blending vessels or systems for blending the at least one bio-organic compound with one or more additional fuel components. The blending vessel or blending system may be any suitable vessel or system. The blending vessel may include any or all of the inlets, outlets, ports, sensors, probes, agitators and other hardware identified for the bio-organic compound production vessel. The blending vessel may blend one or more fuel components with the bio-organic compound or compounds. For example, 2-5 fuel components, such as 3 or 4 fuel components. The blending system may be batch, continuous or fed batch.

In some embodiments, the invention comprises a method of making a fuel composition comprising:
a. culturing in an aqueous medium a plurality of host cells that produce, make or synthesize at least one bio-organic compound wherein the aqueous medium comprises a first phase;
b. forming a liquid organic second phase comprising the at least one bio-organic compound in contact with the first phase;
c. separating at least a portion of the second phase from the first phase;
d. isolating the at least one bio-organic compound from the second phase;
e. optionally chemically or biologically modifying the at least one bio-organic compound;
f. optionally purifying the bio-organic compound or the modified bio-organic compound;
g. optionally blending the at least one bio-organic compound with one or more additional fuel components; and
g) optionally purifying the blend of the one or more bio-organic compounds and the one or more additional fuel components.

In some embodiments, the fuel composition comprises a biofuel composition. In some embodiments, the biofuel further comprises at least one bio-organic compound and a petroleum-based fuel, a fuel additive or a combination thereof. In further embodiments, the petroleum-based fuel is a gasoline, jet fuel, kerosene, diesel fuel or a combination thereof.

In some embodiments, the bio-organic compound production system or the fuel composition production system may be built or created by retrofitting an ethanol production facility.

In some embodiments, the fuel composition production systems may comprise one or more automated control systems. The automated control systems may be the same or different from the control systems for the bio-organic production system and may comprise various sensors, probes and other equipment for measuring and controlling the various process parameters associated with each system within the fuel composition system and each step or the fuel composition production methods. The automated system or systems may additionally be controlled and monitored by a central control system, which may be a local or plant wide control system and may control production of just one bio-organic compound production process or multiple bio-organic compound production processes. The automated system or systems and central control system may comprise any suitable software, firmware and/or hardware, which may be proprietary or off the shelf or a combination thereof and may communicate using any suitable communication system. Non-limiting examples of such communication systems include hardwired systems that may be digital or analog, and may include direct connection or be in the form of a network such as a LAN or a WAN or ethernet. In addition, in some embodiments the communication system may be wireless and may be proprietary, BLUETOOTH, ultra wide band, 802.11a,b,g or n or ZigBee, including TDMA, FDMA, Host Cells Any suitable host cell can be used in the practice of the present invention. In some embodiments, the host cell is a genetically modified host microorganism in which nucleic acid molecules have been inserted, deleted or modified (i.e., mutated; e.g., by insertion, deletion, substitution, and/or inversion of nucleotides), to either produce the desired bio-organic compound, or effect an increased yield of the desired bio-organic compound.

Illustrative examples of suitable host cells include any archae, bacterial, or eukaryotic cell. Examples of archae cells include, but are not limited to those belonging to the genera: *Aeropyrum, Archaeglobus, Halobacterium, Methanococcus, Methanobacterium, Pyrococcus, Sulfolobus,* and *Thermoplasma*. Illustrative examples of archae species include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum, Thermoplasma volcanium.*

Examples of bacterial cells include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus,* Strepromyces, Synnecoccus, and *Zymomonas*.

Illustrative examples of bacterial species include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus,* and the like.

In general, if a bacterial host cell is used, a non-pathogenic strain is preferred. Illustrative examples of species with non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum,* and the like.

Examples of eukaryotic cells include but are not limited to fungal cells. Examples of fungal cells include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

Illustrative examples of eukaryotic species include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia piperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*).

In general, if a eukaryotic cell is used, a non-pathogenic strain is preferred. Illustrative examples of species with non-pathogenic strains include but are not limited to: *Fusarium graminearum, Fusarium venenatum, Pichia pastoris, Saccaromyces boulardi,* and *Saccaromyces cerevisiae.*

In some embodiments, the host cells of the present invention have been designated by the Food and Drug Administration as GRAS or Generally Regarded As Safe. Illustrative examples of such strains include: *Bacillus subtilis, Lactibacillus acidophilus, Lactobacillus helveticus,* and *Saccharomyces cerevisiae.*

Engineering Pathways to Make Bio-Organic Compounds

An illustrative example of a class of bio-organic compounds is isoprenoids. They comprise a diverse family of over 40,000 individual products, many of which are vital to living organisms. Isoprenoids serve to maintain cellular fluidity, electron transport, and other metabolic functions. In addition to their usefulness in making fuel compositions, a vast number of natural and synthetic isoprenoids are useful as pharmaceuticals, cosmetics, perfumes, pigments and colorants, fungicides, antiseptics, nutraceuticals, and fine chemical intermediates.

Isoprenoid compounds are made in nature through two different metabolic pathways which converge at IPP and its isomer, DMAPP. In general, eukaryotes other than plants use the MEV isoprenoid pathway exclusively to convert acetyl-CoA to IPP, which is subsequently isomerized to DMAPP. Prokaryotes, with some exceptions, use the mevalonate-independent or DXP pathway to produce IPP and DMAPP separately through a branch point. In general, plants use both the MEV and DXP pathways for IPP synthesis. The methods described herein for engineering the MEV and DXP pathways to make the desired isoprenoid compound can be readily adapted to similarly engineer other pathways to make other bio-organic compounds.

MEV Pathway

Figure 3:
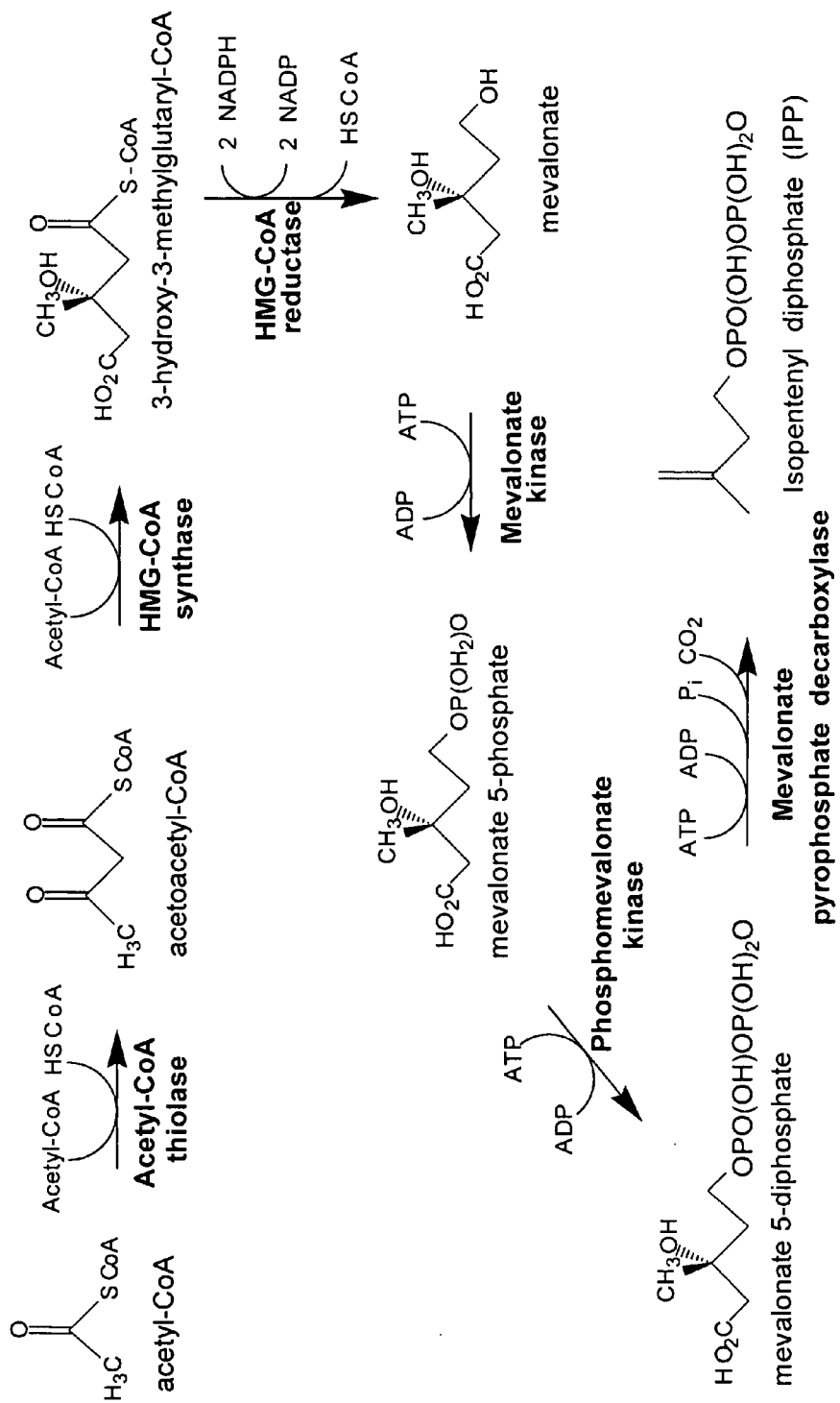
FIG. 3 is a schematic representation of the mevalonate ("MEV") pathway for the production of isopentenyl diphosphate ("IPP").

A schematic representation of the MEV pathway is described in FIG. 3. In general, the pathway comprises six steps.

In the first step, two molecules of acetyl-coenzyme A are enzymatically combined to form acetoacetyl-CoA. An enzyme known to catalyze this step is, for example, acetyl-CoA thiolase (also known as acetyl-CoA acetyltransferase). Illustrative examples of nucleotide sequences include but are not limited to the following GenBank accession numbers and the organism from which the sequences derived: (NC_000913 REGION: 2324131 . . . 2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora gris-*

*eola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Illustrative examples of nucleotide sequences include but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315 . . . 713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

If IPP is to be converted to DMAPP, then a seventh step is required. An enzyme known to catalyze this step is, for example, IPP isomerase. Illustrative examples of nucleotide sequences include but are not limited to: (NC_000913, 3031087 . . . 3031635; *Escherichia coli*), and (AF082326; *Haematococcus pluvialis*). If the conversion to DMAPP is required, an increased expression of IPP isomerase ensures that the conversion of IPP into DMAPP does not represent a rate-limiting step in the overall pathway.

DXP Pathway

Figure 4:
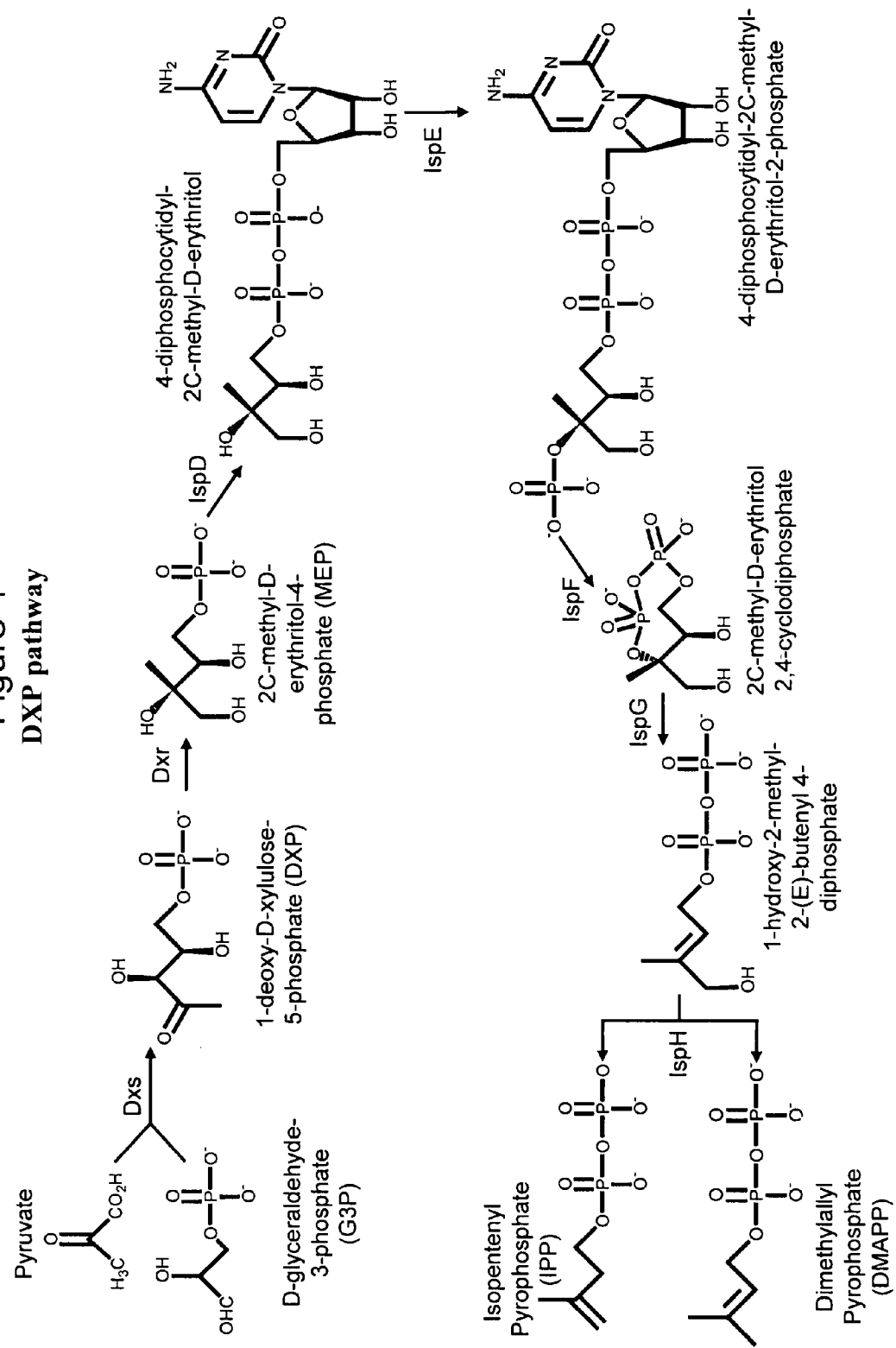
FIG. 4 is a schematic representation of the DXP pathway for the production of IPP and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

A schematic representation of the DXP pathway is described in FIG. 4. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PP0527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD 1293; *Xylella fastidiosa Temecula1*), and (NC 003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus_tag RSP_2835; *Rhodobacter sphaeroides* 2.4.1), (NC_003071, locus tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300; *Escherichia coli*) and (NC_007493, locus_tag RSP_1779; *Rhodobacter sphaeroides* 2.4.1).

In the fifth step, 4-diphosphocytidyl-2C-methyl-D-erythritol-2-phosphate is converted to 2C-methyl-D-erythritol 2, 4-cyclodiphosphate. An enzyme known to catalyze this step is, for example, 2C-methyl-D-erythritol 2, 4-cyclodiphosphate synthase. Illustrative examples of nucleotide sequences include but are not limited to: (AF230738; *Escherichia coli*), (NC_007493, locus_tag RSP_6071; *Rhodobacter sphaeroides* 2.4.1), and (NC_002947, locus_tag PP1618; *Pseudomonas putida* KT2440).

In the sixth step, 2C-methyl-D-erythritol 2, 4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC_002947, locus_tag PP0853; *Pseudomonas putida* KT2440), and (NC_007493, locus_tag RSP_2982; *Rhodobacter sphaeroides* 2.4.1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC_002947, locus_tag PP0606; *Pseudomonas putida* KT2440).

In some embodiments, "cross talk" (or interference) between the host cell's own metabolic processes and those processes involved with the production of IPP as provided by the present invention are minimized or eliminated entirely. For example, cross talk is minimized or eliminated entirely when the host microorganism relies exclusively on the DXP pathway for synthesizing IPP, and a MEV pathway is introduced to provide additional IPP. Such host organisms would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the naturally occurring DXP pathway enzymes.

In other embodiments, the host cell produces IPP via the DXP pathway, either exclusively or in combination with the MEV pathway. In other embodiments, a host's MEV pathway is functionally disabled so that the host cell produces IPP exclusively through a heterologously introduced DXP pathway. The MEV pathway can be functionally disabled by disabling gene expression or inactivating the function of one or more of the naturally occurring MEV pathway enzymes.

$C_5$ Compounds

Exemplary $C_5$ bio-organic compounds are hemiterpenes which are generally are derived from IPP or DMAPP. An illustrative example of a hemiterpene is isoprene.

Isoprene

Isoprene, whose structure is

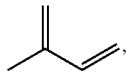

is found in many plants. Isoprene is made from IPP by isoprene synthase. Illustrative examples of suitable nucleotide sequences include but are not limited to: (AB198190; *Populus alba*) and (AJ294819; *Polulus alba×Polulus tremula*).

$C_{10}$ Compounds

Exemplary $C_{10}$ bio-organic compounds are monoterpenes which are generally derived from geranyl pyrophosphate (GPP) which in turn is made by the condensation of IPP with DMAPP. An enzyme known to catalyze this step is, for example, geranyl pyrophosphate synthase.

Figure 5:
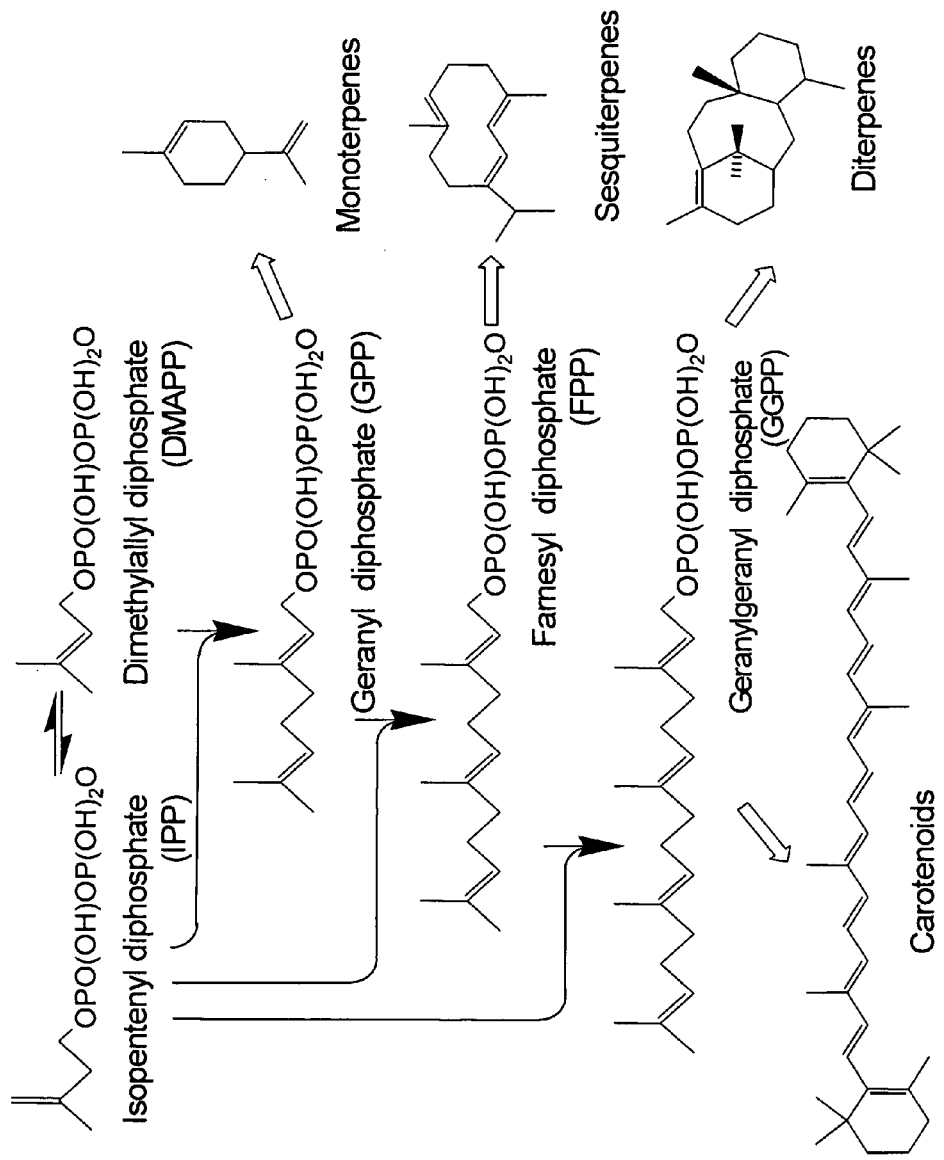
FIG. 5 is a schematic representation of the conversion of IPP and DMAPP to geranyl pyrophosphate ("GPP"), farnesyl pyrophosphate ("FPP"), and geranylgeranyl pyrophosphate ("GGPP").

FIG. 5 shows schematically how IPP and DMAPP can produce GPP, which can be further processed to a monoterpene.

Illustrative examples of nucleotide sequences for geranyl pyrophosphate synthase include but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus API11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha×piperita*), (AF182827; *Mentha×piperita*), (MPI249453; *Mentha×piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

GPP is then subsequently converted to a variety of $C_{10}$ compounds. Illustrative examples of $C_{10}$ compounds include but are not limited to:

Carene

Carene, whose structure is

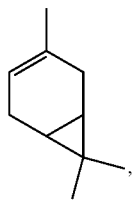

is found in the resin of many trees, particularly pine trees. Carene is made from GPP from carene synthase. Illustrative examples of suitable nucleotide sequences include but are not limited to: (AF461460, REGION 43 . . . 1926; *Picea abies*) and (AF527416, REGION: 78 . . . 1871; *Salvia stenophylla*).

Geraniol

Geraniol (also known as rhodnol), whose structure is

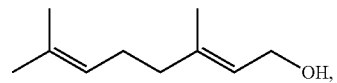

is the main component of oil-of-rose and palmarosa oil. It also occurs in geranium, lemon, and citronella. Geraniol is made from GPP by geraniol synthase. Illustrative examples of suitable nucleotide sequences include but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*)

Linalool

Linalool, whose structure is

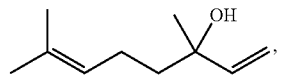

is found in many flowers and spice plants such as coriander seeds. Linalool is made from GPP by linalool synthase. Illustrative examples of a suitable nucleotide sequence include but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM_463918, Locus XP_463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. *crispa* cultivar No. 79).

Limonene

Limonene, whose structure is

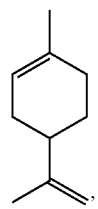

is found in the rind of citrus fruits and peppermint. Limonene is made from GPP by limonene synthase. Illustrative examples of suitable nucleotide sequences include but are not limited to: (+)-limonene synthases (AF514287, REGION: 47 ... 1867; *Citrus limon*) and (AY055214, REGION: 48 ... 1889; *Agastache rugosa*) and (−)-limonene synthases (DQ195275, REGION: 1 ... 1905; *Picea sitchensis*), (AF006193, REGION: 73 ... 1986; *Abies grandis*), and (MHC4SLSP, REGION: 29 ... 1828; *Mentha spicata*).

Myrcene

Myrcene, whose structure is

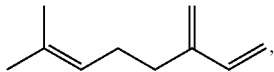

is found in the essential oil in many plants including bay, verbena, and myrcia from which it gets its name. Myrcene is made from GPP by myrcene synthase. Illustrative examples of suitable nucleotide sequences include but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

Ocimene

α- and β-Ocimene, whose structures are

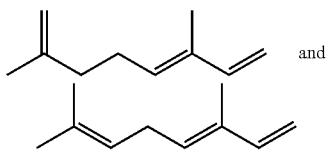

respectively, are found in a variety of plants and fruits including *Ocimum basilicum* and is made from GPP by ocimene synthase. Illustrative examples of suitable nucleotide sequences include but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_13483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

α-Pinene

α-Pinene, whose structure is

is found in pine trees and *eucalyptus*. α-Pinene is made from GPP by α-pinene synthase. Illustrative examples of suitable nucleotide sequences include but are not limited to: (+) α-pinene synthase (AF543530, REGION: 1 ... 1887; *Pinus taeda*), (−)α-pinene synthase (AF543527, REGION: 32 ... 1921; *Pinus taeda*), and (+)/(−)α-pinene synthase (AGU87909, REGION: 6111892; *Abies grandis*).

β-Pinene

β-Pinene, whose structure is

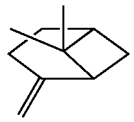

is found in pine trees, rosemary, parsley, dill, basil, and rose. β-Pinene is made from GPP by β-pinene synthase. Illustrative examples of suitable nucleotide sequences include but are not limited to: (−) β-pinene synthases (AF276072, REGION: 1 ... 1749; *Artemisia annua*) and (AF514288, REGION: 26 ... 1834; *Citrus limon*).

Sabinene

Sabinene, whose structure is

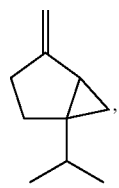

is found in black pepper, carrot seed, sage, and tea trees. Sabinene is made from GPP by sabinene synthase. An illustrative example of a suitable nucleotide sequence includes but is not limited to AF051901, REGION: 26 ... 1798 from *Salvia officinalis*.

γ-Terpinene

γ-Terpinene, whose structure is

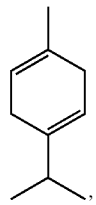

is a constituent of the essential oil from citrus fruits. Biochemically, γ-terpinene is made from GPP by a γ-terpinene synthase. Illustrative examples of suitable nucleotide sequences include: (AF514286, REGION: 30 ... 1832 from *Citrus limon*) and (AB110640, REGION 1 ... 1803 from *Citrus unshiu*).

Terpinolene

Terpinolene, whose structure is

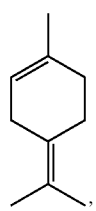

is found in black currant, cypress, guava, lychee, *papaya*, pine, and tea. Terpinolene is made from GPP by terpinolene synthase. Illustrative examples of a suitable nucleotide sequence include but is not limited to: (AY693650 from

*Oscimum basilicum*) and (AY906866, REGION: 10 . . . 1887 from *Pseudotsuga menziesii*).

$C_{15}$ Compounds

Exemplary $C_{15}$ bio-organic compounds are sesquiterpenes which are generally derive from farnesyl pyrophosphate (FPP) which in turn is made by the condensation of two molecules of IPP with one molecule of DMAPP. An enzyme known to catalyze this step is, for example, farnesyl pyrophosphate synthase.

FIG. 5 also shows schematically how IPP and DMAPP can be combined to produce FPP, which can be further processed to a sesquiterpene.

Illustrative examples of nucleotide sequences for farnesyl pyrophosphate synthase include but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUM-FAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), and (MZEFPS; *Zea mays*).

Alternatively, FPP can also be made by adding IPP to GPP. Illustrative examples of nucleotide sequences encoding for an enzyme capable of this reaction include but are not limited to: (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar *Copenhageni* str. *Fiocruz* L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temecula 1).

FPP is then subsequently converted to a variety of $C_{15}$ compounds. Illustrative examples of $C_{15}$ compounds include but are not limited to:

Amorphadiene

Amorphadiene, whose structure is

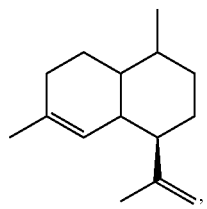

is a precursor to artemisinin which is made by *Artemisia anna*. Amorphadiene is made from FPP by amorphadiene synthase. An illustrative example of a suitable nucleotide sequence is SEQ ID NO. 37 of U.S. Patent Publication No. 2004/0005678.

FIG. 5 shows schematically how IPP and DMAPP can be combined to produce FPP, which can then be further processed to produce amophadiene.

α-Farnesene

α-Farnesene, whose structure is

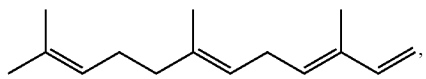

is found in various biological sources including but not limited to the Dufour's gland in ants and in the coating of apple and pear peels. α-Farnesene is made from FPP by α-farnesene synthase. Illustrative examples of suitable nucleotide sequences include but are not limited to DQ309034 from *Pyrus communis* cultivar d'Anjou (pear; gene name AFS1) and AY182241 from *Malus domestica* (apple; gene AFS1). Pechouus et al., *Planta* 219(1):84-94 (2004).

β-Farnesene

β-Farnesene, whose structure is

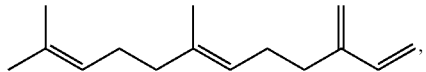

is found in various biological sources including but not limited to aphids and essential oils such as from peppermint. In some plants such as wild potato, β-farnesene is synthesized as a natural insect repellent. β-Farnesene is made from FPP by β-farnesene synthase. Illustrative examples of suitable nucleotide sequences include but is not limited to GenBank accession number AF024615 from *Mentha×piperita* (peppermint; gene Tspa11), and AY835398 from *Artemisia annua*. Picaud et al., *Phytochemistry* 66(9): 961-967 (2005).

Farnesol

Farnesol, whose structure is

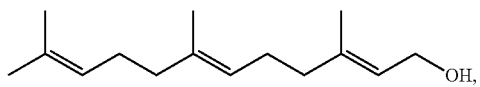 [SMILES: CC(C)=CCC/C(C)=C/CC/C(C)=C/CO]

is found in various biological sources including insects and essential oils such as from cintronella, neroli, cyclamen, lemon grass, tuberose, and rose. Farnesol is made from FPP by a hydroxylase such as farnesol synthase. Illustrative examples of suitable nucleotide sequences include but are not limited to GenBank accession number AF529266 from *Zea mays* and YDR481C from *Saccharomyces cerevisiae* (gene Pho8). Song, L., *Applied Biochemistry and Biotechnology* 128:149-158 (2006).

Nerolidol

Nerolidol, whose structure is

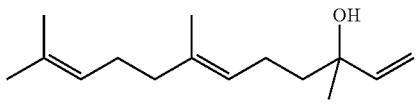 [SMILES: C=CC(C)(O)CC/C=C(\C)CCC=C(C)C]

is also known as peruviol, and is found in various biological sources including as essential oils such as from neroli, ginger, jasmine, lavender, tea tree, and lemon grass. Nerolidol is made from FPP by a hydroxylase such as nerolidol synthase. An illustrative example of a suitable nucleotide sequence includes but is not limited to AF529266 from *Zea mays* (maize; gene tps1).

Patchoulol

Patchoulol, whose structure is

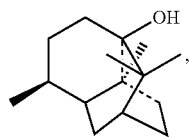

is also known as patchouli alcohol and is a constituent of the essential oil of *Pogostemon patchouli*. Patchouliol is made from FPP by patchouliol synthase. An illustrative example of a suitable nucleotide sequence includes but is not limited to AY508730 REGION: 1 . . . 1659 from *Pogostemon cablin*.

Valenecene

Valencene, whose structure is

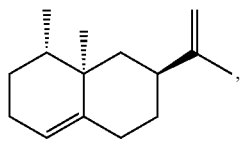

is one of the main chemical components of the smell and flavour of oranges and is found in orange peels. Valencene is made from FPP by nootkatone synthase. Illustrative examples of a suitable nucleotide sequence includes but is not limited to AF441124 REGION: 1 . . . 1647 from *Citrus sinensis* and AY917195 REGION: 1 . . . 1653 from *Perilla frutescens*.

$C_{20}$ Compounds

Exemplary $C_{20}$ bio-organic compounds are diterpenes which are generally derived from geranylgeraniol pyrophosphate (GGPP) which in turn is made by the condensation of three molecules of IPP with one molecule of DMAPP. An enzyme known to catalyze this step is, for example, geranylgeranyl pyrophosphate synthase.

FIG. 5 also shows schematically how IPP and DMAPP can be combined to produce GGPP, which can be further processed to a diterpene, or can be further processed to produce a carotenoid.

Illustrative examples of nucleotide sequences for geranylgeranyl pyrophosphate synthase include but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar *israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGG-PPSGN; *Gibberella fujikuroi*), (AY371321; *Ginkgo biloba*), (AB055496; *Hevea brasiliensis*), (AB017971; *Homo sapiens*), (MCl276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus aciditrophicus* SB), and (NC_006840, Locus YP_204095; *Vibrio fischeri* ES 114).

Alternatively, GGPP can also be made by adding IPP to FPP. Illustrative examples of nucleotide sequences encoding an enzyme capable of this reaction include but are not limited to: (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

GGPP is then subsequently converted to a variety of $C_{20}$ isoprenoids. Illustrative examples of $C_{20}$ compounds include but are not limited to:

Geranylgeraniol

Geranylgeraniol, whose structure is

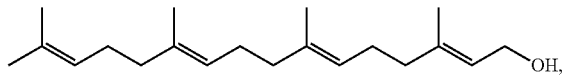 [SMILES: CC(C)=CCC/C(C)=C/CC/C(C)=C/CC/C(C)=C/CO]

is a constituent of wood oil from *Cedrela toona* and of linseed oil. Geranylgeraniol can be made by e.g., adding to the expression constructs a phosphatase gene after the gene for a GGPP synthase.

Abietadiene

Abietadiene encompasses the following isomers:

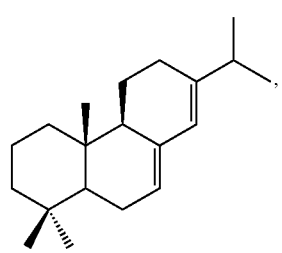

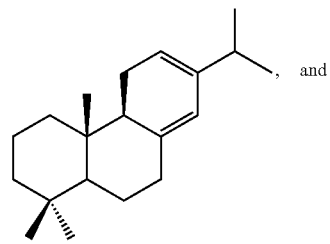

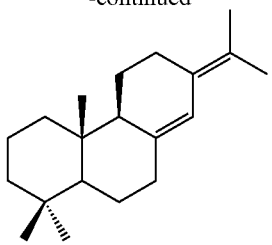

and is found in trees such as *Abies grandis*. Abietadiene is made by abietadiene synthase. An illustrative example of a suitable nucleotide sequence includes but are not limited to: (U50768; *Abies grandis*) and (AY473621; *Picea abies*).

$C_{20+}$ Compounds $C_{20+}$ bio-organic compounds are also within the scope of the present invention. Illustrative examples of such compounds include sesterterpenes ($C_{25}$ compound made from five isoprene units), triterpenes ($C_{30}$ compounds made from six isoprene units), and tetraterpenes ($C_{40}$ compound made from eight isoprene units). These compounds are made by using similar methods described herein and substituting or adding nucleotide sequences for the appropriate synthase(s).

Engineering Pathways

Although for illustrative purposes, the invention has been described with reference to engineering the MEV and/or DXP pathways, these methods can be adapted to similarly engineer suitable pathways to make non-isoprenoid bio-organic compounds. These pathways are typically engineered using recombinant DNA technology by expression of suitable heterologous sequences encoding one or more enzymes.

The subject nucleotide acids can be expressed by a single or multiple vectors. The nucleic acids can be arranged in a single operon, or in separate operons that are placed in one or multiple vectors. Where desired, two expression vectors can be employed, each of which contains one or more heterologous sequences operably linked in a single operon. While the choice of single or multiple vectors and the use of single or multiple operons may depend on the size of the heterologous sequences and the capacity of the vectors, it will largely dependent on the overall yield of a given bio-organic compound that the vector is able to provide when expressed in a selected host cell. In some instances, two-operon expression system provides a higher yield of the bio-organic compound. The subject vectors can stay replicable episomally, or as an integral part of the host cell genome. Typically, the latter is preferred for a sustained propagation of the host cell.

In certain host cells, the subject nucleic acids may be controlled by one or more operons. In some instances, a two or three operon system provides a higher yield of a bio-organic compound over a single operon system.

Where desired, the subject nucleic acid sequences can be modified to reflect the codon preference of a selected host cell to effect a higher expression of such sequences in a host cell. For example, the subject nucleotide sequences will in some embodiments be modified for yeast codon preference. See, e.g., Bennetzen and Hall (1982) J: Biol. Chem. 257(6): 3026-3031. As another non-limiting example, the nucleotide sequences will in other embodiments be modified for *E. coli* codon preference. See, e.g., Gouy and Gautier (1982) Nucleic Acids Res. 10(22):7055-7074; Eyre-Walker (1996) Mol. Biol. Evol. 13(6):864-872. See also Nakamura et al. (2000) Nucleic Acids Res. 28(1):292. Codon usage tables for many organisms are available, which can be used as a reference in designing sequences of the present invention. The use of prevalent codons of a given host microorganism generally increases the likelihood of translation, and hence the expression level of the desired sequences.

Preparation of the subject nucleic acids can be carried out by a variety of routine recombinant techniques and synthetic procedures. Briefly, the subject nucleic acids can be prepared genomic DNA fragments, cDNAs, and RNAs, all of which can be extracted directly from a cell or recombinantly produced by various amplification processes including but not limited to PCR and rt-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (for example, Matteuci et al. (1980) Tet. Lett. 521:719; U.S. Pat. No. 4,500,707 to Caruthers et al.; and U.S. Pat. Nos. 5,436,327 and 5,700,637 to Southern et al.).

The level of transcription of a nucleic acid in a host microorganism can be increased in a number of ways. For example, this can be achieved by increasing the copy number of the nucleotide sequence encoding the enzyme (e.g., by using a higher copy number expression vector comprising a nucleotide sequence encoding the enzyme, or by introducing additional copies of a nucleotide sequence encoding the enzyme into the genome of the host microorganism, for example, by recA-mediated recombination, use of "suicide" vectors, recombination using lambda phage recombinase, and/or insertion via a transposon or transposable element). In addition, it can be carried out by changing the order of the coding regions on the polycistronic mRNA of an operon or breaking up an operon into individual genes, each with its own control elements, or increasing the strength of the promoter (transcription initiation or transcription control sequence) to which the enzyme coding region is operably linked (for example, using a consensus arabinose- or lactose-inducible promoter in an *Escherichia coli* host microorganism in place of a modified lactose-inducible promoter, such as the one found in pBluescript and the pBBR1MCS plasmids), or using an inducible promoter and inducing the inducible-promoter by adding a chemical to a growth medium. The level of translation of a nucleotide sequence in a host microorganism can be increased in a number of ways, including, but not limited to, increasing the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence. Determination of preferred codons and rare codon tRNAs can be based on a sequence analysis of genes derived from the host microorganism.

The subject vector can be constructed to yield a desired level of copy numbers of the encoded enzyme. In some embodiments, the subject vectors yield at least 10, between 10 to 20, between 20-50, between 50-100, or even higher than 100 copies of the desired enzyme. Low copy number plasmids generally provide fewer than about 20 plasmid copies per cell; medium copy number plasmids generally provide from about 20 plasmid copies per cell to about 50 plasmid copies per cell, or from about 20 plasmid copies per cell to about 80 plasmid copies per cell; and high copy number plasmids generally provide from about 80 plasmid copies per cell to about 200 plasmid copies per cell, or more.

Suitable low copy expression vectors for *Escherichia coli* include, but are not limited to, pACYC184, pBeloBac11, pBR332, pBAD33, pBBRIMCS and its derivatives, pSC101, SuperCos (cosmid), and pWE15 (cosmid). Suitable medium copy expression vectors for *Escherichia coli* include, but are not limited to pTrc99A, pBAD24, and vectors containing a ColE1 origin of replication and its derivatives. Suitable high copy number expression vectors for *Escherichia coli* include, but are not limited to, pUC, pBluescript, pGEM, and pTZ vectors. Suitable low-copy (centromeric) expression vectors for yeast include, but are not limited to, pRS415 and pRS416 (Sikorski & Hieter (1989) Genetics 122:19-27). Suitable high-copy 2 micron expression vectors in yeast include, but are not limited to, pRS425 and pRS426 (Christainson et al. (1992) Gene 110: 119-122). Alternative 2 micron expression vectors include non-selectable variants of the 2 micron vector (Bruschi & Ludwig (1988) Curr. Genet. 15:83-90) or intact 2 micron plasmids bearing an expression cassette (as exemplified in U.S. Pat. Appl. 20050084972) or 2 micron plasmids bearing a defective selection marker such as LEU2d (Erhanrt et al. (1983) J. Bacteriol. 156 (2): 625-635) or URA3d (Okkels (1996) Annals of the New York Academy of Sciences 782(1): 202-207).

Regulatory elements include, for example, promoters and operators can also be engineered to increase the metabolic flux of the engineered pathways by increasing the expression of one or more genes that play a significant role in determining the overall yield of the bio-organic compound produced. A promoter is a sequence of nucleotides that initiates and controls the transcription of a nucleic acid sequence by an RNA polymerase enzyme. An operator is a sequence of nucleotides adjacent to the promoter that functions to control transcription of the desired nucleic acid sequence. The operator contains a protein-binding domain where a specific repressor protein can bind. In the absence of a suitable repressor protein, transcription initiates through the promoter. In the presence of a suitable repressor protein, the repressor protein binds to the operator and thereby inhibits transcription from the promoter.

In some embodiments of the present invention, promoters used in expression vectors are inducible. In other embodiments, the promoters used in expression vectors are constitutive. In some embodiments, one or more nucleic acid sequences are operably linked to an inducible promoter, and one or more other nucleic acid sequences are operably linked to a constitutive promoter.

Non-limiting examples of suitable promoters for use in prokaryotic host cells include a bacteriophage T7 RNA polymerase promoter; a trp promoter; a lac operon promoter; a hybrid promoter, for example, a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, for example, U.S. Patent Publication No. 20040131637), a pagC promoter (Pulkkinen and Miller, J. Bacteriol. (1991) 173(1):86-93; Alpuche-Aranda et al. (1992) Proc. Natl. Acad. Sci. USA. 89(21):10079-83), a nirB promoter (Harborne et al. (1992) Mol. Micro. 6:2805-2813), and the like (see, for example, Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, for example, a consensus sigma70 promoter (see, for example, GenBank Accession Nos. AX798980, AX798961, and AX798183); a stationary phase promoter, for example, a dps promoter, an spy promoter, and the like; a promoter derived from the pathogenicity island SPI-2 (see, for example, WO96/17951); an actA promoter (see, for example, Shetron-Rama et al. (2002) Infect. Immun. 70:1087-1096); an rpsM promoter (see, for example, Valdivia and Falkow (1996) Mol. Microbiol. 22:367 378); a tet promoter (see, for example, Hillen et al. (1989) In Saenger W. and Heinemann U. (eds) Topics in Molecular and Structural Biology, Protein-Nucleic Acid Interaction. Macmillan, London, UK, Vol. 10, pp. 143-162); an SP6 promoter (see, for example, Melton et al. (1984) Nucl. Acids Res. 12:7035-7056); and the like.

In some embodiments, the total activity of a heterologous enzyme that plays a larger role in the overall yield of a bio-organic compound relative to other enzymes in the respective pathways is increased by expressing the enzyme from a strong promoter. Suitable strong promoters for *Escherichia coli* include, but are not limited to Trc, Tac, T5, T7, and $P_{Lambda}$. In another embodiment of the present invention, the total activity of one or more engineered pathway enzymes in a host is increased by expressing the enzyme from a strong promoter on a high copy number plasmid. Suitable examples, for *Escherichia coli* include, but are not limited to using Trc, Tac, T5, T7, and $P_{Lambda}$ promoters with pBAD24, pBAD18, pGEM, pBluescript, pUC, and pTZ vectors.

Non-limiting examples of suitable promoters for use in eukaryotic host cells include, but are not limited to, a CMV immediate early promoter, an HSV thymidine kinase promoter, an early or late SV40 promoter, LTRs from retroviruses, and a mouse metallothionein-I promoter.

Non-limiting examples of suitable constitutive promoters for use in prokaryotic host cells include a sigma70 promoter (for example, a consensus sigma70 promoter). Non-limiting examples of suitable inducible promoters for use in bacterial host cells include the pL of bacteriophage λ; Plac; Ptrp; Ptac (Ptrp-lac hybrid promoter); an isopropyl-beta-D44 thiogalactopyranoside (IPTG)-inducible promoter, for example, a lacZ promoter; a tetracycline inducible promoter; an arabinose inducible promoter, for example, PBAD (see, for example, Guzman et al. (1995) J. Bacteriol. 177:4121-4130); a xylose-inducible promoter, for example, Pxyl (see, for example, Kim et al. (1996) Gene 181:71-76); a GAL1 promoter; a tryptophan promoter; a lac promoter; an alcohol-inducible promoter, for example, a methanol-inducible promoter, an ethanol-inducible promoter; a raffinose-inducible promoter; a heat-inducible promoter, for example, heat inducible lambda PL promoter; a promoter controlled by a heat-sensitive repressor (for example, CI857-repressed lambda-based expression vectors; see, for example, Hoffmann et al. (1999) *FEMS* Microbiol Lett. 177(2):327-34); and the like.

Non-limiting examples of suitable constitutive promoters for use in yeast host cells include an ADH1, an ADH2, a PGK, or a LEU2 promoter. Non-limiting examples of suitable inducible promoters for use in yeast host cells include, but are not limited to, a divergent galactose-inducible promoter such as a GAL1 or a GAL10 promoter (West at al.

(1984) Mol. Cell. Biol. 4(11):2467-2478), or a CUP1 promoter. Where desired, the subject vector comprises a promoter that is stronger than a native *E. Coli* Lac promoter.

Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25.).

The genes in the expression vector typically will also encode a ribosome binding site to direct translation (that is, synthesis) of any encoded mRNA gene product. For suitable ribosome binding sites for use in *Escherichia coli*, see Shine et al. (1975) Nature 254:34, and Steitz, in Biological Regulation and Development: Gene Expression (ed. R. F. Goldberger), vol. 1, p. 349, 1979, Plenum Publishing, N.Y. Insertion of the ribosome binding site encoding nucleotide sequence 5'-AAAACA-3' upstream of a coding sequence facilitates efficient translation in a yeast host microorganism (Looman et al. (1993) Nuc. Ac. Res. 21:4268-4271; Yun et. al. (1996) Mol. Microbiol. 19:1225-1239).

Other regulatory elements that may be used in an expression vector include transcription enhancer elements and transcription terminators. See, for example, Bitter et al. (1987) Methods in Enzymology, 153:516-544.

An expression vector may be suitable for use in particular types of host microorganisms and not others. One of ordinary skill in the art, however, can readily determine through routine experimentation whether a particular expression vector is suited for a given host microorganism. For example, the expression vector can be introduced into the host organism, which is then monitored for viability and expression of any genes contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance. Non-limiting examples of suitable selectable markers for prokaryotic cells include tetracycline, ampicillin, chloramphenicol, carbenicillin, and kanamycin resistance.

For production of a bio-organic product at an industrial scale, it may be impractical or too costly to use a selectable marker that requires the addition of an antibiotic to the fermentation media. Accordingly, some embodiments of the present invention employ host cells that do not require the use of an antibiotic resistance conferring selectable marker to ensure plasmid (expression vector) maintenance. In these embodiments of the present invention, the expression vector contains a plasmid maintenance system such as the 60-kb IncP (RK2) plasmid, optionally together with the RK2 plasmid replication and/or segregation system, to effect plasmid retention in the absence of antibiotic selection (see, for example, Sia et al. (1995) J. Bacteriol. 177:2789-97; Pansegrau et al. (1994) J. Mol. Biol. 239:623-63). A suitable plasmid maintenance system for this purpose is encoded by the parDE operon of RK2, which codes for a stable toxin and an unstable antitoxin. The antitoxin can inhibit the lethal action of the toxin by direct protein-protein interaction. Cells that lose the expression vector that harbors the parDE operon are quickly deprived of the unstable antitoxin, resulting in the stable toxin then causing cell death. The RK2 plasmid replication system is encoded by the trfA gene, which codes for a DNA replication protein. The RK2 plasmid segregation system is encoded by the parCBA operon, which codes for proteins that function to resolve plasmid multimers that may arise from DNA replication.

The subject vectors can be introduced into a host cell stably or transiently by variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other transformation methods include microinjection, DEAE dextran mediated transformation, and heat shock in the presence of lithium acetate. Lipid complexes, liposomes, and dendrimers may also be employed to transfect the host microorganism.

Upon transformation, a variety of methods can be practiced to identify the host cells into which the subject vectors have been introduced. One exemplary selection method involves subculturing individual cells to form individual colonies, followed by testing for expression of the desired gene product. Another method entails selecting transformed host cells based upon phenotypic traits conferred through the expression of selectable marker genes contained within the expression vector. Those of ordinary skill can identify genetically modified host cells using these or other methods available in the art.

The introduction of various pathway sequences of the invention into a host cell can be confirmed by methods such as PCR, Southern blot or Northern blot hybridization. For example, nucleic acids can be prepared from the resultant host cells, and the specific sequences of interest can be amplified by PCR using primers specific for the sequences of interest. The amplified product is subjected to agarose gel electrophoresis, polyacrylamide gel electrophoresis or capillary electrophoresis, followed by staining with ethidium bromide, SYBR Green solution or the like, or detection of DNA with a UV detection. Alternatively, nucleic acid probes specific for the sequences of interest can be employed in a hybridization reaction. The expression of a specific gene sequence can be ascertained by detecting the corresponding mRNA via reveres-transcription coupled PCR, Northern blot hybridization, or by immunoassays using antibodies reactive with the encoded gene product. Exemplary immunoassays include but are not limited to ELISA, radioimmunoassays, and sandwich immunoassays.

The yield of a bio-organic compound via one or more metabolic pathways disclosed herein can be augmented by inhibiting reactions that divert intermediates from productive steps towards formation of the bio-organic product. Inhibition of the unproductive reactions can be achieved by reducing the expression and/or activity of enzymes involved in one or more unproductive reactions. Such reactions include side reactions of the TCA cycle that lead to fatty acid biosynthesis, alanine biosynthesis, the aspartate superpathway, gluconeogenesis, heme biosynthesis, and/or glutamate biosynthesis, at a level that affects the overall yield of the bio-organic compound.

A variety of methods are available for knocking out or knocking down a gene of interest. For example, a reduced gene expression may be accomplished by deletion, mutation, and/or gene rearrangement. It can also be carried out with the use of antisense RNA, siRNA, miRNA, ribozymes, triple stranded DNA, and transcription and/or translation inhibitors. In addition, transposons can be employed to disrupt gene expression, for example, by inserting it between the promoter and the coding region, or between two adjacent genes to inactivate one or both genes.

The amount of microorganism per liter of fermentation, or the density of microorganism, can be measured by measuring the weight of microorganism isolated from a given volume of the fermentation medium. A common measure is the dry weight of cells per liter of fermentation medium. Another method which can be used to monitor the fermentation while it is progressing is by a measurement of the optical density of the medium. A common method is to measure the optical density at a wavelength of 600 nm, referred to the $OD_{600}$, or the OD. The OD can be correlated to a the density of a specific type of organism within a specific medium, but the specific relationship between OD and amount of microorganism per volume will not generally be applicable across all types of organisms in all types of media. A calibration curve can be created by measuring the OD and the dry cell weight over a range of cell densities. In some cases, these correlations can be used in different fermentation of the same or similar microorganisms in the same or similar media.

EXAMPLES

The practice of the present invention can employ, unless otherwise indicated, conventional techniques of the biosynthetic industry and the like, which are within the skill of the art. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the arts to which this invention pertains can deduce the correct amount in view of the remaining disclosure herein. Unless indicated otherwise, temperature is reported in degrees Celsius, and pressure is at or near atmospheric pressure at sea level. All reagents, unless otherwise indicated, were obtained commercially. The following examples are intended for illustrative purposes only and do not limit in any way the scope of the present invention.

Example 1

This example describes methods for making expression plasmids that encode enzymes of the MEV pathway from *Saccharomyces cerevisiae* organized in operons.

Expression plasmid pMevT was generated by inserting the MevT operon (SEQ ID NO: 1) into the pBAD33 vector. The MevT operon encodes the set of MEV pathway enzymes that together transform the ubiquitous precursor acetyl-CoA to (R)-mevalonate, namely acetoacetyl-CoA thiolase, HMG-CoA synthase, and HMG-CoA reductase. The MevT operon was generated by PCR amplifying from *Escherichia coli* genomic DNA the coding sequence of the atoB gene (GenBank accession number NC_000913 REGION: 2324131 . . . 2325315) (encodes an acetoacetyl-CoA thiolase), from *Saccharomyces cerevisiae* genomic DNA the coding sequence of the ERG13 gene (GenBank accession number X96617, REGION: 220 . . . 1695) (encodes a HMG-CoA synthase), and from *Saccharomyces cerevisiae* genomic DNA a segment of the coding region of the HMG1 gene (GenBank accession number M22002, REGION: 1660 . . . 3165) (encodes a truncated HMG-CoA reductase (tHMGR)). The upstream PCR primer used for the amplification of the HMG1 gene fragment included an artificial start codon. The amplified fragments were spliced together using overlap extensions (SOEing), during which process ribosome binding sites were introduced after the atoB and the ERG13 coding sequences. After the addition of 3' A overhangs, the MevT operon was ligated into the TA cloning vector pCR4 (Invitrogen, Carlsbad, Calif.), and sequenced to ensure accuracy. The MevT operon was subsequently ligated into the XmaI PstI restriction enzyme site of vector pBAD33 (Guzman et al. (1995) J. Bacteriol. 177(14): 4121-4130). To place the operon under the control of the $P_{Lac}$ promoter, the araC-$P_{BAD}$NsiI-XmaI fragment of pBAD33 was replaced with the NsiI-XmaI fragment of pBBR1MCS, yielding expression plasmid pMevT (see U.S. Pat. No. 7,192,751).

Expression plasmid pAM36-MevT66 was generated by inserting the MevT66 operon into the pAM36 vector. Vector pAM36 was generated by inserting an oligonucleotide cassette containing AscI-SfiI-AsiSI-XhoI-PacI-FsII-PmeI restriction enzyme sites into the pACYC184 vector (GenBank accession number XO6403), and by removing the tet resistance gene in pACYC184. The MevT66 operon was synthetically generated using the nucleotide sequence SEQ ID NO: 1 as a template, which comprises the atoB gene from *Escherichia coli* (GenBank accession number NC_000913 REGION: 2324131 . . . 2325315), the ERG13 gene from *Saccharomyces cerevisiae* (GenBank accession number X96617, REGION: 220 . . . 1695), and a truncated version of the HMG1 gene from *Saccharomyces cerevisiae* (GenBank accession number M22002, REGION: 1777 . . . 3285), all three sequences being codon-optimized for expression in *Escherichia coli*. The synthetically generated MevT66 operon was flanked by a 5' EcoRI restriction enzyme site and a 3' Hind III restriction enzyme site, and could thus be cloned into compatible restriction enzyme sites of a cloning vector such as a standard pUC or pACYC origin vector. From this construct, the MevT66 operon was PCR amplified with flanking SfiI and AsiSI restriction enzyme sites, the amplified DNA fragment was digested to completion using SfiI and AsiSI restriction enzymes, the reaction mixture was resolved by gel electrophoresis, the approximately 4.2 kb DNA fragment was gel extracted using a Qiagen gel purification kit (Valencia, Calif.), and the isolated DNA fragment was ligated into the SfiI AsiSI restriction enzyme site of the pAM36 vector, yielding expression plasmid pAM36-MevT66.

Expression plasmid pAM25 was generated by inserting the MevT66 operon into the pAM29 vector. Vector pAM29 was created by assembling the p15A origin of replication and kan resistance gene from pZS24-MCS1 (Lutz and Bujard (1997) *Nucl Acids Res.* 25:1203-1210) with an oligonucleotide-generated lacUV5 promoter. The DNA synthesis construct comprising the MevT66 operon (see above) was digested to completion using EcoRI and Hind III restriction enzymes, the reaction mixture was resolved by gel electrophoresis, the 4.2 kb DNA fragment was gel extracted, and the isolated DNA fragment was ligated into the EcoRI HindIII restriction enzyme site of pAM29, yielding expression plasmid pAM25.

Expression plasmid pMevB-Cm was generated by inserting the MevB operon into the pBBR1MCS-1 vector. The MevB operon encodes the set of enzymes that together convert (R)-mevalonate to IPP, namely mevalonate kinase, phosphomevalonate kinase, and mevalonate pyrophosphate carboxylase. The MevB operon was generated by PCR amplifying from *Saccharomyces cerevisiae* genomic DNA the coding sequences of the ERG12 gene (GenBank accession number X55875, REGION: 580 . . . 1911) (encodes a mevalonate kinase), the ERG8 gene (GenBank accession number Z49939, REGION: 3363 . . . 4718) (encodes a phosphomevalonate kinase), and the MVD1 gene (GenBank accession number X97557, REGION: 544 . . . 1734) (encodes a mevalonate pyrophosphate carboxylase), and by splicing the PCR fragments together using overlap extensions (SOEing). By choosing appropriate primer sequences, the stop codons of ERG12 and ERG8 were changed from TAA to TAG during amplification to introduce ribosome binding sites. After the addition of 3' A overhangs, the MevB operon was ligated into the TA cloning vector pCR4 (Invitrogen, Carlsbad, Calif.). The MevB operon was excised by digesting the cloning construct to completion using PstI restriction enzyme, resolving the reaction mixture by gel electrophoresis, gel extracting the 4.2 kb DNA fragment, and ligating the isolated DNA fragment into the PstI restriction enzyme site of vector pBBR1MCS-1 (Kovach et al., *Gene* 166(1): 175-176 (1995)), yielding expression plasmid pMevB-Cm.

Expression plasmid pMBI was generated by inserting the MBI operon into the pBBR1MCS-3 vector. The MBI operon encodes the same enzymes as the MevB operon, as well as an isopentenyl pyrophosphatase isomerase that catalyzes the conversion of IPP to DMAPP. The MBI operon was generated by PCR amplifying from *Escherichia coli* genomic DNA the coding sequence of the idi gene (GenBank accession number AF119715) using primers that contained an XmaI restriction enzyme site at their 5' ends, digesting the amplified DNA fragment to completion using XmaI restriction enzyme, resolving the reaction mixture by gel electrophoresis, gel extracting the 0.5 kb fragment, and ligating the isolated DNA fragment into the XmaI restriction enzyme site of expression plasmid pMevB-Cm, thereby placing idi at the 3' end of the MevB operon. The MBI operon was subcloned into the SalI and SacI restriction enzyme sites of vector pBBR1MCS-3 (Kovach et al., *Gene* 166(1): 175-176 (1995)), yielding expression plasmid pMBI (see U.S. Pat. No. 7,192,751).

Expression plasmid pMBIS was generated by inserting the ispA gene into pMBI. The ispA gene encodes a farnesyl pyrophosphate synthase that catalyzes the conversion of IPP and DMAPP to FPP. The coding sequence of the ispA gene (GenBank accession number D00694, REGION: 484 . . . 1383) was PCR amplified from *Escherichia coli* genomic DNA using a forward primer with a SacII restriction enzyme site and a reverse primer with a SacI restriction enzyme site. The amplified PCR product was digested to completion with SacII and SacI restriction enzymes, the reaction mixture was resolved by gel electrophoresis, and the 0.9 kb DNA fragment was gel extracted. The isolated DNA fragment was ligated into the SacII SacI restriction enzyme site of pMBI, thereby placing the ispA gene 3' of idi and the MevB operon, and yielding expression plasmid pMBIS (see U.S. Pat. No. 7,192,751).

Figure 6:
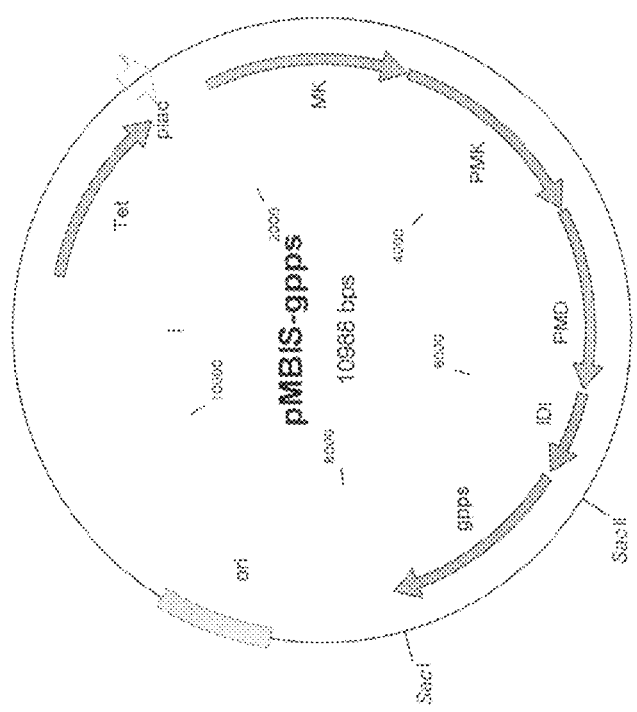
FIG. 6 shows a map of expression plasmid pMBIS-gpps.

Expression plasmid pMBIS-gpps was derived from expression plasmid pMBIS by replacing the ispA coding sequence with a nucleotide sequence encoding a geranyl diphosphate synthase ("gpps"). A DNA fragment comprising a nucleotide sequence encoding the geranyl diphosphate synthase was generated synthetically using the coding sequence of the gpps gene of *Arabidopsis thaliana* (GenBank accession number Y17376, REGION: 52 . . . 1320), codon-optimized for expression in *Escherichia coli*, as a template. The nucleotide sequence was flanked by a leader SacII restriction enzyme site and a terminal SacI restriction enzyme site, and can be cloned into compatible restriction enzyme sites of a cloning vector such as a standard pUC or pACYC origin vector. The synthetically generated geranyl diphosphate synthase sequence was isolated by digesting the DNA synthesis construct to completion using SacII and SacI restriction enzymes, resolving the reaction mixture by gel electrophoresis, gel extracting the approximately 1.3 kb DNA fragment, and ligating the isolated DNA fragment into the SacII SacI restriction enzyme site of expression plasmid pMBIS, yielding expression plasmid pMBIS-gpps (see FIG. 6 for a plasmid map).

Expression plasmid pAM45 was generated by inserting the MBIS operon into pAM36-MevT66 and adding lacUV5 promoters in front of the two operons. The MBIS operon was PCR amplified from pMBIS using primers comprising a 5' XhoI restriction enzyme site and a 3' PacI restriction enzyme site. The amplified PCR product was digested to completion using XhoI and PacI restriction enzymes, the reaction mixture was resolved by gel electrophoresis, the 5.4 kb DNA fragment was gel extracted, and the isolated DNA fragment was ligated into the XhoI PacI restriction enzyme site of pAM36-MevT66, yielding plasmid pAM43. A DNA fragment comprising a nucleotide sequence encoding the lacUV5 promoter was synthesized from oligonucleotides and sub-cloned into the AscI SfiI and AsiSI XhoI restriction enzyme sites of pAM43, yielding expression plasmid pAM45.

Example 2

This example describes methods for making expression vectors encoding enzymes of the MEV pathway from *Staphylococcus aureus* organized in operons.

Expression plasmid pAM41 was derived from expression plasmid pAM25 by replacing the coding sequence of the HMG1 gene, which encodes the *Saccharomyces cerevisiae* HMG-CoA reductase, with the coding sequence of the mvaA gene, which encodes the *Staphylococcus aureus* HMG-CoA reductase (GenBank accession number BA000017, REGION: 2688925 . . . 2687648). The coding sequence of the mvaA gene was PCR amplified from *Staphyloccoccus aureus* subsp. *aureus* (ATCC 70069) genomic DNA using primers 4-49 mvaA SpeI (SEQ ID NO: 2) and 4-49 mvaAR XbaI (SEQ ID NO: 3), the amplified DNA fragment was digested to completion using SpeI restriction enzyme, the reaction mixture was resolved by gel electrophoresis, and the approximately 1.3 kb DNA fragment was gel extracted. The HMG1 coding sequence was removed from pAM25 by digesting the plasmid to completion using HindIII restriction enzyme. The terminal overhangs of the resulting linear DNA fragment were blunted using T4 DNA polymerase. The DNA fragment was then partially digested using SpeI restriction enzyme, the reaction mixture was resolved by gel electrophoresis, and the 4.8 kb DNA fragment was gel extracted. The isolated DNA fragment was ligated with the SpeI-digested mvaA PCR product, yielding expression plasmid pAM41. The nucleotide sequence of the atoB(opt):ERG13(opt):mvaA operon contained in pAM41 is SEQ ID NO: 41. ERG13 is also known as HMGS or HMG-CoA synthase.

Expression plasmid pAM52 was derived from expression plasmid pAM41 by replacing the coding sequence of the ERG13 gene, which encodes the *Saccharomyces cerevisiae* HMG-CoA synthase, with the coding sequence of the mvaS gene, which encodes the *Staphylococcus aureus* HMG-CoA synthase (GenBank accession number BA000017, REGION: 2689180 . . . 2690346). The coding sequence of the mvaS gene was PCR amplified from *Staphyloccoccus aureus* subsp. *aureus* (ATCC 70069) genomic DNA using primers HMGS 5' Sa mvaS-S(SEQ ID NO: 4) and HMGS 3' Sa mvaS-AS (SEQ ID NO: 5), and the amplified DNA fragment was used as a PCR primer to replace the coding sequence of the HMG1 gene in pAM41 according to the method of Geiser et al. (BioTechniques 31:88-92 (2001)), yielding expression plasmid pAM52. The nucleotide sequence of the atoB(opt):mvaS:mvaA operon contained in pAM52 is SEQ ID NO: 42.

Expression plasmid pAM97 was derived from expression plasmid pAM45 by replacing the MevT66 operon with the (atoB(opt):mvaS:mvaA) operon of expression plasmid pAM52. Expression plasmid pAM45 was digested to completion using AsiSI and SfiI restriction enzymes, the reaction mixture was resolved by gel electrophoresis, and the 8.3 kb DNA fragment lacking the MevT66 operon was gel extracted. The (atoB(opt):mvaS:mvaA) operon of pAM52 was PCR amplified using primers 19-25 atoB SfiI-S(SEQ ID NO: 6) and 19-25 mvaA-AsiSI-AS (SEQ ID NO: 7), the PCR product was digested to completion using SfiI and AsiSI restriction enzymes, the reaction mixture was resolved by gel electrophoresis, the 3.7 kb DNA fragment was gel extracted, and the isolated DNA fragment was ligated into the AsiSI SfiI restriction enzyme site of expression plasmid pAM45, yielding expression plasmid pAM97.

Expression plasmid pAM97-MBI was derived from expression plasmid pAM97 and pAM45 by replacing the MBIS operon of pAM97 with the MBI operon of pAM45. The MBI operon was PCR amplified from pAM45 using primers 9-70C (SEQ ID NO: 8) and 26-39B (SEQ ID NO: 9), the reaction mixture was resolved by gel electrophoresis, the 4.5 kb DNA fragment was gel extracted, and the isolated DNA fragment was digested to completion using SacI and XhoI restriction enzymes. Expression plasmid pAM97 was digested to completion using SacI and XhoI restriction enzymes, the reaction mixture was resolved by gel electrophoresis, the 7.6 kb fragment was gel extracted, and the isolated DNA fragment was ligated with the MBI operon PCR product, yielding expression plasmid pAM97-MBI.

Expression plasmid pAM97-MevB was derived from expression plasmid pAM97 and pAM45 by replacing the MBIS operon of pAM97 with the MevB operon of pAM45. The MevB operon was PCR amplified from pAM45 using primers 9-70C (SEQ ID NO: 8) and 26-39A (SEQ ID NO: 10), the reaction mixture was resolved by gel electrophoresis, the 3.9 kb DNA fragment was gel extracted, and the isolated DNA fragment was digested to completion using SacI and XhoI restriction enzymes. Expression plasmid pAM97 was digested to completion using SacI and XhoI restriction enzymes, the reaction mixture was resolved by gel electrophoresis, the 7.6 kb fragment was gel extracted, and the isolated DNA fragment was ligated with the MevB operon PCR product, yielding expression plasmid pAM97-MevB.

Expression plasmid pAM128 was generated by inserting the (atoB(opt):mvaS:mvaA) and MBIS operons of expression plasmid pAM97 into a vector that comprises the RK2 plasmid replication, segregation, and maintenance system, which obviates the continuous need for antibiotic selection of host cell transformants. The RK2 plasmid was digested to completion using PstI restriction enzyme, the reaction mixture was resolved by gel electrophoresis, the approximately 6.3 kb DNA fragment containing the entire par locus was gel extracted, and the isolated DNA fragment was subcloned into the PstI restriction enzyme site of the mini RK2 replicon pRR10 (Roberts et al. (1990) J Bacteriol. 172(11): 6204-6216), yielding vector pAM132. Expression plasmid pAM97 was digested to completion using AscI and SacI restriction enzymes, the reaction mixture was resolved by gel electrophoresis, the approximately 9.4 kb DNA fragment was gel extracted, and the isolated DNA fragment was ligated into the MluI SacI restriction enzyme site of pAM132, yielding expression plasmid pAM128.

Example 3

This example describes methods for making expression vectors that encode enzymes of the MEV pathway from *Enterococcus faecalis* organized in operons.

Plasmid pAM16 was generated by inserting the coding sequence of the mvaE gene of *Enterococcus faecalis* (GenBank accession number AF290092 REGION: 1479 . . . 3890) (encodes an acetyl-CoA acetyltransferase/HMG-CoA reductase (HMGR)) into the pBlueScripII-KS(+) vector. The coding sequence of the mvaE gene was PCR amplified from *Enterococcus faecalis* genomic DNA (ATCC 700802) using 5' phosphorylated primers 4-40 mvaEF BamHI (SEQ ID NO: 11) and 4-40 mvaERHindIII (SEQ ID NO: 12). (Note that primer 4-40 mvaEF BamHI changes the start codon of the mvaE gene from TTG to ATG in the amplified PCR product.) The resulting PCR product was ligated into the SmaI restriction enzyme site of pBlueScripII-KS(+) (Stratagene, La Jolla, Calif.), yielding expression plasmid pAM16.

Plasmid pAM18 was generated by inserting the coding sequence of the mvaS gene of *Enterococcus faecalis* (GenBank accession number AF290092 REGION: 142 . . . 1293) (encodes a HMG-CoA synthase (HMGS)) into the pBlueScripII-KS(+) vector. The coding sequence of the mvaS gene was PCR amplified from *Enterococcus faecalis* genomic DNA (ATCC 700802) using 5' phosphorylated primers 4-40 mvaSF BglII (SEQ ID NO: 13) and 4-39 mvaSR BamHI (SEQ ID NO: 14), and the PCR product was ligated into the SmaI restriction enzyme site of pBlueScripII-KS(+) (Stratagene, La Jolla, Calif.), yielding expression plasmid pAM18.

Expression plasmid pAM22 was generated by inserting the coding sequence of the mvaE gene of expression plasmid pAM16 into the pZE21-$P_{L-lacO1}$ vector. Vector pZE21-$P_{L-lacO1}$ is a derivative of vector pZE21-MCS-1 in which the tet promoter was replaced with the $P_{L-lacO1}$ promoter (Lutz and Bujard (1997) *Nucl Acids Res.* 25:1203-1210). Expression plasmid pAM16 was digested to completion using BamHI and HindIII restriction enzymes, the reaction mixture was resolved by gel electrophoresis, the approximately 2.4 kb DNA fragment containing the mvaE coding sequence was gel extracted, and the isolated DNA fragment was inserted into the BamHI HindIII restriction enzyme site of pZE21-$P_{L-lacO1}$, yielding expression plasmid pAM22.

Expression plasmid pAM33 was generated by inserting the coding sequence of the mvaS gene of expression plasmid pAM18 into expression plasmid pAM22. Expression plasmid pAM18 was digested to completion using BglII and BamHI restriction enzymes, the reaction mixture was resolved by gel electrophoresis, the approximately 1.2 kb DNA fragment containing the coding sequence of the mvaS gene was gel extracted, and the isolated DNA fragment was inserted into the BamHI site of expression plasmid pAM22, yielding expression plasmid pAM33.

Expression plasmid pAM34 was generated by inserting the mvaS-mvaE operon of expression plasmid pAM33 into vector pAM29. The mvaS-mvaE operon was isolated by partially digesting pAM33 using EcoRI restriction enzyme, digesting the resulting linear DNA fragment using MluI restriction enzyme, resolving the reaction mixture by gel electrophoresis, and gel extracting the approximately 3.6 kb DNA fragment. The vector backbone of pAM29 was obtained by digesting to completion expression vector pAM25 using MluI and EcoRI restriction enzymes, resolving the reaction mixture by gel electrophoresis, and gel extracting the approximately 2.1 kb DNA fragment. The two isolated DNA fragments were ligated, yielding expression plasmid pAM34.

Example 4

This example describes methods for making expression plasmids that encode enzymes of the DXP pathway from Escherichia coli organized in operons.

Figure 7:
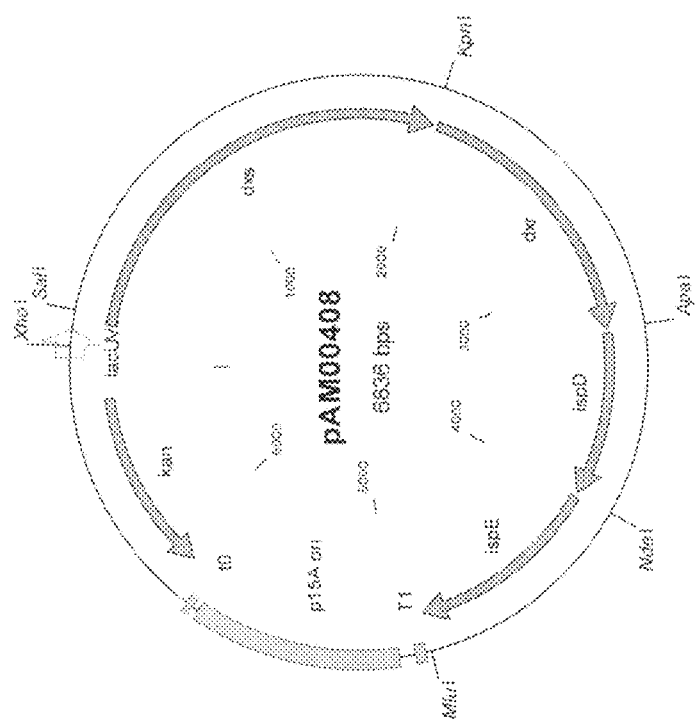
FIG. 7 shows a map of expression plasmid Pam00408

Expression plasmid pAM408 was generated by inserting genes encoding enzymes of the "top" DXP pathway into the pAM29 vector. Enzymes of the "top" DXP pathway include 1-deoxy-D-xylulose-5-phosphate synthase (encoded by the dxs gene of Escherichia coli), 1-deoxy-D-xylulose-5-phosphate reductoisomerase (encoded by the dxr gene of Escherichia coli), 4-diphosphocytidyl-2C-methyl-D-erythritol synthase (encoded by the ispD gene of Escherichia coli), and 4-diphosphocytidyl-2C-methyl-D-erythritol synthase (encoded by the ispE gene of Escherichia coli), which together transform pyruvate and D-glyceraldehyde-3-phosphate to 4-diphosphocytidyl-2C-methyl-D-erythritol-2-phosphate. DNA fragments comprising nucleotide sequences that encode enzymes of the "top" DXP pathway were generated by PCR amplifying the coding sequences of the dxs (GenBank accession number U00096 REGION: 437539 . . . 439401), dxr (GenBank accession number U00096 REGION: 193521 . . . 194717), ispD (GenBank accession number U00096 REGION: 2869803 . . . 2870512), and ispE (GenBank accession number U00096 REGION 1261249 . . . 1262100) genes from Escherichia coli strain DH1 (ATCC #33849) with added optimal Shine Dalgarno sequences and 5' and 3' restriction enzyme sites using the PCR primers shown in SEQ ID NOS: 15-18. The PCR products were resolved by gel electrophoresis, gel extracted using a Qiagen (Valencia, Calif.) gel purification kit, digested to completion using appropriate restriction enzymes (XhoI and KpnI for the PCR product comprising the dxs gene; KpnI and ApaI for the PCR product comprising the dxr gene; ApaI and NdeI for the PCR product comprising the ispD gene; NdeI and MluI for the PCR product comprising the ispE gene), and purified using a Qiagen (Valencia, Calif.) PCR purification kit. Roughly equimolar amounts of each PCR product were then added to a ligation reaction to assemble the individual genes into an operon. From this ligation reaction, 1 µl of reaction mixture was used to PCR amplify 2 separate gene cassettes, namely the dxs-dxr and the ispD-ispE gene cassettes. The dxs-dxr gene cassette was PCR amplified using primers 67-1A-C (SEQ ID NO: 15) and 67-1D-C(SEQ ID NO: 18), and the ispD-ispE gene cassette was PCR amplified using primers 67-1E-C(SEQ ID NO: 19) and 67-1H-C(SEQ ID NO: 22). The two PCR products were resolved by gel electrophoresis, and gel extracted. The PCR product comprising the dxs-dxr gene cassette was digested to completion using XhoI and ApaI restriction enzymes, and the PCR product comprising the ispD-ispE gene cassette was digested to completion using ApaI and MluI restriction enzymes, and the two PCR products were purified. Vector pAM29 was digested to completion using SaiI and MluI restriction enzymes, and the two digested PCR products containing the "top" DXP pathway operon were ligated into the SaiI MluI restriction enzyme site of the pAM29 vector, yielding expression plasmid pAM408 (see FIG. 7 for a plasmid map).

Expression plasmid pAM409 was generated by inserting genes encoding enzymes of the "bottom" DXP pathway into the pAM369 vector. Enzymes of the "bottom" DXP pathway include 2C-methyl-D-erythritol 2,4-cyclodiphosphate synthase (encoded by the ispF gene of Escherichia coli), 1-hydroxy-2-methyl-2-(E)-butenyl-4-diphosphate synthase (encoded by the ispG gene of Escherichia coli), and isopentenyl/dimethylallyl diphosphate synthase (encoded by the ispH gene of Escherichia coli), which together transform 4-diphosphocytidyl-2C-methyl-D-erythritol-2-phosphate to IPP and DMAPP. IPP is also converted to DMAPP through the activity of isopentyl diphosphate isomerase (encoded by the idi gene of Escherichia coli). DMAPP can be further converted to FPP through the activity of farnesyl diphosphate synthase (encoded by the ispA gene of Escherichia coli). An operon encoding enzymes of the "bottom" DXP pathway as well as an isopentyl diphosphate isomerase and a farnesyl diphosphate synthase was generated by PCR amplifying the ispF (GenBank accession number U00096 REGION: 2869323 . . . 2869802), ispG (GenBank accession number U00096 REGION: 2638708 . . . 2639826), ispH (GenBank accession number U00096 REGION: 26277 . . . 27227), idi (GenBank accession number AF119715), and ispA (GenBank accession number D00694 REGION: 484 . . . 1383) genes from Escherichia coli strain DH1 (ATCC #33849) with added optimal Shine Dalgarno sequences and 5' and 3' restriction enzyme sites using the appropriate PCR primers. The PCR products were resolved by gel electrophoresis, gel extracted, digested with the appropriate restriction enzymes (BamHI and ApaI for the PCR product comprising the ispF gene; KpnI and ApaI for the PCR product comprising the ispG gene; SaiI and KpnI for the PCR product comprising the ispH gene; SaiI and HindIII for the PCR product comprising the idi gene; HindIII and NcoI for the PCR product comprising the ispA gene), and purified. Roughly equimolar amounts of each PCR product were then added to a ligation reaction to assemble the individual genes into an operon. From this ligation reaction, 1 µl of reaction mixture was used to PCR amplify 2 separate gene cassettes, namely the ispF-ispG and the ispH-idi-ispA gene cassettes. The ispF-ispG gene cassette was PCR amplified using primers 67-2A-C(SEQ ID NO: 23) and 67-2D-C(SEQ ID NO: 26), and the ispH-idi-ispA gene cassette was PCR amplified using primers 67-2E-C(SEQ ID NO: 27) and 67-2J-C(SEQ ID NO: 32). The two PCR products were resolved by gel electrophoresis, and gel extracted. The PCR product comprising the ispF-ispG gene cassette was digested to completion using BamHI and KpnI restriction enzymes, and the PCR product comprising the ispH-idi-ispA gene cassette was digested to completion using KpnI and NcoI restriction enzymes, and the two PCR products were purified. Vector pAM369 was created by assembling the p15A origin of replication from pAM29 and beta-lactamase gene for ampicillin resistance from pZE12-luc (Lutz and Bujard (1997) Nucl Acids Res. 25:1203-1210) with an oligonucleotide-generated lacUV5 promoter. Vector pAM369 was digested to completion using BamHI and NcoI restriction enzymes, and the 2 isolated PCR products containing the "bottom" DXP pathway operon were ligated into the BamHI NcoI restriction enzyme site of the pAM369 vector, yielding expression plasmid pAM409.

Figure 8:
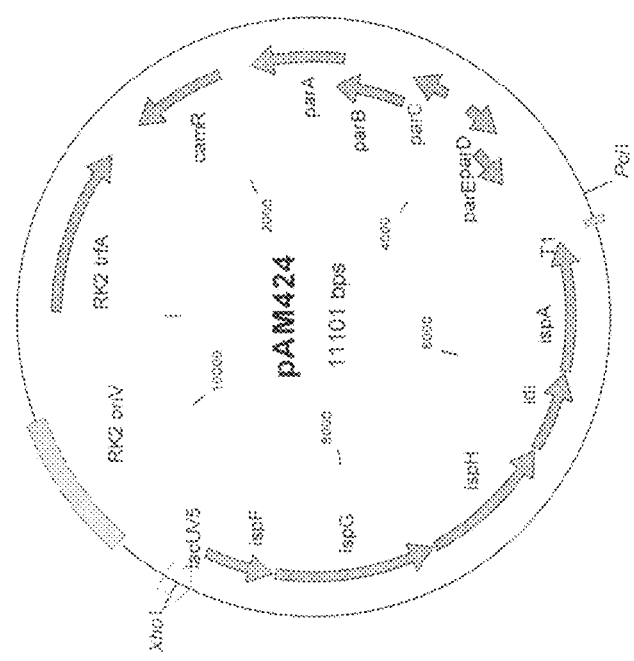
FIG. 8 shows a map of expression plasmid pAM424.

Expression plasmid pAM424, a derivative of expression plasmid pAM409 containing the broad-host range RK2 origin of replication, was generated by transferring the lacUV5 promoter and the ispFGH-idi-ispA operon of pAM409 to the pAM257 vector. Vector pAM257 was generated as follows: the RK2 par locus was PCR-amplified from RK2 plasmid DNA (Meyer et al. (1975) *Science* 190:1226-1228) using primers 9-156A (SEQ ID NO: 33) and 9-156B (SEQ ID NO: 34), the 2.6 kb PCR product was digested to completion using AatII and XhoI restriction enzymes, and the DNA fragment was ligated into a plasmid containing the p15 origin of replication and the chloramphenicol resistance gene from vector pZA31-luc (Lutz and Bujard (1997) *Nucl Acids Res.* 25:1203-1210), yielding plasmid pAM37-par; pAM37-par was digested to completion using restriction enzymes SacI and HindIII, the reaction mixture was resolved by gel electrophoresis, the DNA fragment comprising the RK2 par locus and the chloramphenicol resistance gene was gel extracted, and the isolated DNA fragment was ligated into the SacI HindIII site of the mini-RK2 replicon pRR10 (Roberts et al. (1990) *J Bacteriol.* 172:6204-6216), yielding vector pAM133; pAM133 was digested to completion using BglII and HindIII restriction enzymes, the reaction mixture was resolved by gel electrophoresis, the approximately 6.4 kb DNA fragment lacking the ampicillin resistance gene and oriT conjugative origin was gel extracted, and the isolated DNA fragment was ligated with a synthetically generated DNA fragment comprising a multiple cloning site that contained PciI and XhoI restriction enzyme sites, yielding vector pAM257. Expression plasmid pAM409 was digested to completion using XhoI and PciI restriction enzymes, the reaction mixture was resolved by gel electrophoresis, and the approximately 4.4 kb DNA fragment was gel extracted. Vector pAM257 was digested to completion using restriction enzymes XhoI and PciI, and the isolated DNA fragment containing the lacUV5 promoter and ispFGH-idi-ispA operon was ligated into the XhoI PciI restriction enzyme site of the pAM257 vector, yielding expression plasmid pAM424 (see FIG. 8 for a plasmid map).

Example 5

This example describes methods for making expression plasmids that encode enzymes that convert FPP or GPP.

Figure 9:
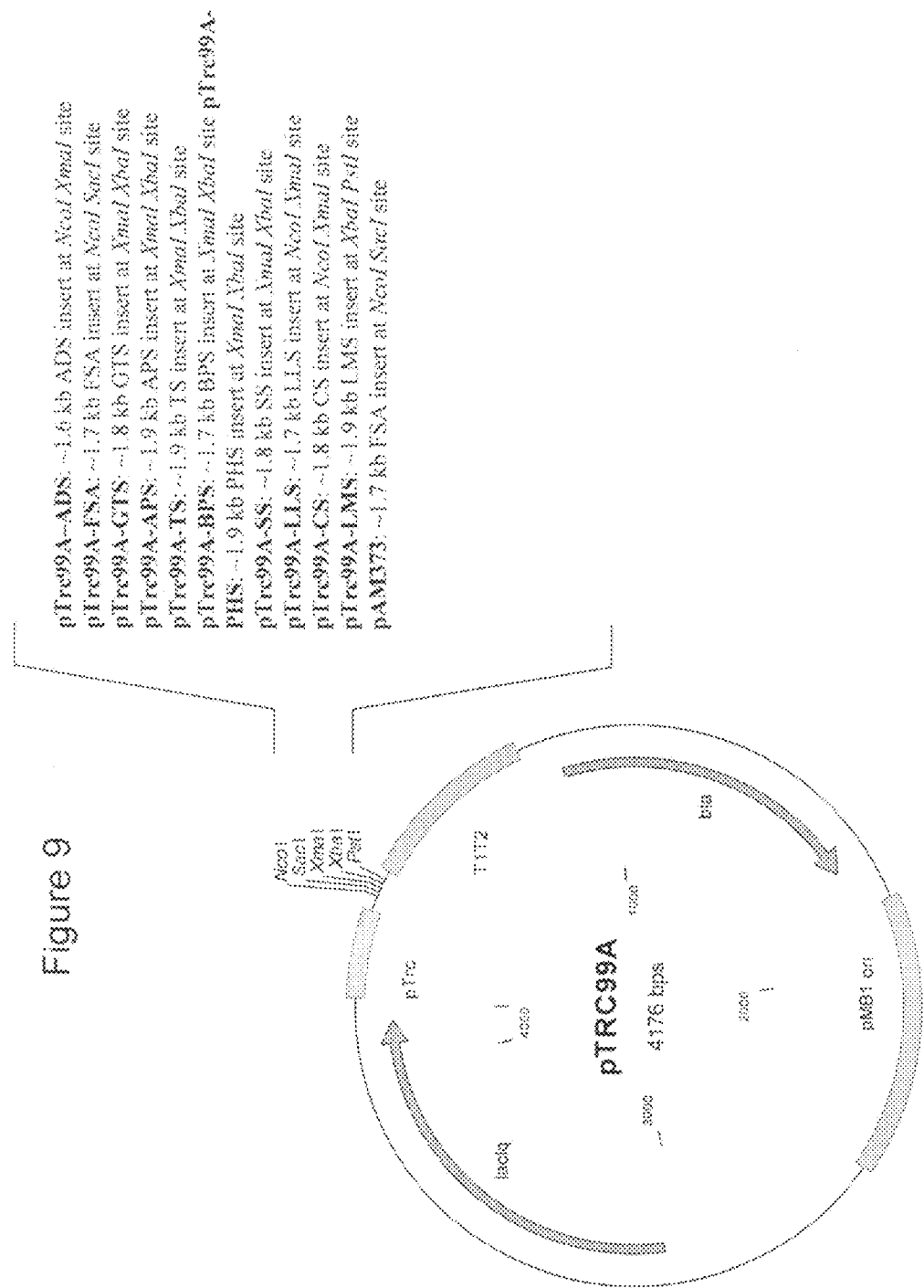
FIG. 9 shows a map of expression plasmids pTrc99A-ADS, pTrc99A-FSA, pTrc99A-LLS, pTrc99A-LMS, pTrc99A-GTS, pTrc99A-APS, pTrc99A-BPS, pTrc99A-PHS, pTrc99A-TS, pTrc99A-CS, pTrc99A-SS, and pAM373.
Figure 10:
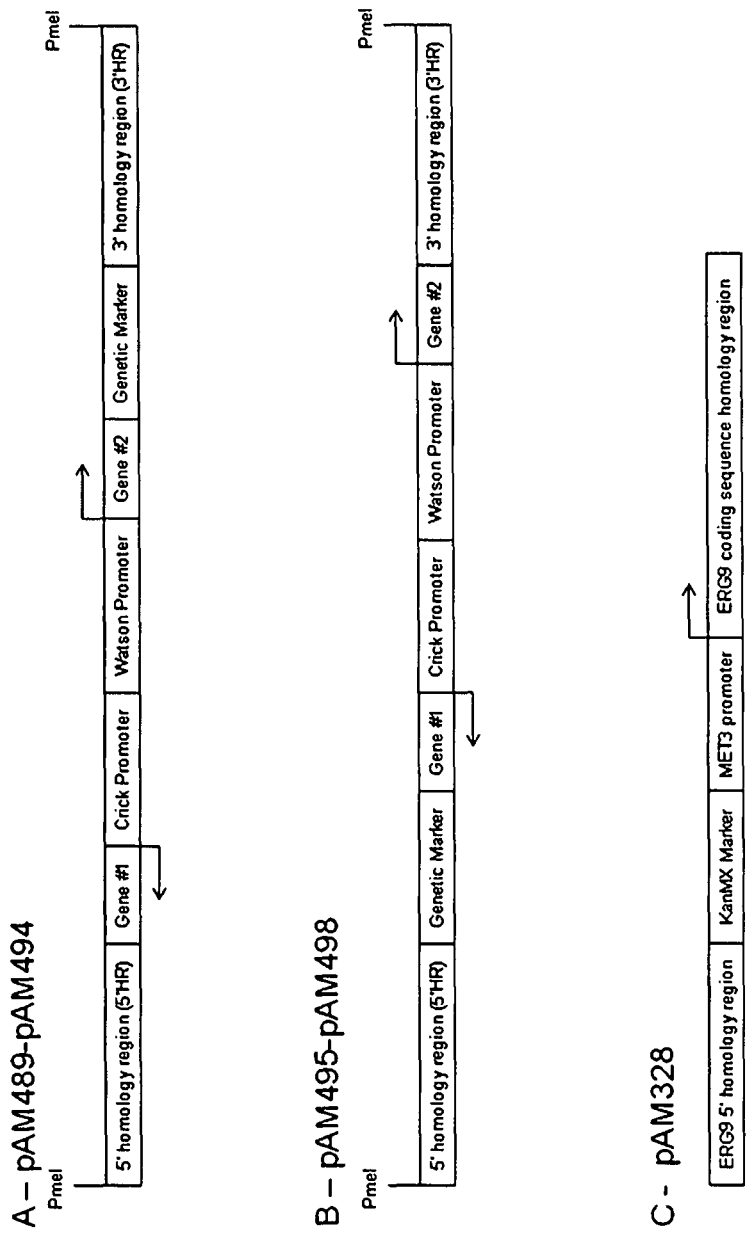
FIG. 10 are schematics for the construction of plasmids pAM489-pAM498.

Expression plasmid pTrc99A-ADS was generated by inserting a nucleotide sequence encoding an amorpha-4,11-diene synthase ("ADS") into vector pTrc99A. The amorpha-4,11-diene synthase sequence was generated synthetically, so that upon translation the amino acid sequence would be identical to that described by Merke et al. (2000) *Ach. Biochem. Biophys.* 381:173-180, so that the nucleotide sequence encoding the amorpha-4,11-diene synthase was optimized for expression in *Escherichia coli*, and so that the nucleotide sequence was flanked by a 5' NcoI and a 3' XmaI restriction enzyme site (see U.S. Pat. No. 7,192,751). The nucleotide sequence was digested to completion using NcoI and XmaI restriction enzymes, the reaction mixture was resolved by gel electrophoresis, the approximately 1.6 kb DNA fragment was gel-extracted, and the isolated DNA fragment was inserted into the NcoI XmaI restriction enzyme site of the pTrc99A vector (Amman et al. (1985) *Gene* 40:183-190), yielding expression plasmid pTrc99A-ADS (see FIG. 9 for a plasmid map).

Expression plasmid pAM113 is a chloramphenicol-resistant derivative of pTrc99A-ADS. It was generated by PCR amplifying the chloramphenicol resistance gene from vector pZA31-luc (Lutz and Bujard (1997) *Nucl Acids Res.* 25:1203-1210) using 5'-phosphorylated primers 19-137 cml-pAM37-AS (SEQ ID NO: 35) and 19-137 cml-pAM37-S (SEQ ID NO: 36), and inserting the 920 bp PCR product into the FspI restriction enzyme site of expression plasmid pTrc99A-ADS, yielding expression plasmid pAM113.

Expression plasmid pC9 was generated by inserting a genomic DNA fragment of *Bacillus subtilis* 6051 comprising the coding sequence of the nudF gene and upstream genomic sequences (GenBank accession number Z99116 REGION: 49364 ... 48548) into vector pTrc99A (Amann et al. (1988) *Gene* 69:301-315). Expression plasmid pNudF-H was generated by inserting the coding sequence of the *Bacillus subtilis* 6051 nudF gene (GenBank accession number Z99116 REGION: 49105 ... 48548) into vector pTrc99A. Expression plasmid pyhfR was generated by inserting the coding sequence of the *Bacillus subtilis* 6051 yhfR gene (GenBank accession number Z99109 REGION: 97583 ... 97002) into vector pTrc99A.

Expression plasmid pAM373 was generated by inserting a nucleotide sequence encoding the β-farnesene synthase ("FSB") of *Artemisia annua* (GenBank accession number AY835398), codon-optimized for expression in *Escherichia coli*, into the pTrc99A vector. The nucleotide sequence encoding the 1-farnesene synthase was generated synthetically, and was amplified by PCR from its DNA synthesis construct using the appropriate primers. To create a leader NcoI restriction enzyme site in the PCR product comprising the β-farnesene synthase coding sequence, the codon encoding the second amino acid in the original polypeptide sequence (TCG coding for serine) was replaced by a codon encoding aspartic acid (GAC) in the 5' PCR primer (SEQ ID NO: 37). The resulting PCR product was partially digested using NcoI restriction enzyme, and digested to completion using SacI restriction enzyme, the reaction mixture was resolved by gel electrophoresis, the approximately 1.7 kb DNA fragment comprising the β-farnesene synthase coding sequence was gel extracted, and the isolated DNA fragment was ligated into the NcoI SacI restriction enzyme site of the pTrc99A vector, yielding expression plasmid pAM373 (see FIG. 9 for a plasmid map).

Expression plasmids pTrc99A-FSA, pTrc99A-GTS, pTrc99A-PS, pTrc99A-TS were generated by inserting a DNA fragment comprising a nucleotide sequence encoding an α-farnesene synthase ("FSA"), a γ-terpinene synthase ("GTS"), an α-pinene synthase ("APS"), or a terpinolene synthase ("TS") into the pTrc99A vector. The DNA fragment insert was generated synthetically, using as a template for example the coding sequence of the α-farnesene synthase gene of *Picea abies* (GenBank accession number AY473627, REGION: 24 ... 1766), the coding sequence of the β-farnesene synthase gene of *Artemisia annua* (GenBank accession number AY835398), the coding sequence of the γ-terpinene synthase gene of *Citrus limon* (GenBank accession number AF514286 REGION: 30 ... 1832), the coding sequence of the α-pinene synthase gene of *Abies grandis* (GenBank accession number U87909, REGION: 6 ... 1892) or of *Pinus taeda* (GenBank accession number AF543530 REGION: 1 ... 1887), or the coding sequence of the terpinolene synthase gene of *Ocimum basilicum* (GenBank accession number AY693650) or of *Pseudotsuga menziesii* (GenBank accession number AY906866 REGION: 10 ... 1887) or of *Abies grandis* (GenBank accession number AF139206), all nucleotide sequences being codon-optimized for expression in *Escherichia coli*. The DNA fragments for FSA was amplified by PCR from its DNA synthesis construct using the primer sequences SEQ ID NO: 39 and SEQ ID NO: 40. The resulting PCR product was digested to completion using NcoI and SacI restriction enzymes, the reaction mixture was resolved by gel electrophoresis, the approximately 1.7 kb DNA fragment comprising the α-farnesene synthase coding sequence was gel extracted, and the isolated DNA fragment was ligated into the NcoI SacI restriction enzyme site of the pTrc99A vector, yielding expression plasmid pTrc99A-FSA (see FIG. 9 for a plasmid map). The DNA fragments for GTS, APS, and TS were designed to be flanked by a leader XmaI restriction enzyme site and a terminal XbaI restriction enzyme site, and were cloned into compatible restriction enzyme sites of a cloning vector such as a standard pUC or pACYC origin vector, from which they could be liberated again by digesting to completion the DNA synthesis construct using XbaI and XmaI restriction enzymes, resolving the reaction mixture by gel electrophoresis, and gel extracting the 1.7 to 1.9 terpene synthase encoding DNA fragment. The isolated DNA fragments were ligated into the XmaI XbaI restriction enzyme site of vector pTrc99A (Amman et al., *Gene* 40:183-190 (1985)), yielding plasmids pTrc99A-GTS, pTrc99A-APS, or pTrc99A-TS (see FIG. 9 for plasmid maps).

Expression plasmids pRS425-FSA and pRS425-FSB were generated by inserting a nucleotide sequence encoding an a-farnesene synthase ("FSA") or a β-farnesene synthase ("FSB"), respectively, into the pRS425-Gal1 vector (Mumberg et. al. (1994) *Nucl. Acids. Res.* 22(25): 5767-5768). The nucleotide sequence inserts were generated synthetically, using as a template for example the coding sequence of the a-farnesene synthase gene of *Picea abies* (GenBank accession number AY473627, REGION: 24 . . . 1766) or of the β-farnesene synthase gene of *Artemisia annua* (GenBank accession number AY835398), codon-optimized for expression in *Saccharomyces cerevisiae*. The synthetically generated nucleotide sequence was flanked by a 5' BamHI site and a 3' XhoI site, and could thus be cloned into compatible restriction enzyme sites of a cloning vector such as a standard pUC or pACYC origin vector. The synthetically generated nucleotide sequence was isolated by digesting to completion the DNA synthesis construct using BamHI and XhoI restriction enzymes. The reaction mixture was resolved by gel electrophoresis, the approximately 1.7 kb DNA fragment comprising the a-farnesene synthase or β-farnesene synthase coding sequence was gel extracted, and the isolated DNA fragment was ligated into the BamHI XhoI restriction enzyme site of the pRS425-Gal1 vector, yielding expression plasmid pRS425-FSA or pRS425-FSB, respectively.

Expression plasmids pTrc99A-LLS, pTrc99A-LMS, pTrc99A-BPS, pTrc99A-PHS, pTrc99A-CS, and pTrc99A-SS are generated by inserting a nucleotide sequence encoding a linalool synthase ("LLS"), limonene synthase ("LMS"), 3-pinene synthase ("BPS"), β-phellandrene ("PHS"), carene synthase ("CS"), or sabinine synthase ("SS") into the pTrc99A vector. The nucleotide sequence inserts are generated synthetically, using as a template for example the coding sequence of the linalool synthase gene of *Artemisia annua* (GenBank accession number AF154124, REGION: 13 . . . 1764), the coding sequence of the limonene synthase gene of *Abies grandis* (GenBank accession number AF006193 REGION: 73 . . . 1986), the coding sequence of the β-pinene synthase of *Artemisia annua* (GenBank accession number AF276072 REGION: 1 . . . 1749), the coding sequence of the β-phellandrene synthase gene of *Abies grandis* (GenBank accession number AF139205 REGION: 34 . . . 1926), the coding sequence of the carene synthase gene of *Salvia stenophylla* (GenBank accession number AF527416 REGION: 78 . . . 1871), or the coding sequence of the sabinene synthase gene of *Salvia officinalis* (GenBank accession number AF051901 REGION: 26 . . . 1798). The nucleotide sequences encoding the β-pinene, sabinine, and β-phellandrene synthases are flanked by a leader XmaI restriction enzyme site and a terminal XbaI restriction enzyme site, the nucleotide sequences encoding the linalool and carene synthases are flanked by a leader NcoI restriction enzyme site and a terminal XmaI restriction enzyme site, and the nucleotide sequence encoding the limonene synthase is flanked by a leader NcoI restriction enzyme site and a terminal PstI restriction enzyme site. The DNA synthesis constructs are digested to completing using XmaI and XbaI (for the β-pinene, sabinine, and β-phellandrene synthase constructs), NcoI and XmaI restriction enzymes (for the linalool and careen synthase constructs), or XbaI and PstI restriction enzymes (for the limonene synthase construct). The reaction mixtures are resolved by gel electrophoresis, the approximately 1.7 to 1.9 kb DNA fragments are gel extracted, and the isolated DNA fragments are ligated into the XmaI XbaI restriction enzyme site (for the β-pinene, sabinine, and β-phellandrene synthase inserts), the NcoI XmaI restriction enzyme site (for the linalool and carene synthase inserts), or the XbaI PstI restriction enzyme site (for the limonene synthase insert) of the pTrc99A vector, yielding expression plasmids pTrc99A-LLS, pTrc99A-LMS, pTrc99A-BPS, pTrc99A-PHS, pTrc99A-CS, and pTrc99A-SS (see FIG. 9 for plasmid maps).

Example 6

This example describes the generation of *Escherichia coli* host strains useful in the invention.

As detailed in Table 1, the host strains were created by transforming chemically competent *Escherichia coli* parent cells with one or more expression plasmids of Example 1 through 5.

TABLE 1

*E. coli* host strains

| Host Strain | E.coli Parent Strain | Expression Plasmids | Antibiotic Selection |
| --- | --- | --- | --- |
| B32 | DH1 | pMevT | 100 ug/mL carbenicillin |
| B292 | B | pMBIS | |
| B210 | DP | pTrc99A-ADS | 5 ug/mL tetracycline 34 ug/mL chloramphenicol |
| B153 | DH1 | pAM97 | 100 ug/mL carbenicillin |
| B282 | DP | pTrc99A-ADS | 34 ug/mL chloramphenicol |
| B255 | DH1 | pAM128 | 100 ug/mL carbenicillin |
| B256 | DP | pAM113 | 34 ug/mL chloramphenicol |
| B86 | DH1 | pAM52 pMBIS pTrc99A-ADS | 50 ug/mL kanamycin 100 ug/mL carbenicillin |
| B61 | DH1 | pAM25 pBBR1MCS-3 pTrc99A | 5 ug/mL tetracycline |
| B62 | | pAM34 pBBR1MCS-3 pTrc99A | |
| B003 | DH10B | pTrc99A-ADS | 100 µg/ml carbenicillin |

TABLE 1-continued

E. coli host strains

| Host Strain | E.coli Parent Strain | Expression Plasmids | Antibiotic Selection |
|---|---|---|---|
| B617 | | pAM408<br>pTrc99A-ADS | 100 ug/mL carbenicillin<br>50 ug/mL kanamycin |
| B618 | | pAM424<br>pTrc99A-ADS | 100 ug/mL carbenicillin<br>35 µg/ml chloramphenicol |
| B619 | | pAM408<br>pAM424<br>pTrc99A-ADS | 100 µg/ml carbenicillin<br>50 µg/ml kanamycin<br>35 µg/ml chloramphenicol |
| B650 | DH10B | pAM373 | 100 µg/ml carbenicillin |
| B651 | | pAM408<br>pAM373 | 100 µg/ml carbenicillin<br>50 µg/ml kanamycin |
| B652 | | pAM424<br>pAM373 | 100 µg/ml carbenicillin<br>35 µg/ml chloramphenicol |
| B653 | | pAM408<br>pAM424<br>pAM373 | 100 µg/ml carbenicillin<br>50 µg/ml kanamycin<br>35 µg/ml chloramphenicol |
| B286 | DH1 | pAM97-MevB<br>pC9 | 100 ug/mL carbenicillin |
| B287 | | pAM97-MevB<br>pnudF-H | 34 ug/mL chloramphenicol |
| B288 | | pAM97-MevB<br>pyhfR | |
| B291 | | pAM97-MBI<br>pyhfR | |
| B592 | DH1 | pMevT<br>pMBIS<br>pTrc99A-FSA | 100 ug/mL carbenicillin<br>34 ug/mL chloramphenicol |
| B552 | | pMevT<br>pMBIS<br>pAM373 | 100 ug/mL carbenicillin<br>34 ug/mL chloramphenicol<br>5 ug/mL tetracycline |
| Example 21 host cell (production of GTS, APS, TS) | | pMevT<br>pMBIS-gpps<br>pTrc99A-GTS or -APS or -TS | |
| Example 21 host cell (production of LLS, LMS, BPS, PHS, CS, SS) | | pMevT<br>pMBIS-gpps<br>pTrc99A-LLS or -LMS or -BPS or -PHS or -CS or -SS | 100 ug/mL carbenicillin<br>34 ug/mL chloramphenicol<br>5 ug/mL tetracycline |

Host cell transformants were selected on Luria Bertoni (LB) agar containing antibiotics as detailed in Table 1. Single colonies were transferred from LB agar to culture tubes containing 5 mL of LB liquid medium and antibiotics. B003, B617, B618, B619, B650, B651, B652, and B653 host cell transformants were incubated at 30° C. on a rotary shaker at 250 rpm for 30 hours. All other host cell transformants were incubated at 37° C. on a rotary shaker at 250 rpm until growth reached stationary phase. The cells were adapted to minimal media by passaging them through 4 to 5 successive rounds of M9-MOPS media containing 0.8% glucose and antibiotics (see Table 2 for the composition of the M9-MOPS medium). The cells were stored at −80° C. in cryo-vials in 1 mL stock aliquots made up of 400 uL sterile 50% glycerol and 600 uL liquid culture.

TABLE 2

Composition of M9-MOPS Culture Medium

| Component | Quantity (per L) |
|---|---|
| Na2HPO4 7H2O | 12.8 g |
| KH2PO4 | 3 g |
| NaCl | 0.5 g |
| NH4Cl | 1 g |
| MgSO4 | 2 mmol |
| CaCl2 | 0.1 mmol |
| Thiamine | 0.1 ug |
| MOPS buffer pH 7.4 | 100 mmol |
| (NH3)6Mo7O24 4H2O | 3.7 ug |
| H3BO4 | 25 ug |
| CoCl2 | 7.1 ug |
| CuSO4 | 2.4 ug |
| MnCl2 | 16 ug |
| ZnSO4 | 2.9 ug |
| FeSO4 | 0.28 mg |

Example 7

This example demonstrates expression plasmid stability in the absence of antibiotics in an *Escherichia coli* host strain that harbors an expression plasmid comprising the RK2 plasmid replication, segregation, and maintenance system.

A seed culture of host strain B255 was established by adding a stock aliquot of the strain to a 125 mL flask containing 40 mL M9-MOPS, 2% glucose, 0.5% yeast extract, and antibiotics as detailed in Table 1, and by growing the culture overnight.

The seed culture was used to inoculate at an initial $OD_{600}$ of approximately 0.05, two 250 mL flasks each containing 40 mL M9-MOPS medium, 2% glucose, and 0.5% yeast extract. Culture #1 also contained 100 ug/mL carbenicillin and 34 ug/mL chloramphenicol. Culture #2 did not receive any antibiotics. Both cultures were incubated at 37° C. on a rotary shaker at 250 rpm until they reached an $OD_{600}$ of approximately 0.2, at which point the production of amorpha-4,11-diene in the host cells was induced by adding 40 uL of 1M IPTG to the culture medium. At the time of induction, the cultures were overlain with 8 mL of an organic overlay to capture the amorpha-4,11-diene. Samples were taken periodically for a total of 72 hours. Production of amorpha-4,11-diene by the host strain in the 2 cultures was confirmed by GC/MS as described in Example 10.

To assess plasmid stability in the two cell cultures, a sample of each culture was removed at 72 hours and streaked onto a LB agar plate (no antibiotics). After overnight incubation at 37° C., 50 individual colonies derived from each culture were replica-plated onto a LB agar-plus-antibiotics (34 ug/mL chloramphenicol, 100 ug/mL carbenicillin) plate and a LB agar-minus-antibiotics (no antibiotic) plate. After another overnight incubation at 37° C., the LB agar-plus-antibiotics and the LB agar-minus-antibiotics plate were each found to contain approximately 50 colonies, indicating that plasmid retention both in the presence and in the absence of antibiotics in the culture medium had been approximately 100%.

Example 8

This example demonstrates increased specific activity and stability of the *Enterococcus faecalis* HMGR compared to the *Saccharomyces cerevisiae* tHMGR in an *Escherichia coli* host strain.

Seed cultures of host strains B61 and B62 were established by adding a stock aliquot of each strain to 125 mL flasks containing 20 mL M9-MOPS medium, 0.8% % glucose, and antibiotics as detailed in Table 5, and by growing the cultures to saturation. The seed cultures were diluted 1:100 into 140 mL of fresh medium in a 500 mL flask, and grown again to an $OD_{550}$ of approximately 0.1, at which point production of amorpha-4,11-diene was induced by adding 140 uL 1 M IPTG to each culture. At 4, 12, 20, 28, 36, and 49 hours post-induction, samples were removed from each culture, and cells were pelleted by centrifugation. The cell pellets were snap frozen on dry ice, and then stored at –80° C.

To conduct enzyme assays, cell pellets were thawed on ice, and then lysed using Bugbuster (Novagen, Madison, Wis.) containing protease inhibitor mix #3 (Calbiochem, San Diego, Calif.), benzonase (20 µL oer5 mL bugbuster; Novagen, Madison, Wis.), and lysozyme (30 ug/mL). Enzyme activity of the *Saccharomyces cerevisiae* tHMGR was assayed in 50 mM Tris HCl (pH7.5), 0.2 mM NADPH (Sigma, St. Louis, Mo.), and 0.3 mM DL-3-hydroxy-3-methylglutaryl coenzyme A (HMG-CoA) sodium salt (Sigma, St. Louis, Mo.). The assay was started by adding cell lysate, and the disappearance of NADPH was monitored by absorbance at 340 nM. To account for non-specific disappearance of NADPH, results obtained in a control assay lacking HMG-CoA were subtracted from results obtained in test samples. Enzyme activity of the *Enterococcus faecalis* HMGR was measured similarly except that the assay buffer contained 100 mM potassium phosphate buffer (pH6.5), 0.4 mM NADPH, 1.0 mM EDTA, and 100 mM KCl.

Protein assays were done by the method of Bradford ((1976) *Anal Biochem.* 72:248-254). Specific activities were calculated as Δnmol NADPH/min/mg protein.

Example 9

This example describes the calibration of $OD_{600}$ with dry cell weight ("DCW").

To obtain the relationship between DCW and OD600, a representative strain, B32, was grown in high cell density processes similar to those described in Examples 10-12. Samples were taken throughout the runs, and the $OD_{600}$ and DCW were measured for each sample. To determine the DCW, the cells were pelleted and the supernatant discarded. The cell pellet was washed once with water, and was then dried in an oven at 80° C. for at least 3 days. The tubes containing cell pellets were weighed, the weight of the tube was subtracted from the measured weights, and the remaining weight was divided by the initial volume of each sample (0.0015 L) to obtain the DCW.

Example 10

This example demonstrates increased production of amorpha-4,11-diene in *Escherichia coli* host strains expressing the *Staphylococcus aureus* HMGR and HMGS compared to host strains expressing the *Saccharomyces cerevisiae* tHMGR and HMGS.

Seed cultures of host strains B32, B153, B210, B282, B292, B86, B255, and B256 were established by adding a stock aliquot of each strain to separate 125 mL flasks containing 25 mL M9-MOPS medium, 0.8% glucose, and antibiotics as detailed in Table 1, and by growing the cultures overnight.

The seed cultures were used to inoculate at an initial $OD_{600}$ of approximately 0.05 separate 250 mL flasks containing 40 mL M9-MOPS medium, 2% glucose, and antibiotics. The cultures were incubated at 30° C. on a rotary shaker at 250 rpm until they reached an $OD_{600}$ of approximately 0.2, at which point the production of amorpha-4,11-diene in the host cells was induced by adding 40 uL of 1M IPTG to the culture medium. The cultures were overlain with 8 mL of an organic overlay (e.g., dodecane, methyl oleate or isopropyl myristate). Samples of the organic overlay layer and the broth were taken once a day for 72 hours. Broth samples were used to measure the $OD_{600}$. Amorpha-4,11-diene concentration was measured by transferring 5 uL of the organic overlay layer to a clean glass vial containing 500 uL ethyl acetate spiked with beta- or trans-caryophyllene as an internal standard.

The organic overlay/ethyl acetate samples were analyzed on a Hewlett-Packard 6890 gas chromatograph/mass spectrometer (GC/MS) by scanning only for two ions, the molecular ion (204 m/z) and the 189 m/z ion, as described in Martin et al. (2001) *Biotechnol. Bioeng.* 75:497-503. To expedite run times, the temperature program and column matrix was modified to achieve optimal peak resolution and the shortest overall runtime. A 1 uL sample was separated on the GC using a DB-XLB column (available from Agilent Technologies, Inc., Palo Alto, Calif.) and helium carrier gas. The temperature program for the analysis was as follows: 100° C. for 0.75 minutes, increasing temperature at 60° C./minute to a temperature of 300° C., and a hold at 300° C. for 0.5 minutes. The resolved samples were analyzed by a Hewlett-Packard model 5973 mass-selective detector that monitored ions 189 and 204 m/z. Previous mass spectra demonstrated that the amorpha-4,11-diene synthase product was amorpha-4,11-diene, and that amorpha-4,11-diene had a retention time of 3.7 minutes using this GC protocol. Beta- or trans-caryophyllene was used as an internal standard for quantitation. Amorpha-4,11-diene titer was calculated using the ratio of internal standard to amorpha-4,11-diene peak areas based upon a quantitative calibration curve of purified amorpha-4,11-diene (0.63-10 mg/L of KJF17-109-3) in caryophyllene-spiked ethyl acetate.

Example 11

This example demonstrates increased production of amorpha-4,11-diene by an *Escherichia coli* host strain grown at suboptimal temperature.

A seed culture of host strain B32 was established by adding 0.5 mL of a stock aliquot of the strain to a 250 mL flask containing 50 mL M9-MOPS medium and antibiotics as detailed in Table 1, and by growing the culture overnight at 37° C. on a rotary shaker at 250 rpm.

The seed culture was used to inoculate at an initial $OD_{600}$ of approximately 0.05 four 250 mL flasks, each containing 40 mL fermentor batch medium (see Table 6 for medium composition), 100 mM MOPS buffer pH7.1, and antibiotics. The cultures were incubated on a rotary shaker at 250 rpm at either 30° C. or 37° C. until they reached an $OD_{600}$ of 0.18 to 0.22, at which point the production of amorpha-4,11-diene in the host cells was induced by adding 40 uL of 1M IPTG to the culture medium. At the time of induction, the cultures were overlain with 8 mL of an organic overlay to capture the amorpha-4,11-diene. Samples were taken once a day, and analyzed as described in Example 10.

Example 12

This example demonstrates increased production of amorpha-4,11-diene by an *Escherichia coli* host strain grown under restricted carbon source conditions.

A seed culture of host strain B32 for fermentation runs 050608-1 and 050629-1 was established by adding 0.25 uL of a stock aliquot of the strain to a 250 mL flask containing 50 mL M9-MOPS medium and antibiotics as detailed in Table 1, and by incubating the culture at 37° C. on a rotary shaker at 250 rpm until it reached an $OD_{600}$ of 1 to 2.

A seed culture of host strain B32 for fermentation run 060403-3 was established by adding a stock aliquot of the strain to a 250 mL flask containing 50 mL M9-MOPS medium and antibiotics as detailed in Table 1, and by incubating the culture overnight at 37° C. on a rotary shaker at 250 rpm. The seed culture was used to inoculate at an initial $OD_{600}$ of approximately 1 a 250 mL flask containing 40 mL M9-MOPS medium and antibiotics, and the culture was again incubated at 37° C. on a rotary shaker at 250 rpm until it reached an $OD_{600}$ of 3 to 5.

For all fermentation processes, the $KH_2PO_4$, $K_2HPO_4$ $3H_2O$, EDTA, citric acid, and $(NH_4)_2SO_4$ were heat sterilized in the bioreactor (2 L Applikon Bioconsole ADI 1025s with ADI 1010 controllers, Applikon Biotechnology, Foster City, Calif.). The remaining media components were filter sterilized as stock solutions and injected through the headplate. Table 3 shows the final media composition for fermentation runs 050608-1 and 050629-1. Table 4 shows the final media composition for fermentation run 060403-3. The starting volume for run 050608-1 was 0.8 L, the starting volume for 050629-1 was 1.2 L and the starting volume for 060403-3 was 1 L. All runs were inoculated by injecting 50 mL of the seed culture through the headplate.

TABLE 3

Composition of Fermentation Medium of Fermentation Runs 050608-1 and 050629-1

| Component | Batch Medium (per L) | Feed Solution (per L) |
|---|---|---|
| Glucose | 5 g | 590-650 g |
| $KH_2PO_4$ | 4.2 g | — |
| $K_2HPO_4$ $3H_2O$ | 15.7 g | — |
| Citric acid | 1.7 g | — |
| $(NH_4)_2SO_4$ | 2 g | — |
| $MgSO_4$ $7H_2O$ | 1.2 g | 12 g |
| EDTA | 8.4 mg | 13 g |
| $CoCl_2$ $6H_2O$ | 0.25 mg | 0.4 mg |
| $MnCl_2$ $4H_2O$ | 1.5 mg | 2.35 mg |
| $CuCl_2$ $2H_2O$ | 0.15 mg | 0.25 mg |
| $H_3BO_4$ | 0.3 mg | 0.5 mg |
| $Na_2MoO_4$ $2H_2O$ | 0.25 mg | 0.4 mg |
| $Zn(CH_3COO)_2$ $2H_2O$ | 1.3 mg | 1.6 mg |
| Fe(III)citrate hydrate | 10.0 mg | 4.0 mg |
| Thiamine HCl | 4.5 mg | — |
| Carbenicillin | 100 ug | 100 ug |
| Tetracycline | 5 ug | 5 ug |
| Chloramphenicol | 34 ug | 34 ug |

TABLE 4

Composition of Fermentation Medium of Fermentation Run 060403-3

| Component | Batch medium (per L) | Feed solution (per L) |
|---|---|---|
| Glucose | 15 g | 650 g |
| $KH_2PO_4$ | 4.2 g | — |
| $K_2HPO_4$ $3H_2O$ | 15.7 g | — |
| Citric acid | 1.7 g | — |
| $(NH_4)_2SO_4$ | 2 g | — |
| $MgSO_4$ $7H_2O$ | 1.2 g | 12 g |
| EDTA | 8.4 mg | 13 mg |
| $CoCl_2$ $6H_2O$ | 2.5 mg | 4 mg |
| $MnCl_2$ $4H_2O$ | 15 mg | 23.5 mg |
| $CuCl_2$ $2H_2O$ | 1.5 mg | 2.5 mg |
| $H_3BO_4$ | 3 mg | 5 mg |
| $Na_2MoO_4$ $2H_2O$ | 2.5 mg | 4 mg |
| $Zn(CH_3COO)_2$ $2H_2O$ | 13 mg | 16 mg |
| Fe(III)citrate hydrate | 100 mg | 40 mg |
| Thiamine HCl | 4.5 mg | — |
| Carbenicillin | 100 ug | 100 ug |
| Tetracycline | 5 ug | 5 ug |
| Chloramphenicol | 34 ug | 34 ug |

For fermentation run 050608-1 (excess carbon), the feed was initiated at induction, and feed rates were adjusted manually. For fermentation run 050629-1 (carbon-restricted), the feed was delivered to the fermentor according to the protocol shown in Table 5. For fermentation run 060403-3 (lowest carbon), the feed was started automatically when the initial glucose bolus (15 g) was exhausted and the dissolved oxygen spiked. Up to a maximum of 27.6 g/hr, the rate of the feed was calculated according to the following equation:

$$m_s(t) = S(t_0)\mu e^{\mu(t-t_0)}$$

$\mu = 0.12$ $S(t_0) = 15$ g wherein $t_0$ is the time at which the initial glucose was depleted. Upon reaching the maximum rate, the glucose feed was restricted to a rate of 9.5 g/hr, and held constant at this rate for the remainder of the run.

TABLE 5

Feed Protocol for Fermentation Run 050629-1

| Run Time (hours) | Glucose Feed Rate (g/hr) |
|---|---|
| 0 | 0 |
| 7 | 0.37 |
| 10 | 0.74 |
| 12 | 1.11 |
| 14 | 1.48 |
| 16 | 2.22 |
| 18 | 2.96 |
| 20 | 3.69 |
| 22 | 4.80 |
| 24 | 5.91 |
| 31 | 7.39 |
| 33 | 5.54 |
| 47 | 3.69 |

Runs 050608-1 and 050629-1 were carried out at 37° C. Airflow in the bioreactor was set at 1-2 L/min; pH was maintained at 7 using ammonium hydroxide and/or sodium hydroxide; initial agitation was 500-600 rpm; foam was controlled with antifoam B (Sigma-Aldrich, St. Louis, Mo.); the dissolved oxygen levels were maintained above 30% using an agitation cascade. After 5-6 hours of cultivation, production of amorpha-4,11-diene by the host cells was induced by adding 0.8 mL of 1 M IPTG to run 050608-1 and 1.2 mL IPTG to run 050629-1. Upon induction, the culture temperature was reduced to 30° C.

Run 060403-3 was carried out at 30° C. Airflow in the bioreactor was set at 1-2 L/min; pH was maintained at 7 using ammonia hydroxide. Dissolved oxygen was maintained above 30% by an agitation cascade and oxygen enrichment. At an $OD_{600}$ of approximately 28 (19 hours after inoculation), production of amorpha-4,11-diene by the host cells was induced by adding 1 mL 1 M IPTG.

Amorpha-4,11-diene was captured and extracted according to two different protocols. For runs 050608-1 and 050629-1, volatile amorpha-4,11-diene present in the off-gas was captured by venting the off-gas through a gas-washer containing 200 mL heptanol. The heptanol was then diluted into ethyl acetate until the amorpha-4,11-diene concentration in the sample was between 0.63 mg/L and 20 mg/L. For run 060403-3, amorpha-4,11-diene was captured in the bioreactor by adding 200 mL of an organic overlay to the fermentor at the time of induction. Product concentration was measured by combining 25 uL broth plus organic overlay with 975 uL acetonitrile, shaking the sample at maximum speed on a Fisher Vortex Genie 2™ mixer (Scientific Industries, Inc., Bohemia, N.Y.) for at least 3 minutes, removing cells from the sample by centrifugation, and diluting the acetonitrile solution into ethyl acetate until the amorpha-4.11-diene concentration in the sample was between 0.63 and 20 mg/L. The ethyl acetate samples were analyzed by GC/MS as described in Example 10.

Example 13

This example demonstrates increased amorpha-4,11-diene production by an *Escherichia coli* host strain grown under restricted carbon source conditions and at suboptimal temperature.

A seed culture of host strain B153 was established by adding a stock aliquot of the strain to a 250 mL flask containing 50 mL M9-MOPS medium and antibiotics as detailed in Table 1, and growing the culture at 37° C. on a rotary shaker at 250 rpm to an $OD_{600}$ of 3.5 to 4.5.

2 L bioreactors (Biocontroller ADI 1010 with Bioconsole ADI 1025, Applikon Biotechnology, Foster City, Calif.) were set up and run in the same way as described in Example 12 for run 060403-3, except that strain and induction time were varied.

Production of amorpha-4,11-diene in the host cells was induced by adding 1 mL of 1 M IPTG to the culture medium. Amorpha-4,11-diene was captured and extracted according to two different protocols. In one method, volatile amorpha-4,11-diene present in the off-gas was captured by venting the off-gas through a gas-washer containing 200 mL heptanol. The heptanol was then diluted into ethyl acetate until the amorpha-4,11-diene concentration in the sample was between 0.63 and 20 mg/L. in another, amorpha-4,11-diene was captured by adding 200 mL of an organic overlay to the fermentor at the time of induction.

Amorpha-4,11-diene was extracted from the culture medium by combining 25 uL broth with 975 uL acetonitrile, shaking the sample at maximum speed on a Fisher Vortex Genie 2™ mixer (Scientific Industries, Inc., Bohemia, N.Y.) for at least 3 minutes, removing cells from the sample by centrifugation, and diluting the acetonitrile solution into ethyl acetate until the amorpha-4.11-diene concentration in the sample was between 0.63 and 20 mg/L. The ethyl acetate samples were analyzed by GC/MS as described in Example 10.

Example 14

This example demonstrates increased amorpha-4,11-diene production by an *Escherichia coli* host strain grown under restricted carbon and nitrogen source conditions and at suboptimal temperature.

A seed culture of host strain B86 was established by adding a stock aliquot of the strain to a 250 mL flask containing 50 mL M9-MOPS medium and antibiotics as detailed in Table 1. The culture was grown overnight at 37° C. on a rotary shaker at 250 rpm, sub-cultured the following morning into the same medium at an $OD_{600}$ of approximately 1, and grown again at 37° C. and 250 rpm to an $OD_{600}$ of 3 to 5.

Four 2 L bioreactors (Biocontroller ADI 1010 with Bioconsole ADI 1025, Applikon Biotechnology, Foster City, Calif.) were set up and run in the same way as described in Example 12 for run 060403-3, except that the nitrogen restricted runs did not contain ammonia sulfate in the feed.

An exponential glucose feed with a 6 hour doubling time was initiated automatically when the initial glucose bolus (15 g) was exhausted and the dissolved oxygen spiked. Up to a maximum of 30.4 g/hr, the rate of the feed was calculated according to the following equation:

$$m_s(t)=S_0\mu e^{\mu(t-t_0)}$$

$\mu=0.12$ min$^{-1}$
$S_0=15$ g wherein μ is the specific growth rate, and to is the time at which the initial glucose bolus was depleted. Upon reaching the maximum rate, the glucose feed was reduced to a rate of 11.4 g/hr, and held constant at this rate for the remainder of the run. In fermentation runs 060710-4, 060724-5, and 060619-5 (carbon- and nitrogen-restricted), the glucose feed was further reduced when ammonia restriction lead to glucose accumulation in the medium.

Fermentation was carried out at the reduced temperature of 30° C. Airflow in the bioreactor was set at 1 vvm; initial agitation was at 700 rpm; foam was controlled with antifoam B (Sigma-Aldrich, St. Louis, Mo.); and dissolved oxygen tension was controlled at 40% using an agitation cascade (700-1,200 rpm) and oxygen enrichment. In fermentation run 060327-3 (carbon-restricted), the pH was maintained at 7 using 20% $NH_4OH$; in fermentation runs 060710-4, 060724-5, and 060619-5 (carbon- and nitrogen-restricted), pH was maintained at 7 initially using 20% $NH_4OH$, and starting at 72 hours using a 50/50 mixture of 2.5 N NaOH and 10 N $NH_4OH$, to further restrict the amount of ammonia going into the fermentor.

Production of amorpha-4,11-diene in the host cells was induced at an $OD_{600}$ of approximately 30 by adding 1 mL of 1 M IPTG to the culture medium.

Amorpha-4,11-diene was captured by overlaying the medium with 10% (v/v) of an organic overlay. Amorpha-4,11-diene was then extracted by combining 25 uL of broth with 975 uL methanol, shaking the sample at maximum speed on a Fisher Vortex Genie 2™ mixer (Scientific Industries, Inc., Bohemia, N.Y.) for at least 15 minutes, removing cells from the sample by centrifugation, and adding 10 uL of the methanol solution to 990 uL ethyl acetate containing 10 uL/L trans-caryophylene.

Samples were analyzed by GC/MS as described in Example 10.

Example 15

This example describes the production of amorpha-4,11-diene via the DXP pathway in an *Escherichia coli* host strain.

Seed cultures of host strains B003, B617, B618, and B619 were established by adding a stock aliquot of each strain to separate 125 mL flasks containing 25 mL M9-MOPS and antibiotics as detailed in Table 1, and by growing the cultures overnight.

The seed cultures were used to inoculate at an initial $OD_{600}$ of approximately 0.05, separate 250 mL flasks containing 40 mL M9-MOPS medium, 45 ug/mL thiamine, micronutrients, 1.00E-5 mol/L FeSO4, 0.1 M MOPS, 0.5% yeast extract, 20 g/L of D-glucose, and antibiotics. Cultures were incubated at 30° C. in a humidified incubating shaker at 250 rpm until they reached an $OD_{600}$ of 0.2 to 0.3, at which point the production of amorpha-4,11-diene in the host cells was induced by adding 40 uL of 1M IPTG to the culture medium.

At the time of induction, the cultures were overlain with 8 mL of an organic overlay to capture the amorpha-4,11-diene. Samples were taken at various time points, and amorpha-4,11-diene was extracted and analyzed by GC/MS as described in Example 10. Experiments were performed using 2 independent clones of each host strain, and results were averaged. Deviation between samples was found to be less than 10%.

Example 16

This example describes the production of 3-methyl-but-3-en-1-ol and 3-methyl-but-2-en-1-ol in *Escherichia coli* host strains.

Seed cultures of host strains B286, B287, B288, and B291 were established by streaking out a stock aliquot of each strain on LB agar containing antibiotics as detailed in Table 1. Three independent colonies were picked for each strain, and each colony was inoculated into 7 mL of LB media containing antibiotics. The cultures were grown overnight at 37° C. on a rotary shaker at 250 rpm until late exponential phase. The cultures were then inoculated at an $OD_{600}$ of approximately 0.05, into a 250 mL flask containing 40 ml of M9-MQPS, 2% glucose, 0.5% yeast extract, and antibiotics. The cultures were grown overnight at 37° C. on a rotary shaker at 250 rpm until they reached an $OD_{600}$ of approximately 0.2, at which point they were induced by adding 40 uL of 1 M IPTG. The cultures were grown for 72 hours at 30° C. on a rotary shaker at 250 rpm. One to two times per day, the $OD_{600}$ of each culture was measured, and a 700 uL sample was removed. To extract the 3-methyl-but-3-en-1-ol and 3-methyl-but-2-en-1-ol from the culture broth, 600 uL of ethyl acetate was added to 300 uL of each removed sample. The sample was then vortexed for 15 minutes, and 400 uL of the upper ethyl acetate phase was transferred to a clean glass vial for analysis.

The samples were analyzed on a Hewlett-Packard 6890 gas chromatograph/mass spectrometer (GC/MS). A 1 uL sample was separated on the GC using a DB-5 column (Agilent Technologies, Inc., Palo Alto, Calif.) and helium carrier gas. The temperature program for the analysis was as follows: 60° C. for 3 minutes, increasing temperature at 60° C./minute to a temperature of 300° C., and a hold at 300° C. for 2 minutes. The total run time was 9 minutes. The resolved samples were analyzed by a Hewlett-Packard model 5973 mass selective detector. Previous mass spectra demonstrated that 3-methyl-3-buten-1-ol and 3-methyl-2-buten-1-ol have a retention time of 2.067 minutes using this GC protocol. To focus detection on 3-methyl-but-3-en-1-ol and 3-methyl-but-2-en-1-ol, a selective-ion-monitoring method was employed that monitors only ions 56 and 68 in 3-methyl-but-3-en-1-ol and 3-methyl-but-2-en-1-ol.

Example 17

This example describes the production of amorpha-4,11-diene by a *Saccharomyces cerevisiae* host strain.

The generation of host strain EPY224 is described in Ro et al. (*Nature* 440: 940-943; 2006) and in PCT Patent Publication WO2007/005604. Host strain EPY224 was cured of expression plasmid pRS425ADS by growth in YPD medium (Methods in Yeast Genetics: A Cold Spring Harbor Laboratory Course Manual, 2005 ed., ISBN 0-87969-728-8), plating for single colonies on YPD agar, and then patching single colonies onto CSM-Met His agar and CSM-Met Leu agar. Clones that grew on CSM-Met His agar but not on CSM-Met Leu agar were cured (i.e., had lost the plasmid pRS425ADS). One such clone was designated EPY300. EPY300 was transformed with expression plasmid pRS425-ADS-LEU2d, a plasmid identical to pRS425-ADS except that instead of LEU2 it contains a LEU2d selection marker (Erhart and Hollenberg (1983) *J. Bacteriol.* 156: 625-635) yielding host strain Y185.

Y185 host cell transformants were selected on synthetic defined media, containing 2% glucose and all amino acids except histidine, leucine, and methionine (CSM-glucose; MP Biomedicals, Solon, Ohio). The host strain EPY300 is auxotrophic for leucine biosynthesis (leu2), but expression plasmid pRS425-ADS-LEU2d in Y185 restores leucine prototrophy (LEU2). Single colonies were patched onto selective medium (CSM-glucose-histidine, leucine, methionine), and grown for 2 days. The cells were scraped from the plate and transferred to 1 mL of 25% (v/v) glycerol in a cryotube. The suspension was mixed, and then stored at −80° C.

Seed flasks of host strain Y185 were established by adding a stock aliquot of the strain to a 125 mL flask containing 25 mL of CSM-glucose lacking leucine and methionine, and by growing the cultures overnight. The cultures were used to inoculate at an initial $OD_{600}$ of approximately 0.05 a 250 mL baffled flask containing 40 mL of synthetic defined media lacking leucine, and containing 0.2% glucose, 1.8% galactose, and 1 mM methionine. The culture was incubated at 30° C. on a rotary shaker at 200 rpm. Because the presence of glucose in the media prevents induction of the GAL1 promoter by galactose, amorpha-4,11-diene production was not induced until the cells had used up the glucose in the media and had switched to using galactose as their main carbon source. At the time of inoculation, the cultures were overlain with 8 mL of an organic overlay to capture the amorpha-4,11-diene. Samples were taken at 72 hours by transferring 5 uL of the organic solvent layer to a clean glass vial containing 500 uL ethyl acetate containing a known concentration of beta- or trans-caryophyllene as an internal standard.

The organic overlay/ethyl acetate samples were analyzed on a Hewlett-Packard 6890 gas chromatograph/mass spectrometer (GC/MS) as described in Example 10.

After 72 hours of growth, 3 yeast cultures were found to produce 60.68, 54.48, and 59.25 mg/L amorpha-4,11-diene.

Example 18

This example describes the production of amorpha-4,11-diene in an *Saccharomyces cerevisiae* host strain where the host strain includes a native mevalonate pathway as well as a heterologous mevalonate pathway that is under control of a heterologous regulatory control.

Yeast strains CEN.PK2-1C (Y002) (MATA; ura3-52; trp1-289; leu2-3,112; his3Δ1; MAL2-8C; SUC2) and CEN.PK2-1D (Y003) (MATalpha; ura3-52; trp1-289; leu2-3,112; his3Δ1; MAL2-8C; SUC2) (J. P. van Dijken et al., Enzyme Microb Technol 26, 706 (Jun. 1, 2000) were cultivated in either standard rich medium (YPD) or in defined synthetic medium (D. Rose, F. Winston, P. Heiter, Methods in yeast genetics: a laboratory course manual. (Cold Spring Harbor Laboratory Press, Cold Spring Harbor, N.Y., 1990) lacking appropriate nutrients allowing for selection of integrative transformants, plasmid retention, and meiotic progeny.

DNA-mediated transformations into S. cerevisiae were conducted using the lithium acetate procedure as described by R. H. Schiestl, R. D. Gietz, Curr Genet 16, 339 (December, 1989). All gene disruptions and replacements were confirmed by phenotypic analysis, colony polymerase chain reaction ("PCR") and sequencing of amplified genomic DNA. Plasmids pAM489-pAM498 were constructed using the pCR 2.1 (Invitrogen, Carlsbad Calif.) and are schematically described by FIG. 7A-C and Table 6. The HISMX marker sequences are described in M. S. Longtine et al., Yeast 14, 953 (July, 1998). Propagation of plasmid DNA was performed in Escherichia coli strain DH5α.

exponentially growing Y93 and Y94 as described above. ade1-strains were selected for growth in the absence of leucine supplementation and confirmed by diagnostic PCR. The resultant clones were given the designation Y176 (MAT A) and Y177 (MAT alpha).

To generate S. cerevisiae strain Y188, 2 μg's of plasmid DNA from pAM491 (SEQ ID NO: 48) and pAM495 (SEQ ID NO:49), respectively, were digested overnight with PmeI (New England Biolabs, Beverly, Mass.) and introduced into exponentially growing Y176 as described above. Positive recombinants were selected for by growth on medium lacking uracil and histidine. Integration into the correct genomic locus was confirmed by diagnostic PCR.

To generate S. cerevisiae strain Y189, 2 μg's of plasmid DNA from pAM489 (SEQ ID NO: 50) and pAM497 (SEQ ID NO: 51), respectively, were digested overnight with PmeI and introduced into exponentially growing Y177 as described above. Positive recombinants were selected for by growth on medium lacking tryptophan and histidine. Integration into the correct genomic locus was confirmed by diagnostic PCR.

Approximately $1 \times 10^7$ cells from Y188 and Y189 were mixed on a YPD medium plate for 6 hours at room temperature to allow for mating. The mixed cell culture was then

TABLE 6

| Strain | 5'HR | Gene #1 | Crick Promoter | Watson Promoter | Gene #2 | Genetic Marker | 3'HR |
|---|---|---|---|---|---|---|---|
| pAM489 | TRP1 | tHMGR | GAL1 | GAL10 | ERG20 | TRP1 | TRP1 |
| pAM490 | TRP1 | tHMGR | CUP1 | CUP1 | ERG20 | TRP1 | TRP1 |
| pAN491 | URA3 | tHMGR | GAL1 | GAL10 | ERG13 | URA3 | URA3 |
| pAM492 | URA3 | IDI1 | CUP1 | CUP1 | tHMGR | URA3 | URA3 |
| pAM493 | ADE1 | tHMGR | GAL1 | GAL10 | IDI1 | ADE1 | URA3 |
| pAM494 | ADE1 | tHMGR | CUP1 | CUP1 | IDI1 | ADE1 | ADE1 |
| pAM495 | HIS3 | ERG12 | GAL1 | GAL10 | ERG10 | HISMX | HIS3 |
| pAM496 | HIS3 | ERG12 | CUP1 | CUP1 | ERG10 | HISMX | HIS3 |
| pAM497 | LEU2 | ERG19 | GAL1 | GAL1 | ERG8 | HISMX | LEU2 |
| pAM498 | LEU2 | ERG19 | CUP1 | CUP1 | ERG8 | HISMX | LEU2 |

S. cerevisiae strains Y002 and Y003 were prepared for introduction of inducible mevalonate pathway genes by the following. The ERG9 promoter was replaced with the S. cerevisiae MET3 promoter by PCR amplification of the KanMX-PMET3 region from pAM328 (SEQ ID NO: 43) using primers 50-56-pw100-G (SEQ ID NO: 44) and 50-56-pw101-G (SEQ ID NO: 45) containing 45 basepairs of homology to the native ERG9 promoter. 10 μg of the resulting PCR product was transformed into exponentially growing Y002 and Y003 strains using 40% w/w polyethelene glycol 3350 (Sigma-Aldrich St Louis, Mo.), 100 mM lithium acetate (Sigma), 10 μg Salmon Sperm DNA (Invitrogen) and incubation at 30° C. for 30 minutes followed by a 42° C. heat shock for 30 minutes (as described by Schiestl & Gietz, Curr. Genet. 16: 339 (1989)). Positive recombinants were identified by their ability to grow on rich medium containing 0.5 μg/ml Geneticin (Invitrogen Co, Carlsbad, Calif.) and confirmed by diagnostic PCR. The resultant clones were given the designation Y93 (MAT A) and Y94 (MAT alpha). Next, the ADE1 open reading frame was replaced with the Candida glabrata LEU2 gene (CgLEU2). The 3.5 KB CgLEU2 genomic locus was amplified from C. glabrata genomic DNA (ATCC, Manassas, Va.) using primers 61-67-CPK066-G (SEQ ID NO: 46) and 61-67-CPK067-G (SEQ ID NO: 47) containing 50 basepairs of flanking homology to the ADE1 open reading frame (ORF). 10 μg of the resulting PCR product was transformed into plated to medium lacking histidine, uracil and tryptophan to select for growth of diploid cells. 2 μg of plasmid DNA from pAM493 (SEQ ID NO: 52) was digested overnight with PmeI and introduced into exponentially growing diploid cells as described above. Positive recombinants were selected for by growth on medium lacking adenine. Integration into the correct genomic locus was confirmed by diagnostic PCR. The resultant strain was given the designation Y238.

To generate haploid strains containing the full complement of introduced genes, Y238 was sporulated in 2% potassium acetate and 0.02% raffinose liquid medium. Approximately 200 genetic tetrads (tetrads are four-spored meiotic products) were isolated using a Singer Instruments MSM300 series micromanipulator (Singer Instrument Co, LTD. Somerset, UK). Independent genetic isolates containing the appropriate complement of introduced genetic material were identified by their ability to grow in the absence of adenine, histidine, uracil, and tryptophan. Integration of all introduced DNA was confirmed by diagnostic PCR. The resultant strains were given the designation Y210 (MAT A) and Y211 (MAT alpha).

2 μg of plasmid DNA from pAM426 (SEQ ID NO:53), containing S. cerevisiae condon optimized Amorphadeine Synthase (ADS) expressed from the S. cerevisiae GAL1 promoter, was introduced into exponentially growing Y210 and Y211 as described above. S. cerevisiae strains that contained the pAM426 plasmid were selected for by their ability to grow in the absence of leucine supplementation. The resultant strains were given the designation Y225 (MAT A) and Y227 (MAT alpha).

2 μg of plasmid DNA from pAM322 (SEQ ID NO: 54), containing *S. cerevisiae* condon optimized Amorphadeine Synthase (ADS) and cytochrome P450 monooxygenase (AMO) expressed from the *S. cerevisiae* GAL1 and the cytochrome P450 oxidoreductase (CPR) expressed from the *S. cerevisiae* GAL10 promoter, was introduced into exponentially growing Y210 and Y211 as described above. *S. cerevisiae* strains that contained the pAM322 plasmid were selected for by their ability to grow in the absence of leucine supplementation. The resultant strains were given the designation Y222 (MAT A) and Y224 (MAT alpha).

Example 19

This example describes the production of a-farnesene or β-farnesene in *Escherichia coli* host strains.

Seed cultures of host strains B552 and B592 were established by adding a stock aliquot of each strain to a 125 mL flask containing 25 mL M9-MOPS, 0.8% glucose, 0.5% yeast extract, and antibiotics as detailed in Table 1, and by growing the cultures overnight.

The seed cultures were used to inoculate at an initial $OD_{600}$ of approximately 0.05, 250 mL flasks containing 40 mL M9-MOPS, 2% glucose, 0.5% yeast extract, and antibiotics. Cultures were incubated at 30° C. on a rotary shaker at 250 rpm until they reached an $OD_{600}$ of approximately 0.2, at which point the production of a-farnesene or P-farnesene in the host cells was induced by adding 40 uL of 1 M IPTG. At the time of induction, the cultures were overlain with 8 mL of an organic overlay to capture the a-farnesene. Samples were taken every 24 hours up to 120 hours (total of 5 time points) by transferring 2 uL to 10 uL of the organic overlay layer to a clean glass vial containing 1 mL ethyl acetate spiked with trans-caryophyllene as an internal standard. In addition, 1 mL aliquots of the cultures were spun down, cell pellets were resuspended in 250 uL sterile water, and the cell suspensions were transferred to a glass vial containing 1 mL ethyl acetate spiked with trans-caryophyllene as an internal standard. In addition, 0.5 mL aliquots of the whole culture broth were added to a glass vials containing 1 mL ethyl acetate spiked with trans-caryophyllene as an internal standard. The whole culture broth samples were extracted in the ethyl acetate by vortexing the glass vials for 10 minutes, after which 600 uL of the ethyl acetate extraction was transferred to a clean glass vial.

The organic overlay/ethyl acetate samples and the ethyl acetate-extracted whole culture broth samples were analyzed on an Agilent 6890N gas chromatograph equipped with an Agilent 5975 mass spectrometer (GC/MS) in full scan mode (50-500 m/z). To expedite run times, the temperature program and column matrix was modified to achieve optimal peak resolution and the shortest overall runtime. A 1 uL sample was separated using a HP-5MS column (Agilent Technologies, Inc., Palo Alto, Calif.) and helium carrier gas. The temperature program for the analysis was as follows: 150° C. hold for 3 minutes, increasing temperature at 25° C./minute to a temperature of 200° C., increasing temperature at 60° C./minute to a temperature of 300° C., and a hold at 300° C. for 1 minute. Previous mass spectra demonstrated that the β-farnesene synthase product was β-farnesene, and that β-farnesene had a retention time of 4.33 minutes using this GC protocol. Farnesene titers were calculated by comparing generated peak areas against a quantitative calibration curve of purified β-farnesene (Sigma-Aldrich Chemical Company, St. Louis, Mo.) in trans-caryophyllene-spiked ethyl acetate.

Host strain B592 produced approximately 400 mg/L of α-farnesene at 120 hours (averaged over 3 independent clones), and had a maximal specific productivity of approximately 46 mg/L/$OD_{600}$. Host strain B552 produced approximately 1.1 g/L of β-farnesene at 120 hours (averaged over 3 independent clones), and had a maximal specific productivity of approximately 96 mg/L/$OD_{600}$ (1 representative clone).

Example 20

This example describes the production of 0-farnesene via the DXP pathway in an *Escherichia coli* host strain.

Seed cultures of host strains B650, B651, B652, and B653 were established by adding a stock aliquot of each strain to separate 125 mL flasks containing 25 mL M9-MOPS and antibiotics as detailed in Table 1, and by growing the cultures overnight.

The seed cultures were used to inoculate at an initial $OD_{600}$ of approximately 0.05 separate 250 mL flasks containing 40 mL M9-MOPS minimal medium, 45 ug/mL thiamine, micronutrients, 1.00E-5 mol/L FeSO4, 0.1 M MOPS, 0.5% yeast extract, 20 g/L of D-glucose, and antibiotics. The cultures were incubated at 30° C. in a humidified incubating shaker at 250 rpm until they reached an $OD_{600}$ of 0.2 to 0.3, at which point the production of β-farnesene in the host cells was induced by adding 40 uL of 1 M IPTG to the culture medium. At the time of induction, the cultures were overlain with 8 mL of an organic overlay to capture the β-farnesene. Samples were taken at various time points by transferring 100 uL samples of the upper organic overlay layer to a clean tube. The tube was centrifuged to separate out any remaining cells or media, and 10 uL of the organic overlay samples were transferred into 500 uL ethyl acetate spiked with beta- or trans-caryophyllene as an internal standard in clean glass GC vials. The mixtures were vortexed for 30 seconds, and then analyzed as described in Example 18. *Escherichia coli* host strain B653 produced approximately 7 mg/g DCW β-farnesene.

Example 21

This example describes the production of α-farnesene or β-farnesene in a *Saccharomyces cerevisiae* host strain.

Strain EPY300 was generated by removing the expression plasmid from *Saccharomyces cerevisiae* strain EPY224 (Ro et al. (2006) *Nature* 440: 940-943; PCT Patent Publication WO2007/005604) by culturing in rich medium. Strain EPY300 was then transformed with expression plasmids pRS425-FSA or pR425-FSB, yielding host strains Y166 and Y164, respectively.

Host cell transformants were selected on synthetic defined media, containing 2% glucose and all amino acids except leucine (SM-glu). The host strain EPY300 was auxotrophic for leucine biosynthesis (leu2), but expression plasmid pRS425-FSA or pRS425-FSB restores leucine prototrophy (LEU2). Single colonies were transferred to culture vials containing 5 mL of liquid SM-glu lacking leucine. The cultures were incubated by shaking at 30° C. until growth reaches stationary phase. The cells were stored at −80° C. in cryo-vials in I mL frozen aliquots made up of 400 μL 50% glycerol and 600 μL liquid culture.

Seed cultures were established by adding a stock aliquot to a 125 mL flask containing 25 mL SM-glu lacking leucine, and growing the cultures overnight. The seed cultures were used to inoculate at an initial $OD_{600}$ of approximately 0.05 250 mL baffled flasks containing 40 mL of synthetic defined media lacking leucine, 0.2% glucose, and 1.8% galactose. Cultures were incubated at 30° C. on a rotary shaker at 200 rpm. Because the presence of glucose in the media prevents induction of the Gal1 promoter by galactose, farnesene production was not induced until the cells use up the glucose in the media and switch to using galactose as their main carbon source. The cultures are overlain with 8 mL methyl oleate or isopropyl myristate. Samples were taken once every 24 hours by transferring 2-10 uL of the organic solvent layer to a clean glass vial containing 500 uL ethyl acetate containing a known concentration of beta- or trans-caryophyllene as an internal standard. In addition, 0.5 mL aliquots of the whole culture broth were added to a glass vials containing 1 mL ethyl acetate spiked with trans-caryophyllene as an internal standard. The whole culture broth samples were extracted in the ethyl acetate by vortexing the glass vials for 10 minutes, after which 600 uL of the ethyl acetate extraction was transferred to a clean glass vial.

Host strain Y166 produced approximately 9.8 mg/L of a-farnesene at 120 hours (averaged over 3 independent clones), and had a maximal specific productivity of approximately 3 mg/L/$OD_{600}$ (1 representative clone). Host strain Y164 produced approximately 56 mg/L of β-farnesene at 120 hours (averaged over 3 independent clones), and had a maximal specific productivity of approximately 20 mg/L/$OD_{600}$ (1 representative clone).

Example 22

This example describes the production of γ-terpinene, α-pinene, and terpinolene in *Escherichia coli* host strains.

Seed cultures of host strains for production of γ-terpinene (*E. coli* DH1-T1r [pMevT, pMevB-Gpps, pAM445]), α-pinene (*E. coli* DH1-T1r [pMevT, pMevB-Gpps, pAM443 or pAM442]) or terpinolene (*E. coli* DH1-T1r [pMevT, pMevB-Gpps, pAM444] were established by adding a stock aliquot of each strain to separate 125 mL flasks containing 25 mL M9-MOPS, 2% glucose, 0.5% yeast extract, and antibiotics as detailed in Table 1, and by growing the cultures overnight to late exponential phase.

The seed cultures were used to inoculate at an initial $OD_{600}$ of approximately 0.05, 250 mL flasks containing 40 mL M9-MOPS, 2% glucose, 0.5% yeast extract, and antibiotics. At time of inoculation, the cultures were also overlain with 4 mL hexadecane. Cultures were incubated at 30° C. on a rotary shaker at 200-250 rpm until they reached an $OD_{600}$ of approximately 0.2, at which point the production of the compound of interest in the host cells in the host cells was induced by adding 40 uL of 1 M IPTG. Samples were taken once per day for 96 hours by transferring 200 uL of the hexadecane layer to a 0.6 mL microfuge tube. For analysis, the hexadecane overlay was diluted 1:1 or 1:10 with ethyl acetate spiked with trans-caryophyllene as an internal standard in a 1.8 mL GC vial. In addition, 1 mL aliquots of the cultures were spun down, cell pellets were resuspended in 250 uL sterile water, and the cell suspensions were transferred to a glass vial containing 1 mL ethyl acetate spiked with trans-caryophyllene as an internal standard. The cell pellets were extracted in the ethyl acetate by vortexing the glass vials for 15 minutes, after which 500 uL of the ethyl acetate extraction was transferred to a clean glass vial.

The hexadecane/ethyl acetate samples and the ethyl acetate-extracted cell pellet samples were analyzed on an Agilent 6890N gas chromatograph equipped with an Agilent 5975 mass spectrometer (GC/MS) in full scan mode (50-500 m/z). To expedite run times, the temperature program and column matrix was modified to achieve optimal peak resolution and the shortest overall runtime. A 1 μL sample was split (a split ratio between 1:2 and 1:50 was selected based on sample concentration) and then separated using a HP-5MS column (Agilent Technologies, Inc., Palo Alto, Calif.) and helium carrier gas. The temperature program for the analysis was as follows: 75° C. hold for 3 minutes, increasing temperature at 20° C./minute to a temperature of 115° C., increasing temperature at 60° C./minute to a temperature of 300° C., and a hold at 300° C. for 0.5 minute. The various products, γ-terpinene, α-pinene, and terpinolene were observed at 5.4, 4.1, 5.4, and 5.9 minutes, respectively. Titers were calculated by comparing generated peak areas against a quantitative calibration curve of purified standards in trans-caryophyllene-spiked ethyl acetate.

Example 23

This example describes the production of linalool, limonene, β-pinene, β-phellandrene, carene, or sabinine in *Escherichia coli* host strains.

Seed cultures are established by adding a stock aliquot of each strain to separate 125 mL flasks containing 25 mL M9-MOPS, 0.5% yeast extract, 2% glucose, and antibiotics as detailed in Table 1, and by growing the cultures overnight.

The seed cultures are used to inoculate at an initial $OD_{600}$ of approximately 0.05, 250 mL baffled flasks containing 40 mL M9-MOPS, 0.5% yeast extract, 2% glucose, and antibiotics. Cultures are incubated at 30° C. on a rotary shaker at 250 rpm until they reach an $OD_{600}$ of approximately 0.2, at which point the production of the compound of interest in the host cells is induced by adding 40 ul of 1 M IPTG to the culture medium. The compound of interest is separated from the culture medium through solvent-solvent extraction, or by settling and decantation if the titer of the compound of interest is large enough to saturate the media and to form a second phase.

What is claimed is:

1. A method for producing a $C_{10}$, $C_{15}$, $C_{20}$ or $C_{20+}$ isoprenoid compound, comprising:
   a) preparing a first phase, comprising:
      i) an aqueous medium comprising a carbon source; and
      ii) a plurality of host cells capable of making at least one $C_{10}$, $C_{15}$, $C_{20}$ or $C_{20+}$ isoprenoid compound from said carbon source;
   b) culturing said plurality of host cells to produce the at least one $C_{10}$, $C_{15}$, $C_{20}$ or $C_{20+}$ isoprenoid compound;
   c) spontaneously forming a liquid organic second phase in a vessel having a capacity of at least 100 liters, said second phase comprising at least 90% of said at least one isoprenoid compound, wherein the second phase is in contact with the first phase;
   d) separating at least a portion of said second phase from said first phase, forming a separated second phase; and
   e) isolating said at least one isoprenoid compound from said separated second phase.

2. The method as in claim 1, wherein the at least one isoprenoid compound is a $C_{10}$ isoprenoid compound.

3. The method as in claim 1 wherein the at least one isoprenoid compound is a $C_{15}$ isoprenoid compound.

4. The method as in claim 1, wherein the at least one isoprenoid compound is a $C_{20}$ isoprenoid compound.

5. The method as in claim 1, wherein the at least one isoprenoid compound is a $C_{20+}$ compound.

6. The method of claim 1, wherein the isolation step comprises adsorption.

7. The method of claim 1, wherein the isolation step comprises distillation.

8. The method of claim 1, wherein the isolation step comprises gas-liquid extraction.

9. The method of claim 1, wherein the isolation step comprises liquid-liquid extraction.

10. The method of claim 1, wherein the isolation step comprises ultrafiltration.

11. The method of claim 1, wherein said second phase consists essentially of the $C_{10}$, $C_{15}$, $C_{20}$ or $C_{20+}$ isoprenoid compound.

12. The method of claim 1, wherein said culturing of said plurality of host cells is continuous.

13. The method of claim 1, wherein the organic second phase comprises substantially all of said at least one $C_{10}$, $C_{15}$, $C_{20}$ or $C_{20+}$ isoprenoid compound.

* * * * *